(12) United States Patent
Flitsch et al.

(10) Patent No.: US 10,451,897 B2
(45) Date of Patent: Oct. 22, 2019

(54) COMPONENTS WITH MULTIPLE ENERGIZATION ELEMENTS FOR BIOMEDICAL DEVICES

(71) Applicant: Johnson & Johnson Vision Care, Inc., Jacksonville, FL (US)

(72) Inventors: Frederick A. Flitsch, New Windsor, NY (US); Daniel B. Otts, Fruit Cove, FL (US); Randall B. Pugh, St. Johns, FL (US); James Daniel Riall, St. Johns, FL (US); Adam Toner, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 238 days.

(21) Appl. No.: 14/804,572

(22) Filed: Jul. 21, 2015

(65) Prior Publication Data

US 2015/0323811 A1    Nov. 12, 2015

Related U.S. Application Data

(63) Continuation-in-part of application No. 13/358,916, filed on Jan. 26, 2012, now Pat. No. 9,110,310.

(60) Provisional application No. 62/040,178, filed on Aug. 21, 2014, provisional application No. 61/454,205, filed on Mar. 18, 2011.

(51) Int. Cl.
*H01M 2/10* (2006.01)
*G02C 7/08* (2006.01)
(Continued)

(52) U.S. Cl.
CPC ............ *G02C 7/083* (2013.01); *G02C 7/04* (2013.01); *H01M 2/1066* (2013.01);
(Continued)

(58) Field of Classification Search
CPC ............ H01M 2/1066; H01M 2220/30; H01L 2224/45139; H01L 2224/48145;
(Continued)

(56) References Cited

U.S. PATENT DOCUMENTS 754,804 A    3/1904    Pratt
787,657 A    4/1905    Quimby
(Continued)

FOREIGN PATENT DOCUMENTS

AR    73391 A1    11/2010
AR    73742 A1    12/2010
(Continued)

OTHER PUBLICATIONS

Pandey, J.; Yu-Te Liao; Lingley, A.; Mirjalili, R.; Parviz, B.; Otis, B.P., "A Fully Integrated RF-Powered Contact Lens With a Single Element Display," Biomedical Circuits and Systems, IEEE Transactions on, vol. 4, No. 6, pp. 454,461, Dec. 2010.
(Continued)

*Primary Examiner* — Gregg Cantelmo

(57) ABSTRACT

Methods and apparatus to form biocompatible energization elements are described. In some embodiments, the methods and apparatus to form the biocompatible energization elements involve forming cavities comprising active cathode chemistry. The active elements of the cathode and anode are sealed with a laminate stack of biocompatible material. In some embodiments, a field of use for the methods and apparatus may include any biocompatible device or product that requires energization elements.

1 Claim, 19 Drawing Sheets

(51) Int. Cl.
  *G02C 7/04* (2006.01)
  *A61N 1/37* (2006.01)
  *A61N 1/378* (2006.01)

(52) U.S. Cl.
  CPC .......... *A61N 1/378* (2013.01); *G02C 2202/16* (2013.01); *H01L 2224/45139* (2013.01); *H01L 2224/48145* (2013.01); *H01L 2924/00014* (2013.01); *H01L 2924/01015* (2013.01); *H01L 2924/01047* (2013.01); *H01L 2924/10253* (2013.01); *H01L 2924/13091* (2013.01)

(58) Field of Classification Search
  CPC . H01L 2924/00014; H01L 2924/01015; H01L 2924/01047; H01L 2924/10253; H01L 2924/13091; A61N 1/378; G02C 7/083; G02C 7/04; G02C 202/16
  See application file for complete search history.

(56) References Cited

U.S. PATENT DOCUMENTS

| | | |
|---|---|---|
| 1,390,765 A | 9/1921 | Cox |
| 1,559,562 A | 11/1925 | Edison |
| 2,871,281 A | 1/1959 | Moulton |
| 2,991,324 A | 7/1961 | Vogt |
| 3,291,296 A | 12/1966 | Lemkelde |
| 3,306,776 A | 2/1967 | Tamminen |
| 3,353,998 A | 11/1967 | Langguth |
| 3,375,136 A | 3/1968 | Biggar |
| 3,431,327 A | 3/1969 | Tsuetaki |
| 3,642,539 A | 2/1972 | Akira |
| 4,118,860 A | 10/1978 | Buckler et al. |
| 4,125,686 A | 11/1978 | Kinsman |
| 4,254,191 A | 3/1981 | Kniazzeh |
| 4,268,132 A | 5/1981 | Neefe |
| 4,294,891 A | 10/1981 | Flitsch et al. |
| 4,408,023 A | 10/1983 | Gould et al. |
| 4,522,897 A | 6/1985 | Walsh |
| 4,592,944 A | 6/1986 | Clark |
| 4,601,545 A | 7/1986 | Kern |
| 4,772,517 A | 9/1988 | Muenstedt et al. |
| 4,783,237 A | 11/1988 | Aine et al. |
| 4,787,903 A | 11/1988 | Grendahl |
| 4,816,031 A | 3/1989 | Pfoff |
| 4,846,031 A | 7/1989 | Voytilla et al. |
| 4,921,728 A | 5/1990 | Takiguchi |
| 4,939,000 A | 7/1990 | Dodds et al. |
| 4,977,046 A | 12/1990 | Bleszinski, Jr. et al. |
| 5,112,703 A | 5/1992 | Koenig |
| 5,168,018 A | 12/1992 | Yoshizawa et al. |
| 5,219,497 A | 6/1993 | Blum |
| 5,227,805 A | 7/1993 | King |
| 5,358,539 A | 10/1994 | Dawson et al. |
| 5,430,693 A | 7/1995 | Ganter et al. |
| 5,435,874 A | 7/1995 | Takeuchi et al. |
| 5,478,420 A | 12/1995 | Gauci |
| 5,492,782 A | 2/1996 | Higley |
| 5,540,741 A | 7/1996 | Gozdz et al. |
| 5,549,988 A | 8/1996 | Reichert et al. |
| 5,568,353 A | 10/1996 | Bai et al. |
| 5,596,567 A | 1/1997 | deMuro |
| 5,600,180 A | 2/1997 | Kusaka et al. |
| 5,607,485 A | 3/1997 | Gozdz et al. |
| 5,682,210 A | 10/1997 | Weirich |
| 5,712,721 A | 1/1998 | Large |
| 5,792,574 A | 8/1998 | Mitate et al. |
| 5,928,808 A | 7/1999 | Eshraghi |
| 6,004,691 A | 12/1999 | Eshraghi |
| 6,134,188 A | 10/2000 | Ganter et al. |
| 6,168,884 B1 | 1/2001 | Neudecker et al. |
| 6,217,171 B1 | 4/2001 | Auten |
| 6,242,132 B1 | 6/2001 | Neudecker et al. |
| 6,269,266 B1 | 7/2001 | Chiao et al. |
| 6,273,904 B1 | 8/2001 | Chen et al. |
| 6,277,520 B1 | 8/2001 | Moutsios et al. |
| 6,282,668 B1 | 8/2001 | Neudecker |
| 6,316,142 B1 | 11/2001 | Delnick et al. |
| 6,322,589 B1 | 11/2001 | Cumming |
| 6,355,501 B1 | 3/2002 | Fung et al. |
| 6,364,482 B1 | 4/2002 | Roffman |
| 6,379,835 B1 | 4/2002 | Kucherovsky et al. |
| 6,434,429 B1 | 8/2002 | Kraus et al. |
| 6,447,669 B1 | 9/2002 | Lain |
| 6,470,215 B1 | 10/2002 | Kraus et al. |
| 6,477,410 B1 | 11/2002 | Henley |
| 6,490,487 B1 | 12/2002 | Kraus et al. |
| 6,517,974 B1 | 2/2003 | Kobayashi et al. |
| 6,544,171 B2 | 4/2003 | Beetz et al. |
| 6,553,262 B1 | 4/2003 | Lang et al. |
| 6,574,509 B1 | 6/2003 | Kraus et al. |
| 6,599,778 B2 | 7/2003 | Pogge et al. |
| 6,622,043 B1 | 9/2003 | Kraus et al. |
| 6,638,304 B2 | 10/2003 | Azar |
| 6,770,176 B2 | 8/2004 | Benson et al. |
| 6,852,254 B2 | 2/2005 | Spaulding |
| 6,893,395 B1 | 5/2005 | Kraus et al. |
| 6,924,036 B2 | 8/2005 | Polastri |
| 7,324,287 B1 | 1/2008 | Gollier |
| 7,404,636 B2 | 7/2008 | Blum |
| 7,407,728 B2 | 8/2008 | Wenneis et al. |
| 7,410,700 B2 | 8/2008 | Wang |
| 7,423,801 B2 | 9/2008 | Kaufman |
| 7,548,040 B2 | 6/2009 | Lee |
| 7,581,124 B1 | 8/2009 | Jacobson |
| 7,755,583 B2 | 7/2010 | Meredith |
| 7,794,511 B2 | 9/2010 | Johnson et al. |
| 7,794,643 B2 | 9/2010 | Watanabe |
| 7,798,301 B2 | 9/2010 | Keating |
| 7,876,573 B2 | 1/2011 | Motohara |
| 7,901,811 B2 | 3/2011 | Hambitzer et al. |
| 7,959,769 B2 | 6/2011 | Zhang et al. |
| 7,968,991 B2 | 6/2011 | Wong |
| 7,985,500 B2 | 7/2011 | Root et al. |
| 7,991,934 B2 | 8/2011 | Yao |
| 7,993,773 B2 | 8/2011 | Snyder et al. |
| 8,014,164 B2 | 9/2011 | Yang |
| 8,014,166 B2 | 9/2011 | Yazdani |
| 8,061,130 B2 | 11/2011 | Shibasaki |
| 8,309,397 B2 | 11/2012 | Shim |
| 8,343,216 B2 | 1/2013 | Brady |
| 8,433,409 B2 | 4/2013 | Martin et al. |
| 8,579,435 B2 | 11/2013 | Blum |
| 8,857,983 B2 | 10/2014 | Pugh et al. |
| 8,950,862 B2 | 2/2015 | Pugh |
| 9,102,111 B2 | 8/2015 | Pugh et al. |
| 9,110,310 B2 | 8/2015 | Pugh et al. |
| 9,134,546 B2 | 9/2015 | Pugh et al. |
| 9,195,075 B2 | 11/2015 | Pugh et al. |
| 9,233,513 B2 | 1/2016 | Pugh et al. |
| 9,296,158 B2 | 3/2016 | Pugh et al. |
| 9,601,780 B2 | 3/2017 | Kato et al. |
| 9,746,695 B2 | 8/2017 | Flitsch et al. |
| 2002/0009649 A1 | 1/2002 | Sato et al. |
| 2002/0041027 A1 | 4/2002 | Sugizaki |
| 2002/0041999 A1 | 4/2002 | Moutsios et al. |
| 2002/0058151 A1 | 5/2002 | Uchikoba |
| 2002/0110728 A1 | 8/2002 | Gozdz et al. |
| 2002/0162631 A1 | 11/2002 | Wien |
| 2003/0002160 A1 | 1/2003 | Johnson et al. |
| 2003/0021601 A1 | 1/2003 | Goldstein |
| 2003/0059526 A1 | 3/2003 | Benson et al. |
| 2003/0064292 A1 | 4/2003 | Neudecker et al. |
| 2003/0068559 A1 | 4/2003 | Armstrong et al. |
| 2003/0069666 A1 | 4/2003 | Nagler |
| 2003/0137922 A1 | 7/2003 | Ro |
| 2003/0146414 A1 | 8/2003 | Ndzebet |
| 2003/0165744 A1 | 9/2003 | Schubert et al. |
| 2003/0207978 A1 | 11/2003 | Yadav et al. |
| 2004/0000732 A1 | 1/2004 | Spaulding |
| 2004/0027536 A1 | 2/2004 | Blum |
| 2004/0062985 A1 | 4/2004 | Aamodt et al. |
| 2004/0084790 A1 | 5/2004 | Blum |
| 2004/0091779 A1 | 5/2004 | Kang et al. |

(56) References Cited

U.S. PATENT DOCUMENTS

| | | |
|---|---|---|
| 2004/0131925 A1 | 7/2004 | Jenson |
| 2004/0239784 A1 | 12/2004 | Ibe |
| 2004/0239874 A1 | 12/2004 | Swab |
| 2004/0241528 A1 | 12/2004 | Sarpeshkar et al. |
| 2004/0242794 A1 | 12/2004 | Kanazawa |
| 2004/0258982 A1 | 12/2004 | Coffey et al. |
| 2005/0009959 A1 | 1/2005 | Bair et al. |
| 2005/0031959 A1 | 2/2005 | Kato et al. |
| 2005/0036109 A1 | 2/2005 | Blum |
| 2005/0069760 A1 | 3/2005 | Somatomo |
| 2005/0099594 A1 | 5/2005 | Blum |
| 2005/0147877 A1 | 7/2005 | Tarnowski et al. |
| 2005/0185135 A1 | 8/2005 | Blum et al. |
| 2005/0208381 A1 | 9/2005 | Boulton et al. |
| 2005/0231377 A1 | 10/2005 | Sunderman et al. |
| 2005/0231677 A1 | 10/2005 | Meredith |
| 2005/0255079 A1 | 11/2005 | Santerre |
| 2005/0271796 A1 | 12/2005 | Neudecker et al. |
| 2006/0001137 A1 | 1/2006 | Hundt |
| 2006/0024567 A1 | 2/2006 | Heller et al. |
| 2006/0026201 A1 | 2/2006 | Cabillic |
| 2006/0026505 A1 | 2/2006 | Mani |
| 2006/0038536 A1 | 2/2006 | Lafollette et al. |
| 2006/0065989 A1 | 3/2006 | Druffel et al. |
| 2006/0066808 A1 | 3/2006 | Blum et al. |
| 2006/0095128 A1 | 5/2006 | Blum |
| 2006/0099496 A1 | 5/2006 | Aamodt et al. |
| 2006/0127761 A1 | 6/2006 | Phillips et al. |
| 2006/0152912 A1 | 7/2006 | Karrer |
| 2006/0166088 A1 | 7/2006 | Hokanson et al. |
| 2006/0181676 A1 | 8/2006 | Tucker et al. |
| 2006/0202359 A1 | 9/2006 | Chen |
| 2006/0204839 A1 | 9/2006 | Richards et al. |
| 2006/0210877 A1 | 9/2006 | Manko et al. |
| 2006/0226556 A1 | 10/2006 | Kurita |
| 2006/0234121 A1 | 10/2006 | Kim et al. |
| 2006/0255441 A1 | 11/2006 | Ohta |
| 2006/0265058 A1 | 11/2006 | Silvestrini |
| 2006/0267167 A1 | 11/2006 | McCain |
| 2006/0267768 A1 | 11/2006 | Sabeta |
| 2007/0052876 A1 | 3/2007 | Kaufman |
| 2007/0090869 A1 | 4/2007 | Adewole |
| 2007/0125644 A1 | 6/2007 | Heller et al. |
| 2007/0128420 A1 | 6/2007 | Maghribi |
| 2007/0141463 A1 | 6/2007 | Stevanovic |
| 2007/0156184 A1 | 7/2007 | Root et al. |
| 2007/0159562 A1 | 7/2007 | Haddock |
| 2007/0231575 A1 | 10/2007 | Watanabe et al. |
| 2007/0242171 A1 | 10/2007 | Mori |
| 2007/0242173 A1 | 10/2007 | Blum |
| 2007/0285385 A1 | 12/2007 | Albert |
| 2008/0002149 A1 | 1/2008 | Fritsch et al. |
| 2008/0020127 A1 | 1/2008 | Whiteford |
| 2008/0020874 A1 | 1/2008 | Huang et al. |
| 2008/0024848 A1 | 1/2008 | Kawano |
| 2008/0024858 A1 | 1/2008 | Kaufman |
| 2008/0042227 A1 | 2/2008 | Asano |
| 2008/0048180 A1 | 2/2008 | Abe et al. |
| 2008/0058652 A1 | 3/2008 | Payne |
| 2008/0079396 A1 | 4/2008 | Yamazaki et al. |
| 2008/0086206 A1 | 4/2008 | Nasiatka |
| 2008/0101267 A1 | 5/2008 | Kurokawa |
| 2008/0187824 A1 | 8/2008 | Tomantschger |
| 2008/0208335 A1 | 8/2008 | Blum |
| 2008/0212007 A1 | 9/2008 | Meredith |
| 2008/0241683 A1 | 10/2008 | Fensore et al. |
| 2008/0261390 A1 | 10/2008 | Chen |
| 2008/0280184 A1 | 11/2008 | Yao et al. |
| 2009/0002012 A1 | 1/2009 | Doong |
| 2009/0003383 A1 | 1/2009 | Watanabe |
| 2009/0033863 A1 | 2/2009 | Blum |
| 2009/0042065 A1 | 2/2009 | Simon et al. |
| 2009/0042066 A1 | 2/2009 | Simon et al. |
| 2009/0046349 A1 | 2/2009 | Haddock |
| 2009/0050267 A1 | 2/2009 | Conlon et al. |
| 2009/0057289 A1 | 3/2009 | Williams |
| 2009/0079641 A1 | 3/2009 | Cruzado et al. |
| 2009/0091818 A1 | 4/2009 | Haddock |
| 2009/0092903 A1 | 4/2009 | Johnson et al. |
| 2009/0098281 A1 | 4/2009 | Zhang et al. |
| 2009/0105817 A1 | 4/2009 | Bretthauer et al. |
| 2009/0142656 A1 | 6/2009 | Nathan et al. |
| 2009/0175016 A1 | 7/2009 | Legen |
| 2009/0182426 A1 | 7/2009 | Von Arx |
| 2009/0202899 A1 | 8/2009 | Pyszczek |
| 2009/0204207 A1 | 8/2009 | Blum |
| 2009/0204454 A1 | 8/2009 | Lagudi |
| 2009/0206498 A1 | 8/2009 | Tepedino, Jr. et al. |
| 2009/0243125 A1 | 10/2009 | Pugh |
| 2009/0244477 A1 | 10/2009 | Pugh |
| 2009/0256977 A1 | 10/2009 | Haddock |
| 2009/0269392 A1 | 10/2009 | Tauber et al. |
| 2009/0278503 A1 | 11/2009 | Hundt et al. |
| 2009/0288405 A1 | 11/2009 | Shibasaki |
| 2010/0001926 A1 | 1/2010 | Amirparviz |
| 2010/0002190 A1 | 1/2010 | Clarke |
| 2010/0062342 A1 | 3/2010 | Li |
| 2010/0072643 A1 | 3/2010 | Pugh |
| 2010/0073534 A1 | 3/2010 | Yano |
| 2010/0076553 A1 | 3/2010 | Pugh |
| 2010/0078837 A1 | 4/2010 | Pugh et al. |
| 2010/0078838 A1 | 4/2010 | Pugh |
| 2010/0079724 A1 | 4/2010 | Pugh |
| 2010/0103368 A1 | 4/2010 | Amirparviz |
| 2010/0103369 A1 | 4/2010 | Pugh |
| 2010/0109175 A1 | 5/2010 | Pugh |
| 2010/0110372 A1 | 5/2010 | Pugh |
| 2010/0149777 A1 | 6/2010 | Yamamoto |
| 2010/0178543 A1 | 7/2010 | Gruner et al. |
| 2010/0211186 A1 | 8/2010 | Senders |
| 2010/0261071 A1 | 10/2010 | Lopatin et al. |
| 2010/0266895 A1 | 10/2010 | Tucholski |
| 2010/0295135 A1 | 11/2010 | Masuoka |
| 2010/0310932 A1 | 12/2010 | Leysieffer et al. |
| 2011/0007656 A1 | 1/2011 | He |
| 2011/0039150 A1 | 2/2011 | Wang et al. |
| 2011/0045112 A1 | 2/2011 | Pugh |
| 2011/0065706 A1 | 3/2011 | Wensley et al. |
| 2011/0074281 A1 | 3/2011 | Farquhar |
| 2011/0076567 A1 | 3/2011 | Bouillon |
| 2011/0076568 A1 | 3/2011 | Bouillon |
| 2011/0086077 A1 | 4/2011 | McCrea et al. |
| 2011/0091778 A1 | 4/2011 | Kambara et al. |
| 2011/0134683 A1 | 6/2011 | Yamazaki et al. |
| 2011/0143225 A1 | 6/2011 | Sakai et al. |
| 2011/0174431 A1 | 7/2011 | Darmes |
| 2011/0230963 A1 | 9/2011 | Cuevas |
| 2011/0284912 A1 | 11/2011 | Sekine et al. |
| 2011/0287318 A1 | 11/2011 | Loveness et al. |
| 2011/0311877 A1 | 12/2011 | Matsuda et al. |
| 2012/0024295 A1 | 2/2012 | Mihin |
| 2012/0026598 A1 | 2/2012 | Pugh |
| 2012/0057244 A1 | 3/2012 | Pugh |
| 2012/0088129 A1 | 4/2012 | Kaneda et al. |
| 2012/0092612 A1 | 4/2012 | Binder |
| 2012/0100412 A1 | 4/2012 | Kwon |
| 2012/0107666 A1 | 5/2012 | Bailey et al. |
| 2012/0115041 A1 | 5/2012 | West et al. |
| 2012/0156259 A1 | 6/2012 | Rau et al. |
| 2012/0162600 A1 | 6/2012 | Pugh |
| 2012/0171599 A1 | 7/2012 | Nakagawa et al. |
| 2012/0188467 A1 | 7/2012 | Escuti et al. |
| 2012/0196187 A1 | 8/2012 | Fujinami et al. |
| 2012/0218508 A1 | 8/2012 | Pugh et al. |
| 2012/0234453 A1 | 9/2012 | Pugh et al. |
| 2012/0235277 A1 | 9/2012 | Pugh |
| 2012/0236254 A1 | 9/2012 | Pugh |
| 2012/0236524 A1 | 9/2012 | Pugh |
| 2012/0242953 A1 | 9/2012 | Pugh et al. |
| 2012/0245444 A1 | 9/2012 | Otis |
| 2012/0259188 A1 | 10/2012 | Besling et al. |
| 2012/0282519 A1 | 11/2012 | Freitag et al. |
| 2013/0019540 A1 | 1/2013 | Magnus |
| 2013/0023005 A1 | 1/2013 | Chen et al. |

(56) References Cited

U.S. PATENT DOCUMENTS

| | | |
|---|---|---|
| 2013/0024575 A1 | 1/2013 | Taylor |
| 2013/0034760 A1 | 2/2013 | Otts et al. |
| 2013/0065122 A1 | 3/2013 | Chiang et al. |
| 2013/0089769 A1 | 4/2013 | Proctor et al. |
| 2013/0155371 A1 | 6/2013 | Zhang et al. |
| 2013/0194540 A1 | 8/2013 | Pugh |
| 2013/0196214 A1 | 8/2013 | Scott et al. |
| 2013/0215380 A1 | 8/2013 | Pugh et al. |
| 2013/0245754 A1 | 9/2013 | Blum |
| 2013/0245755 A1 | 9/2013 | Fehr |
| 2013/0266855 A1 | 10/2013 | Kim et al. |
| 2013/0266873 A1 | 10/2013 | Ishii et al. |
| 2013/0309547 A1 | 11/2013 | Bazzarella et al. |
| 2014/0000101 A1 | 1/2014 | Pugh et al. |
| 2014/0002788 A1 | 1/2014 | Otts et al. |
| 2014/0017557 A1 | 1/2014 | Lockett et al. |
| 2014/0036226 A1 | 2/2014 | Blum |
| 2014/0047742 A1 | 2/2014 | Schloss |
| 2014/0121557 A1 | 5/2014 | Gannon et al. |
| 2014/0147742 A1 | 5/2014 | Anastas et al. |
| 2014/0148899 A1 | 5/2014 | Fehr |
| 2014/0227574 A1 | 8/2014 | Savinell et al. |
| 2014/0272522 A1 | 9/2014 | Pugh et al. |
| 2014/0306361 A1 | 10/2014 | Pugh |
| 2014/0323968 A1 | 10/2014 | Rogers et al. |
| 2014/0342247 A1 | 11/2014 | Kishida et al. |
| 2015/0212339 A1 | 7/2015 | Pugh et al. |
| 2015/0214567 A1 | 7/2015 | Etzkorn et al. |
| 2015/0287960 A1 | 10/2015 | Andry et al. |
| 2015/0288023 A1 | 10/2015 | Andry et al. |
| 2015/0288024 A1 | 10/2015 | Andry et al. |
| 2015/0309337 A1 | 10/2015 | Flitsch et al. |
| 2015/0323811 A1 | 11/2015 | Zhang et al. |
| 2015/0378176 A1 | 12/2015 | Flitsch |
| 2016/0028101 A1 | 1/2016 | Flitsch et al. |
| 2016/0054589 A1 | 2/2016 | Flitsch et al. |
| 2016/0054590 A1 | 2/2016 | Otts et al. |
| 2016/0056440 A1 | 2/2016 | Flitsch et al. |
| 2016/0056459 A1 | 2/2016 | Flitsch et al. |
| 2016/0056498 A1 | 2/2016 | Birch et al. |
| 2017/0229730 A1 | 8/2017 | Flitsch et al. |

FOREIGN PATENT DOCUMENTS

| | | |
|---|---|---|
| AU | 2009293178 A1 | 3/2011 |
| AU | 2009293182 A1 | 3/2011 |
| AU | 2014201529 A1 | 10/2014 |
| BR | PI0919346 A2 | 12/2015 |
| CA | 2389907 A1 | 12/2003 |
| CA | 2737861 A1 | 3/2010 |
| CA | 2737865 A1 | 3/2010 |
| CN | 1344022 A | 4/2002 |
| CN | 1520983 A | 8/2004 |
| CN | 1808744 A | 7/2006 |
| CN | 101041258 A | 9/2007 |
| CN | 101062581 A | 10/2007 |
| CN | 101094626 A | 12/2007 |
| CN | 100403477 C | 7/2008 |
| CN | 101395520 A | 3/2009 |
| CN | 101669059 A | 3/2010 |
| CN | 101983122 A | 3/2011 |
| CN | 102005612 A | 4/2011 |
| CN | 102159381 A | 8/2011 |
| CN | 102159382 A | 8/2011 |
| CN | 102171028 A | 8/2011 |
| CN | 102196789 A | 9/2011 |
| CN | 102202874 A | 9/2011 |
| CN | 102271899 A | 12/2011 |
| CN | 102727218 A | 10/2012 |
| CN | 102959769 A | 3/2013 |
| CN | 203300756 U | 11/2013 |
| CN | 203733888 U | 7/2014 |
| CN | 102196789 A | 11/2014 |
| DE | 19858172 A1 | 6/2000 |
| DE | 102007048859 A1 | 4/2009 |
| EP | 0581964 A1 | 2/1994 |
| EP | 0918248 A2 | 5/1999 |
| EP | 1183745 A1 | 3/2002 |
| EP | 1262307 A2 | 12/2002 |
| EP | 1313159 A2 | 5/2003 |
| EP | 1342560 A2 | 9/2003 |
| EP | 1262307 A3 | 11/2003 |
| EP | 1342560 A3 | 9/2004 |
| EP | 1736291 A2 | 12/2006 |
| EP | 1747879 A2 | 1/2007 |
| EP | 1736291 A3 | 3/2007 |
| EP | 1747879 A3 | 3/2007 |
| EP | 1760515 A2 | 3/2007 |
| EP | 1849574 A2 | 10/2007 |
| EP | 1849589 A2 | 10/2007 |
| EP | 1892788 A1 | 2/2008 |
| EP | 1342560 B1 | 7/2008 |
| EP | 1849589 A3 | 3/2009 |
| EP | 1262307 B1 | 2/2010 |
| EP | 1760515 A3 | 8/2011 |
| EP | 2349697 A2 | 8/2011 |
| EP | 2349698 A1 | 8/2011 |
| EP | 2485294 A1 | 8/2012 |
| EP | 2508935 A1 | 10/2012 |
| EP | 2564454 A1 | 3/2013 |
| EP | 2605314 A2 | 6/2013 |
| EP | 2620802 A1 | 7/2013 |
| EP | 2631962 A1 | 8/2013 |
| EP | 2779272 A1 | 9/2014 |
| EP | 2812750 A1 | 12/2014 |
| EP | 2996187 A2 | 3/2016 |
| EP | 2740170 B1 | 4/2016 |
| EP | 3016194 A1 | 5/2016 |
| GB | 743731 A | 1/1956 |
| GB | 1307393 A | 2/1973 |
| IL | 211275 | 4/2011 |
| IL | 211309 | 4/2011 |
| IL | 222620-D0 | 12/2012 |
| JP | S52146650 A | 12/1977 |
| JP | S57136774 A | 8/1982 |
| JP | S58116764 A | 7/1983 |
| JP | S63105319 U | 7/1988 |
| JP | 1286809 A | 11/1989 |
| JP | H0765817 A | 3/1995 |
| JP | H08162823 A | 6/1996 |
| JP | H08508826 A | 9/1996 |
| JP | H08264203 A | 10/1996 |
| JP | H09266636 A | 10/1997 |
| JP | H10209185 A | 8/1998 |
| JP | H10219185 A | 8/1998 |
| JP | H10229095 A | 8/1998 |
| JP | H11135712 A | 5/1999 |
| JP | 2000228213 A | 8/2000 |
| JP | 2000299542 A | 10/2000 |
| JP | 2001028036 A | 1/2001 |
| JP | 2001110445 A | 4/2001 |
| JP | 2002093385 A | 3/2002 |
| JP | 2002118198 A | 4/2002 |
| JP | 2002537580 A | 11/2002 |
| JP | 2003202525 A | 7/2003 |
| JP | 2004505667 A | 2/2004 |
| JP | 2004305313 A | 11/2004 |
| JP | 2005142050 A | 6/2005 |
| JP | 2005523483 A | 8/2005 |
| JP | 2005535942 A | 11/2005 |
| JP | 2006507541 A | 3/2006 |
| JP | 2006093659 A | 4/2006 |
| JP | 2006317321 A | 11/2006 |
| JP | 2007533098 A | 11/2007 |
| JP | 2007313594 A | 12/2007 |
| JP | 2008502016 A | 1/2008 |
| JP | 2008506031 A | 2/2008 |
| JP | 2008053134 A | 3/2008 |
| JP | 2008072111 A | 3/2008 |
| JP | 2008088019 A | 4/2008 |
| JP | 2008512348 A | 4/2008 |
| JP | 2008178226 A | 7/2008 |
| JP | 2008529208 A | 7/2008 |
| JP | 2008227068 A | 9/2008 |

(56) References Cited

FOREIGN PATENT DOCUMENTS

| | | |
|---|---|---|
| JP | 2008281095 A | 11/2008 |
| JP | 2009007629 A | 1/2009 |
| JP | 2009087895 A | 4/2009 |
| JP | 2010034254 A | 2/2010 |
| JP | 2010073533 A | 4/2010 |
| JP | 2010517081 A | 5/2010 |
| JP | 2010209855 A | 9/2010 |
| JP | 2010536158 A | 11/2010 |
| JP | 2011082586 A | 4/2011 |
| JP | 2011512565 A | 4/2011 |
| JP | 2011515157 A | 5/2011 |
| JP | 2011516922 A | 5/2011 |
| JP | 2011516927 A | 5/2011 |
| JP | 2011517659 A | 6/2011 |
| JP | 2012009820 A | 1/2012 |
| JP | 2012502823 A | 2/2012 |
| JP | 2012503222 A | 2/2012 |
| JP | 2012504065 A | 2/2012 |
| JP | 2012504257 A | 2/2012 |
| JP | 2012044074 A | 3/2012 |
| JP | 2012056758 A | 3/2012 |
| JP | 2012507747 A | 3/2012 |
| JP | 2013516255 A | 5/2013 |
| JP | 2013532010 A | 8/2013 |
| JP | 2013533046 A | 8/2013 |
| JP | 2013176558 A | 9/2013 |
| JP | 2013239263 A | 11/2013 |
| JP | 5591567 B2 | 9/2014 |
| JP | 5788668 B2 | 10/2015 |
| KR | 100625892 B1 | 9/2006 |
| KR | 20070009231 A | 1/2007 |
| KR | 20100102969 A | 9/2010 |
| KR | 20100132003 A | 12/2010 |
| KR | 2011069113 A | 6/2011 |
| KR | 2011073530 A | 6/2011 |
| KR | 20130096676 A | 8/2013 |
| RU | 2116891 C1 | 8/1998 |
| RU | 2307429 C1 | 9/2007 |
| RU | 2310952 C2 | 11/2007 |
| RU | 2320378 C2 | 3/2008 |
| RU | 2380794 C1 | 1/2010 |
| RU | 2563842 C2 | 9/2015 |
| SG | 10201400548X A | 10/2014 |
| SG | 10201506558W A1 | 3/2016 |
| TW | 200532278 A | 10/2005 |
| TW | 200629549 A | 8/2006 |
| TW | 200916832 A | 4/2009 |
| TW | 200950960 A | 12/2009 |
| TW | 201003172 A | 1/2010 |
| TW | 201024827 A | 7/2010 |
| TW | 201026489 A | 7/2010 |
| TW | 201029830 A | 8/2010 |
| TW | 201140756 A | 11/2011 |
| WO | WO1994023334 A1 | 10/1994 |
| WO | WO-9717737 A1 | 5/1997 |
| WO | WO-0004601 A1 | 1/2000 |
| WO | WO-0057504 A1 | 9/2000 |
| WO | WO-0229836 A1 | 4/2002 |
| WO | WO-03035166 A2 | 5/2003 |
| WO | WO-03069700 A2 | 8/2003 |
| WO | WO-03078300 A1 | 9/2003 |
| WO | WO2003090611 A1 | 11/2003 |
| WO | WO-2004015460 A2 | 2/2004 |
| WO | WO-2004015460 A3 | 6/2004 |
| WO | WO-03069700 A3 | 8/2004 |
| WO | WO-2004093786 A2 | 11/2004 |
| WO | WO-2005064712 A1 | 7/2005 |
| WO | WO2005088388 A1 | 9/2005 |
| WO | WO-2005098994 A1 | 10/2005 |
| WO | WO2006050171 A2 | 5/2006 |
| WO | WO-2006077192 A1 | 7/2006 |
| WO | WO2006078103 A1 | 7/2006 |
| WO | WO-2006078472 A2 | 7/2006 |
| WO | WO-2006050171 A3 | 9/2006 |
| WO | WO-2005098994 A9 | 11/2006 |
| WO | WO-2006115649 A2 | 11/2006 |
| WO | WO2007050402 A2 | 5/2007 |
| WO | WO-2006115649 A3 | 6/2007 |
| WO | WO-2007072781 A1 | 6/2007 |
| WO | WO2007081959 A2 | 7/2007 |
| WO | WO-2007102692 A1 | 9/2007 |
| WO | WO-2008010390 A1 | 1/2008 |
| WO | WO-2008039806 A2 | 4/2008 |
| WO | WO-2007081959 A3 | 5/2008 |
| WO | WO-2008039806 A3 | 7/2008 |
| WO | WO2008091859 A1 | 7/2008 |
| WO | WO2008103906 A2 | 8/2008 |
| WO | WO2008109867 A2 | 9/2008 |
| WO | WO-2008109867 A3 | 10/2008 |
| WO | WO-2008103906 A3 | 11/2008 |
| WO | WO-2009012463 A2 | 1/2009 |
| WO | WO-2009018315 A2 | 2/2009 |
| WO | WO-2009025763 A2 | 2/2009 |
| WO | WO-2007050402 A3 | 3/2009 |
| WO | WO-2009038897 A2 | 3/2009 |
| WO | WO-2009038897 A3 | 6/2009 |
| WO | WO2009105261 A1 | 8/2009 |
| WO | WO2009109867 A2 | 9/2009 |
| WO | WO-2009113296 A1 | 9/2009 |
| WO | WO-2009117506 A2 | 9/2009 |
| WO | WO-2009117506 A3 | 1/2010 |
| WO | WO2010033679 A2 | 3/2010 |
| WO | WO-2010033683 A1 | 3/2010 |
| WO | WO-2010039610 A2 | 4/2010 |
| WO | WO-2010051203 A1 | 5/2010 |
| WO | WO2010051225 A1 | 5/2010 |
| WO | WO-2010058574 A1 | 5/2010 |
| WO | WO-2010033679 A3 | 6/2010 |
| WO | WO-2010051225 A9 | 6/2010 |
| WO | WO-2010062504 A2 | 6/2010 |
| WO | WO-2010039610 A3 | 7/2010 |
| WO | WO-2010082993 A2 | 7/2010 |
| WO | WO-2010082993 A3 | 9/2010 |
| WO | WO-2010119754 A1 | 10/2010 |
| WO | WO2010133317 A1 | 11/2010 |
| WO | WO-2011005216 A1 | 1/2011 |
| WO | WO-2011007548 A1 | 1/2011 |
| WO | WO-2011015866 A1 | 2/2011 |
| WO | WO-2011083105 A1 | 7/2011 |
| WO | WO-2010133317 A9 | 10/2011 |
| WO | WO-2011137239 A1 | 11/2011 |
| WO | WO-2011153158 A1 | 12/2011 |
| WO | WO2011163080 A1 | 12/2011 |
| WO | WO-2012013774 A1 | 2/2012 |
| WO | WO-2012018583 A1 | 2/2012 |
| WO | WO-2012023774 A2 | 2/2012 |
| WO | WO-2012046854 A1 | 4/2012 |
| WO | WO-2012129210 A2 | 9/2012 |
| WO | WO-2013019525 A1 | 2/2013 |
| WO | WO03065481 | 8/2013 |
| WO | WO2013112748 A1 | 8/2013 |
| WO | WO-2013128206 A1 | 9/2013 |
| WO | WO2014010526 A1 | 1/2014 |
| WO | WO-2014049089 A1 | 4/2014 |
| WO | WO-2014071571 A1 | 5/2014 |

OTHER PUBLICATIONS

Loy, M., et al., "ISM-Band and Short Range Device Antennas", Texas Instruments Application Report, Aug. 2005. Online: http://www.ti.com/lit/answra046a/.

Pandey, J., et al. "Toward an Active Contact Lens: Integration of a Wireless Power Harvesting IC", Dept. of Elect. Eng., University of Washington, Seattle, WA, USA. Biomedical Circuits and Systems Conference, 2009. BioCAS 2009. IEEE Issue Date: Nov. 26-28, 2009 pp. 125-128 online: http:/wireless.ee.washington.edu/papers/biocas2009 inpyudodpo.pdf.

Williams, A. "Swiss Startup Puts MEMS Sensor in Contact Lens", Electronics Weekly.com, Mar. 25, 2010, 9:29 AM online: http://www.electronicsweekly.com/blogs/uk-technology-startups/2010/03/swi- ss-startup-puts-mems-sensor.tml.

(56) References Cited

OTHER PUBLICATIONS

Davies, C., "Opto-Electronic Contact Lenses Promise Wireless Displays", Nov. 25, 2009. Online: http://www.slashgear.com/opto-electronic-contact-lenses-promise-wireless-- displays-2564454/.

Orca, Surfdaddy, "Micro Machines and Opto-Electronics on a Contact Lens", Nov. 20, 2009. Online: http://www.hplusmagazine.com/arraicles/toys-tools/micro-machines-and-opto- -electronics-contact-lens.

Parviz, Babak, A., "Augmented Reality in a Contact Lens, A New Generation of Contact Lenses Built With Very Small Circuits and LEDs Promises Bionic Eyesight", IEEE Spectrum.org/biomedical/bionics, downloaded Jul. 10, 2012.

Gosalia K.,: "Novel Compact Antennas for Biomedical Implants and Wireless Applications", PhD Dissertation, North Carolina State University, 2004.

Ratta, Varun "Crystallization, Morphology, Thermal Stability and Adhesive Properties of Novel High Performance Semicrystalline Polyimides" PhD Dissertation defended Apr. 26, 1999 Virginia Tech University, entire Chapter 4.

Albano F., et al., "Design of an Implantable Power Supply for an Intraocular Sensor, Using POWER (Power Optimization for Wireless Energy Requirements)," Journal of Power Sources, Jun. 2007, vol. 170 (1), pp. 216-224.

Belyaeva E.A., et al., "Mechanism(s) of Toxic Action of Zn2+ and Selenite: A Study on AS-30D Hepatoma Cells and Isolated Mitochondria," Biochemistry Research International, Jan. 2011, vol. 42 (6), 13 pages.

Benefits of PVC (Year: 2018), 1 page.

Beynw E., "3D System Integration Technologies", 2006, IEEE, International Symposium on VLSI Technology, System and Applications, 2006, 9 pages.

Breakthrough Technologies Driving Successful Energy Harvesting-Powered Products, PSMA Energy Harvesting Forum, Mar. 2014. [retrieved on Jan. 22, 2018] Retrieved from the Internet:[URL:http://www.psma.com/sites/default/files/uploads/tech-forums-energy-harvesting/presentations/is 1-1-1-energy-harvesting-market -requirements-economicsv]. 0.

Bruno L.J.S., et al., "Correlation Between Morphological Properties and Ionic Conductivity in an Electrolyte Based on Poly(Vinylidene Fluoride) and Poly(2-hydroxyethyl Methacrylate)," Materials Research, Feb. 2014, vol. 17 (1), pp. 115-120, XP055227556.

Cohenladdad J.P., et al., "NMR Study of the Demixing Process in Concentrated polyisobutylene Solutions," Journal of Polymer Science: Polymer Physics Edition, Sep. 1981, vol. 19 (9), pp. 1395-1403.

Extended European Search Report for Application No. 13152733.5, dated Apr. 30. 2013, 7 pages.

Extended European Search Report for Application No. 13155410, dated Jun. 5, 2013, 5 pages.

Extended European Search Report for Application No. 13156410, dated Jun. 13, 2013, 8 pages.

Extended European Search Report for Application No. 14159971, dated Jun. 5, 2014, 6 pages.

Extended European Search Report for Application No. 18160035.4, dated Jun. 27, 2018, 20 pages.

Extended European Search Report for Application No. EP13156428, dated Jun. 6, 2013, 9 pages.

Extended European Search Report for Application No. EP15181836, dated Dec. 1, 2015, 12 pages.

Extended European Search Report for Application No. EP15181868, dated Jan. 12, 2016, 12 pages.

Extended European Search Report for Application No. EP15181875, dated Jun. 14, 2016, 12 pages.

Extended European Search Report for Application No. EP13702567.2, dated Aug. 2. 2018, 8 pages.

Extended European Search Report for Application No. EP15181799, dated Jun. 14, 2016, 23 pages.

Extended European Search Report for Application No. EP15181817, dated Feb. 15, 2016, 13 pages.

Extended European Search Report for Application No. EP15181854, dated May 18, 2016, 11 pages.

Extended European Search Report for Application No. EP15181855, date May 3, 2016, 13 pages.

Extended European Search Report for Application No. EP15181857, dated Dec. 9, 2015, 8 pages.

Extended European Search Report for Application No. EP15181860, dated Feb. 17 2016, 15 pages.

Extended European Search Report for Application No. EP15181862, dated Apr. Apr. 18, 2016, 12 pages.

Extended European Search Report for Application No. EP15181863, dated Apr. 22, 2016, 14 pages.

Extended European Search Report for Application No. EP15181865, dated Aug. 2, 2016, 21 pages.

Extended European Search Report for Application No. EP15181872, dated Apr. 5, 2016, 12 pages.

Extended European Search Report for Application No. EP15181874, dated Feb. 19, 2016, 11 pages.

Extended European Search Report for Application No. EP16200268, dated Jan. 20, 2017, 8 pages.

Extended European Search Report for Application No. EP16200270, dated Jan. 5, 2017, 8 pages.

Extended European Search Report for Application No. EP17205191, dated Jan. 30, 2018, 14 pages.

Extended European Search Report for Application No. EP18169197, dated Jul. 27, 2018, 8 pages.

Gaikwad A.M., et al., "A High Areal Capacity Flexible Lithium-Ion Battery with a Strain-Compliant Design," Advanced Energy Materials, Feb. 2015, vol. 5 (3), 11 pages.

Gaikwad A.M., et al., "Recent Progress on Printed Flexible Batteries: Mechanical Challenges, Printing Technologies, and Future Prospects," Energy Technology, 2000, pp. 1-25.

Geduld H., "Zinc Plating," Jan. 1988, Columbia Chemical Corp., Macedonia, OH, 6 pages.

Herb G., Zinc Plating [Online], Jan. 1, 1988 [retrieved on 2016-07-20]. Retrieved from the Internet: (URL:http://infohouse.p2ric.orgjref/29/28085.pdf), XP055290076.

Hill J., "How to Uniformly Disperse Nanoparticles in Battery Cathode Coatings," Advanced Materials and Processes, May 2010, vol. 168 (5), pp. 34-36.

International Preliminary Report for Patentability for Application No. PCT/US2013/023005, dated Jul. 29, 2014, 5 pages.

International Preliminary Report on Patentability for Application No. PCT/US2009/057284, dated Mar. 22, 2011, 10 pages.

International Preliminary Report on Patentability for Application No. PCT/US2009/057289, dated Mar. 22, 2011, 6 pages.

International Preliminary Report on Patentability for Application No. PCT/US2012/026849, dated Sep. 2013, 8 pages.

International Preliminary Report on Patentability for Application No. PCT/US2012/029769, dated Sep. 24, 2013, 10 pages.

International Preliminary Report on Patentability for Application No. PCT/US2012/048229, dated Feb. 4. 2014, 7 pages.

International Preliminary Report on Patentability for Application No. PCT/US2013/023097, dated Jul. 29, 2014, 11 pages.

International Preliminary Report on Patentability for Application No. PCT/US2013/023182, dated Jul. 29, 2014, 8 pages.

International Preliminary Report on Patentability for Application No. PCT/US2013/023190, dated Jul. 29, 2014, 8 pages.

International Search Report and Written Opinion for Application No. PCT/US2013/023190, dated Apr. 15m 2013, 10 pages.

International Search Report for Application No. PCT/US2009/057284, dated May 4, 2010, 6 pages.

International Search Report for Application No. PCT/US2009/057289, dated Dec. 23, 2009, 3 pages.

International Search Report for Application No. PCT/US2012/023190, dated Apr. 15, 2013, 4 pages.

International Search Report for Application No. PCT/US2012/026849, dated Jul. 2, 2012, 5 pages.

International Search Report for Application No. PCT/US2012/029769, dated Oct. 2, 2012, 8 pages.

International Search Report for Application No. PCT/US2012/029796, dated Oct. 2, 2012, 4 pages.

(56) References Cited

OTHER PUBLICATIONS

International Search Report for Application No. PCT/US2012/048229, dated Nov. 21, 2012, 3 pages.
International Search Report for Application No. PCT/US2013/023005, dated Apr. 26, 2013, 4 pages.
International Search Report for Application No. PCT/US2013/023097, dated Aug. 7, 2013, 6 pages.
International Search Report for Application No. PCT/US2013/023182, dated Apr. 29, 2013, 4 pages.
Neudecker B.J., et al., "Power Fibers: Thin-Film Batteries on Fiber Substrates," Report Documented by ITN Energy Systems, Inc., Littleton, Co, 2003, pp. 1-9.
Oka Y., et al., "Preparation of Cathode Film With Use of Aqueous Solvent System," 224th ECS Meeting (Abstract #851), 2013, San Francisco, CA, USA.
Ostfeld A.E., et al., "Screen Printed Passive Components for Flexible Power Electronics," Scientific Reports, Oct. 2015, vol. 5, 12 pages.
Partial European Search Report for Application No. 18160035.4, dated Apr. 19, 2018, 17 pages.
Partial European Search Report for Application No. EP15181799.6, dated Feb. 29, 2016, 9 pages.
Partial European Search Report for Application No. EP15181865, dated Apr. 11, 2016, 7 pages.
Parviz B.A., "Augmented Reality in a Contact Lens," IEEE Spectrum, Sep. 2009. Retrieved from the Internet:[URL:https://spectrum.ieee.org/biomedical/bionics/augmented-reality-in-a-contact-lens].
Shi S., et al., "Flexible Asymmetric Supercapacitors Based on Ultrathin Two-dimensional Nanosheets With Outstanding Electrochemical Performance and Aesthetic Property Supplementary Information (SI)," Scientific Reports, Feb. 11, 2014, vol. 3, Article number: 2598, pp. 1-10, XP055485252, Retrieved from the Internet: URL: https://media.nature.com/original/nature-assets/srep/2013/130906/srep02598/extref/srep02598-s1.pdf.
Singapore Search Report for Application No. Sg-201300387-6, dated Jul. 4, 2013.
Singapore Written Opinion for Application No. SG11201404171Y, dated Mar. 31, 2015.
Stani A., et al. "Development of Flat Plate Rechargeable Alkaline Manganese Dioxide-Zinc Cells," Journal of Power Sources, Feb. 2006, vol. 153 (2), pp. 405-412.
Tafur, J.P., et al., "Influence of the Ionic Liquid Type on the Gel Polymer Electrolytes Properties," Membranes (Basel), Dec. 2015, vol. 5(4), pp. 752-771.
Written opinion for Application No. PCT/US2009/057284, dated May 4, 2010, 9 pages.
Written Opinion for Application No. PCT/US2009/057289, dated Mar. 22, 2011, 5 pages.
Written Opinion for Application No. PCT/US2012/026849, dated Aug. 13, 2013, 7 pages.
Written Opinion for Application No. PCT/US2012/029769, dated Sep. 21, 2013, 9 pages.
Written Opinion for Application No. PCT/US2012/048229, dated Feb. 2, 2014, 6 pages.
Written Opinion for Application No. PCT/US2013/023005, dated Jul. 26, 2014, 7 pages.
Written Opinion for Application No. PCT/US2013/023097, dated Jul. 26, 2014, 10 pages.
Written Opinion for Application No. PCT/US2013/023182, dated Jul. 26, 2014, 7 pages.
Yanez F., et al., "Macromolecule Release and Smoothness of Semi-Interpenetrating PVP-pHEMA Networks for Comfortable Soft Contact Lenses," European Journal of Pharmaceutics, Aug. 2008, vol. 69 (3), pp. 1094-1103.
Jani Miettinen et al., "System Design Issue for 3D System-in-Package (SiP)", 2004, vol. 1, p. 610-615.

FIG. 1A
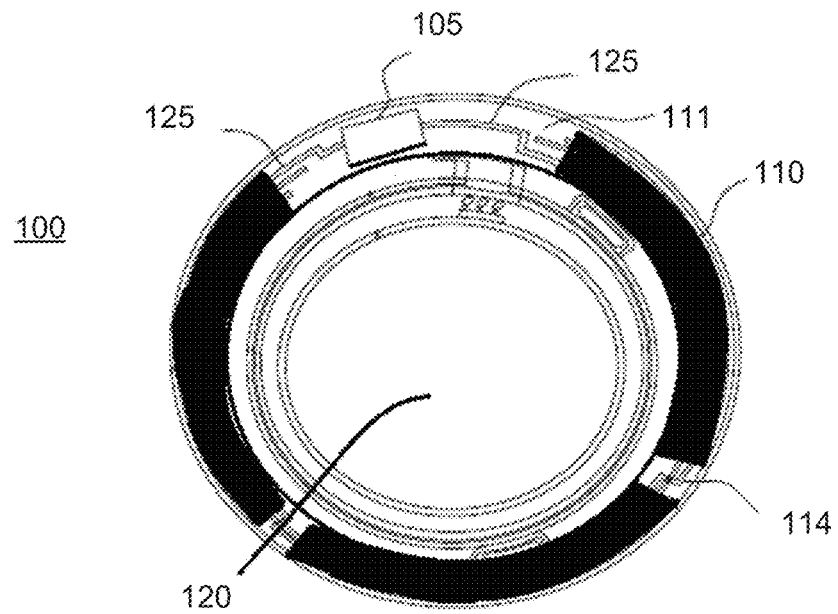
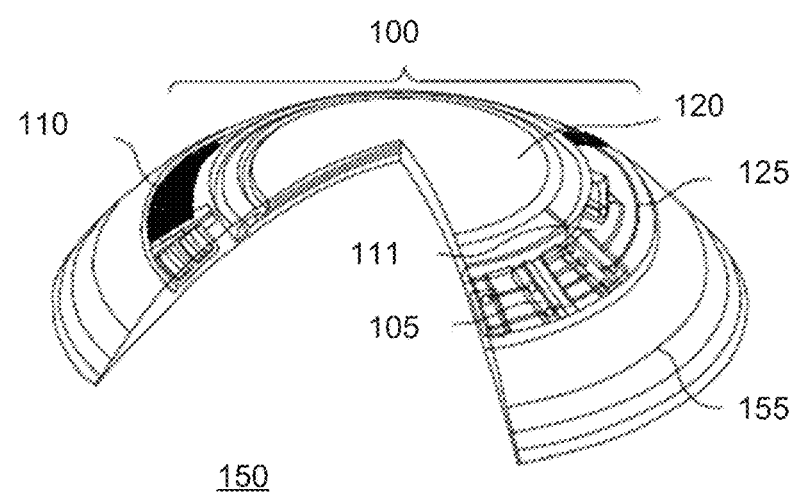
FIG. 1B

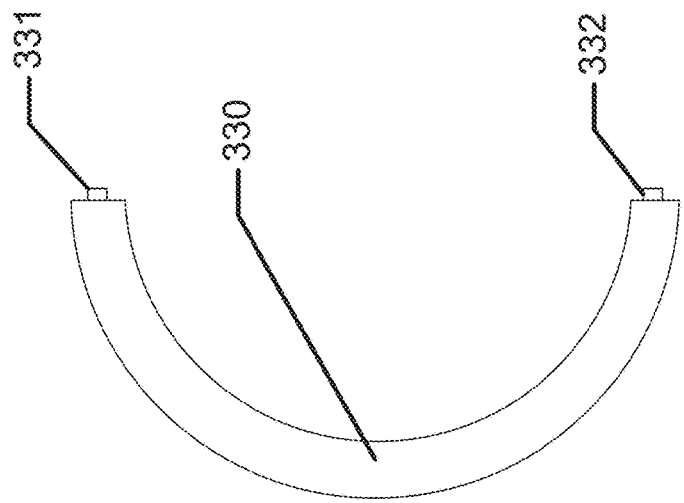
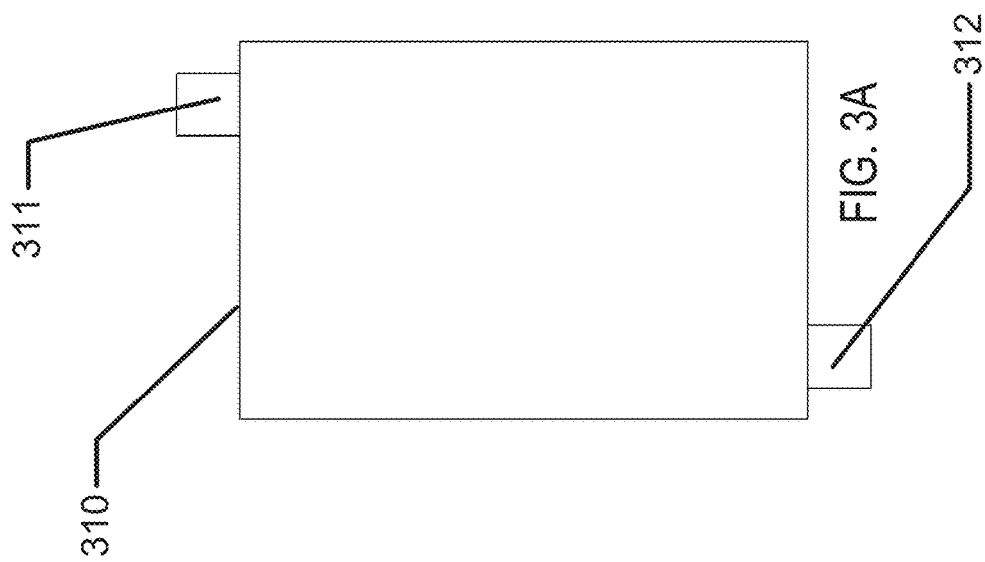

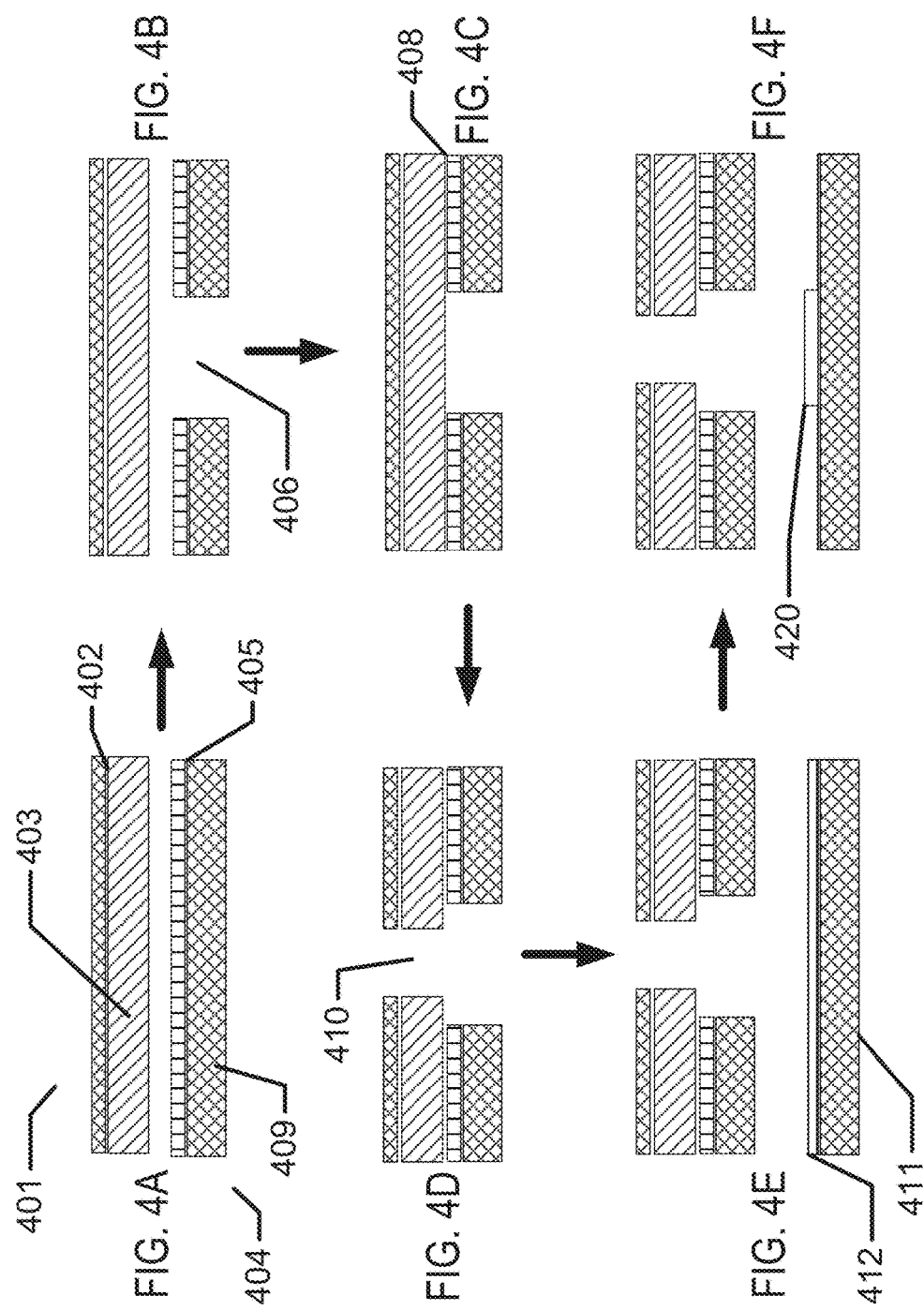

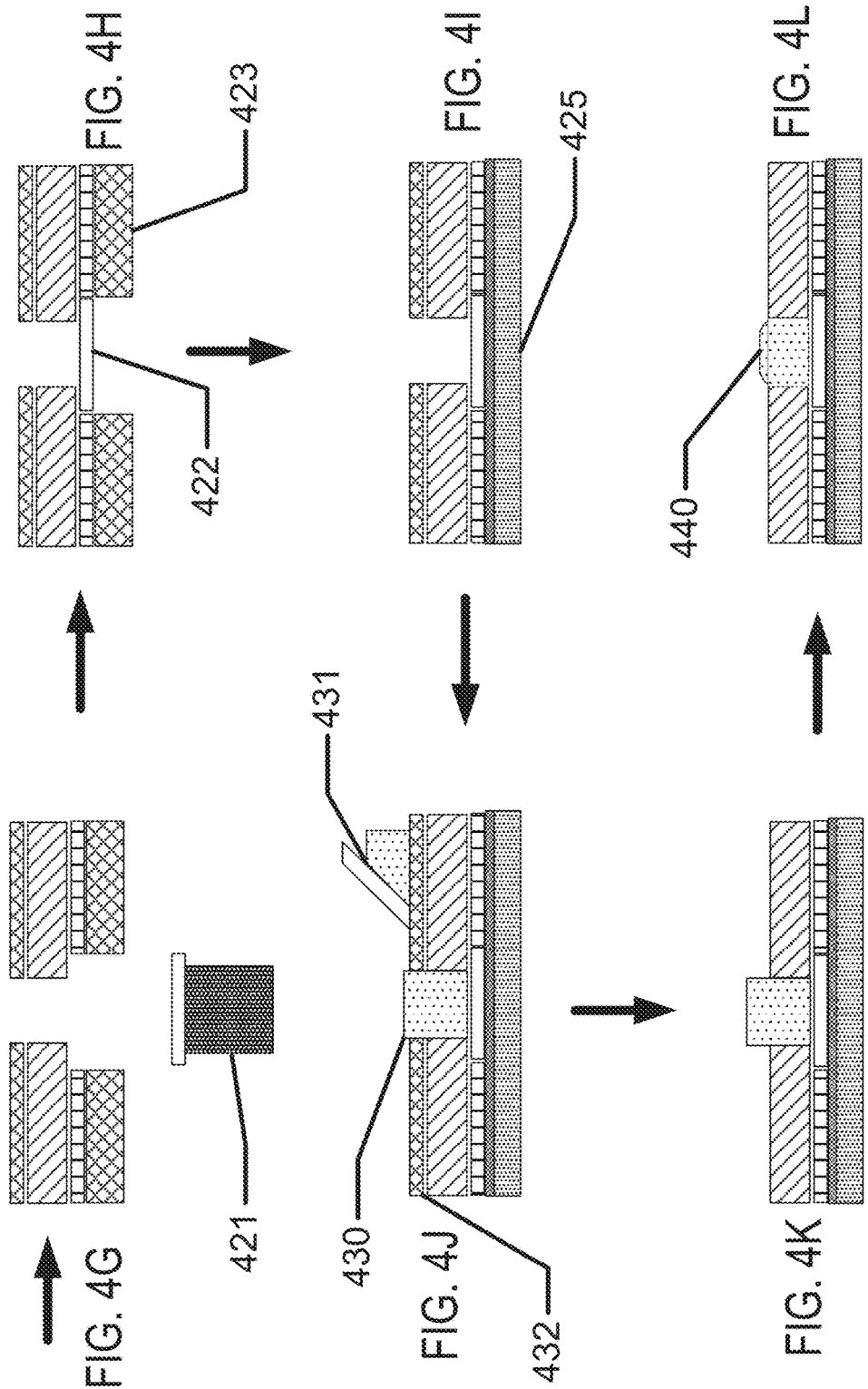

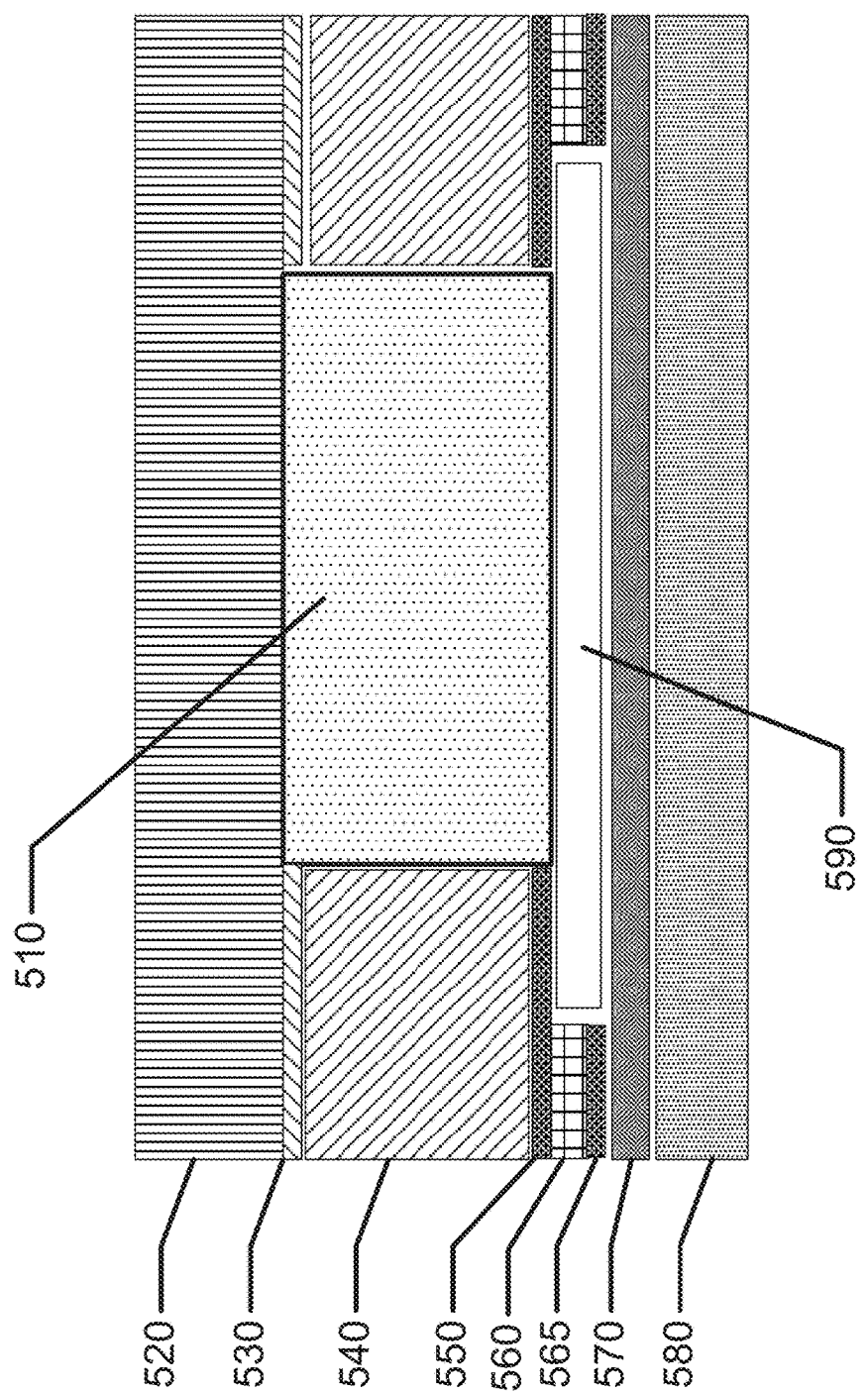

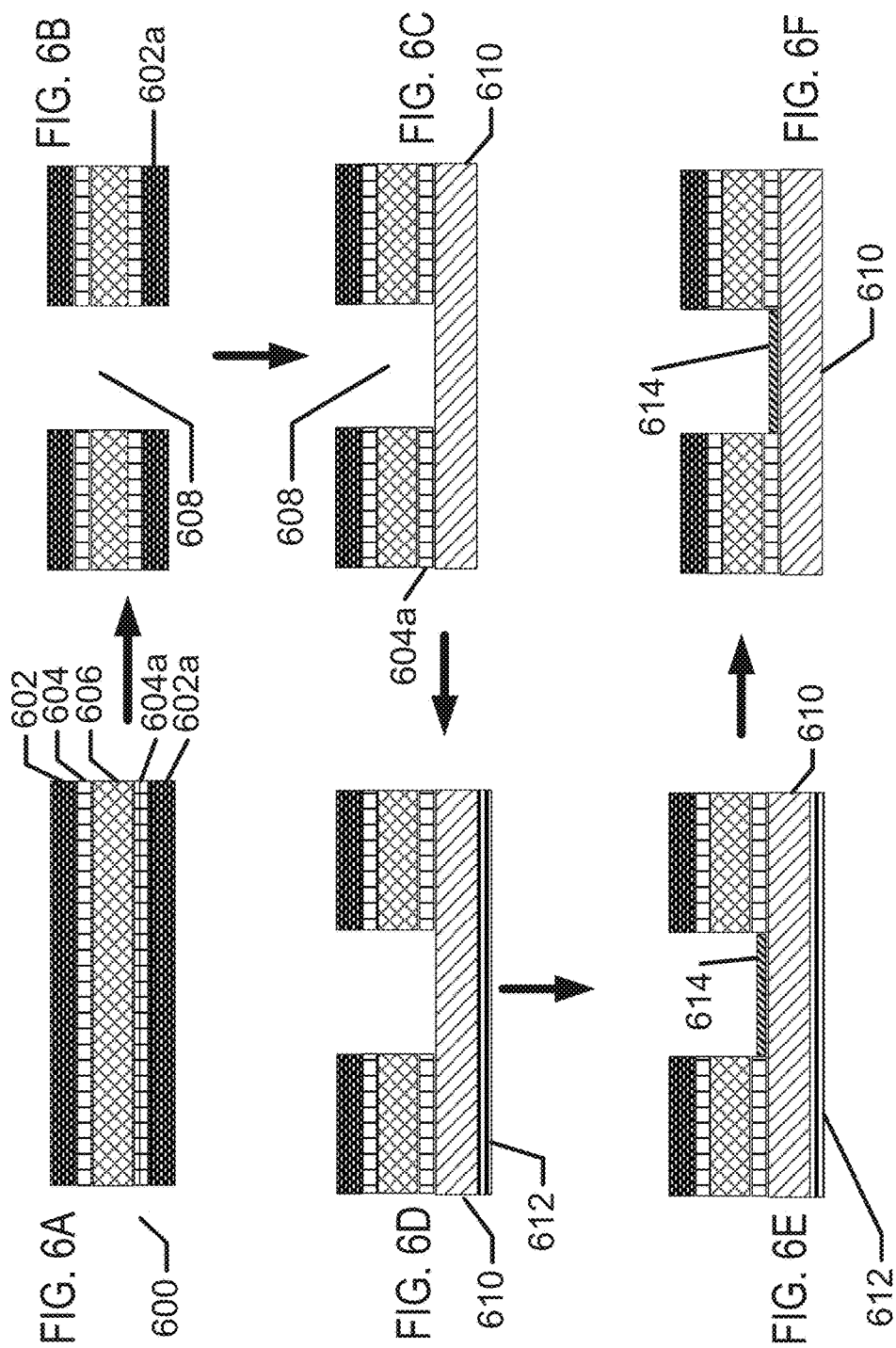

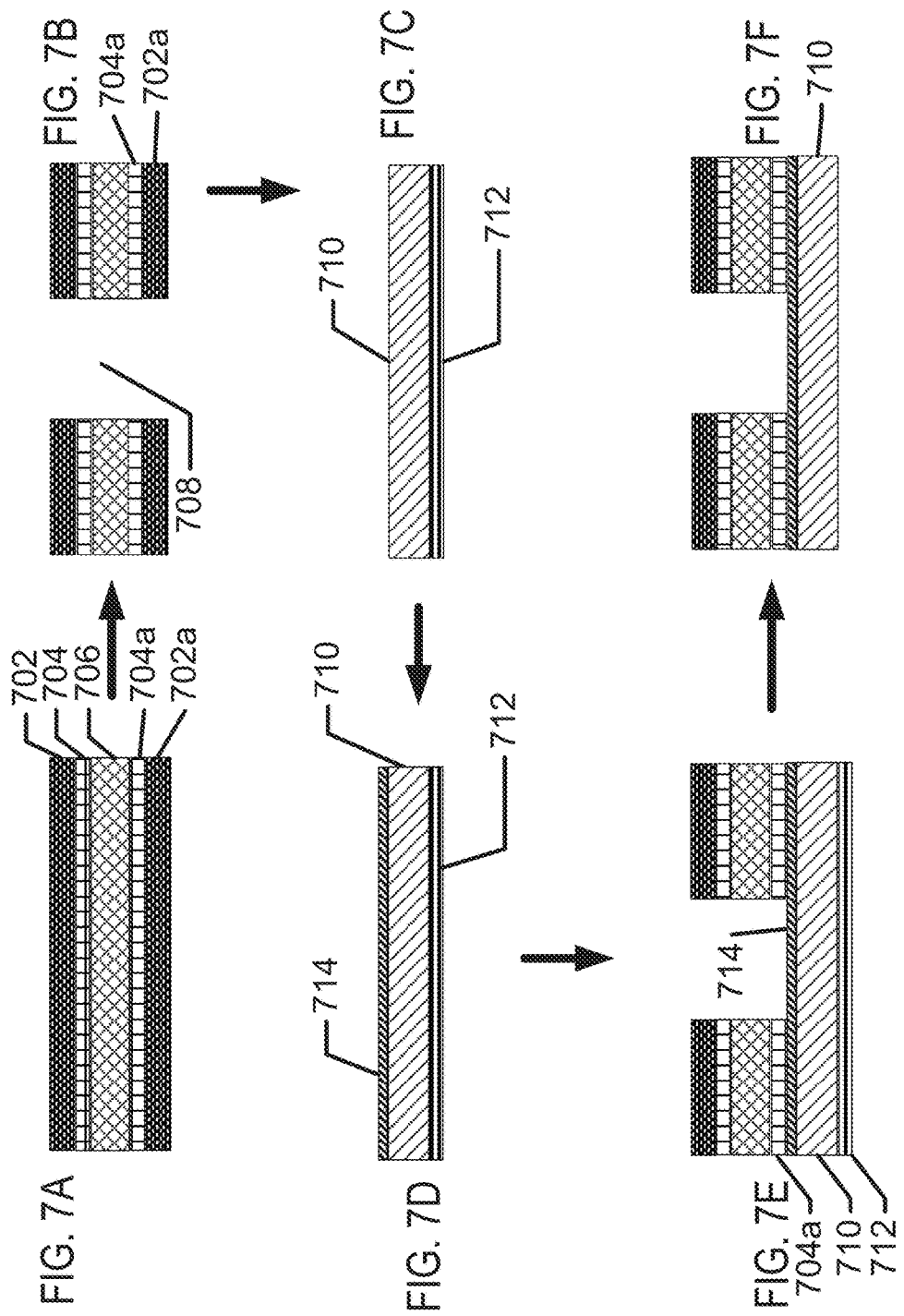

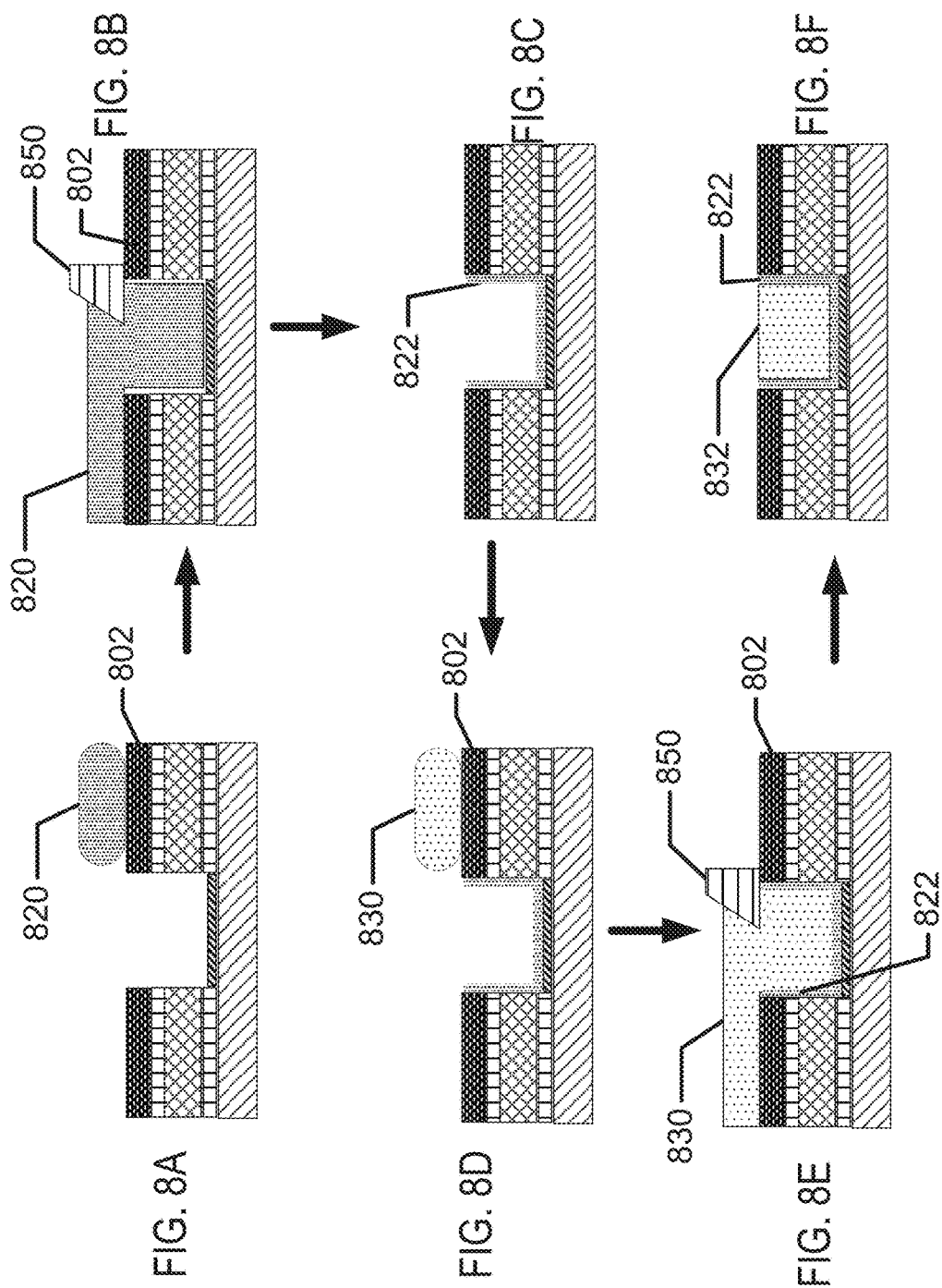

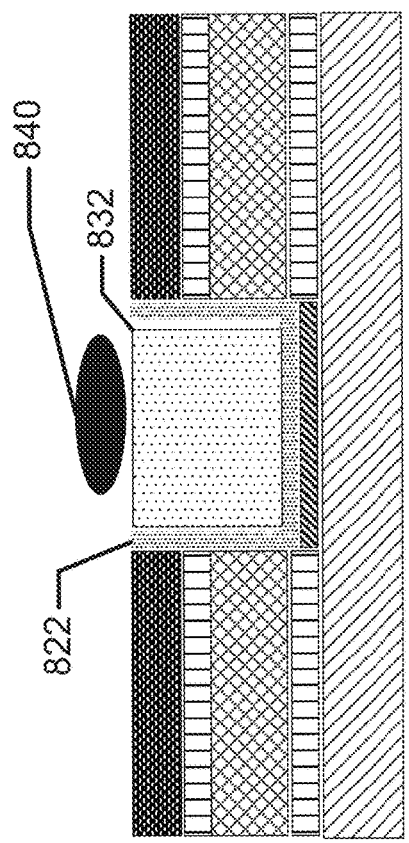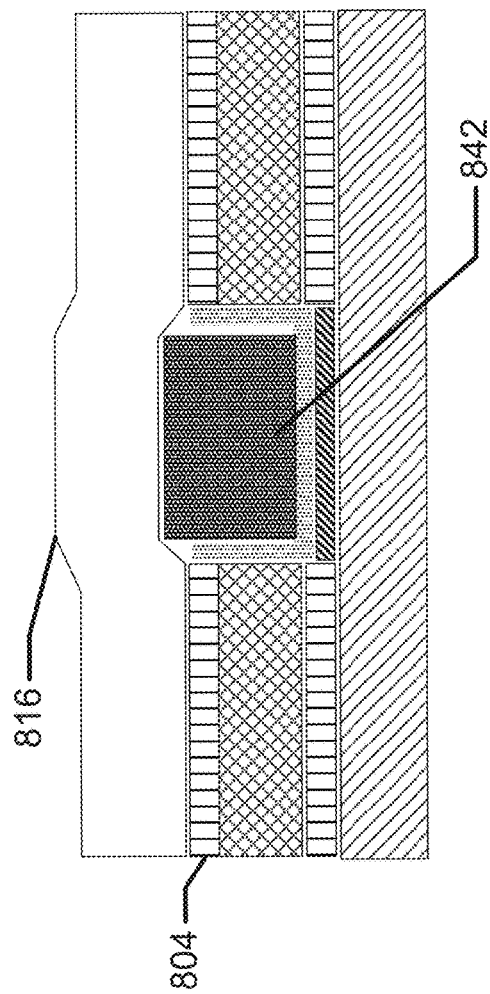

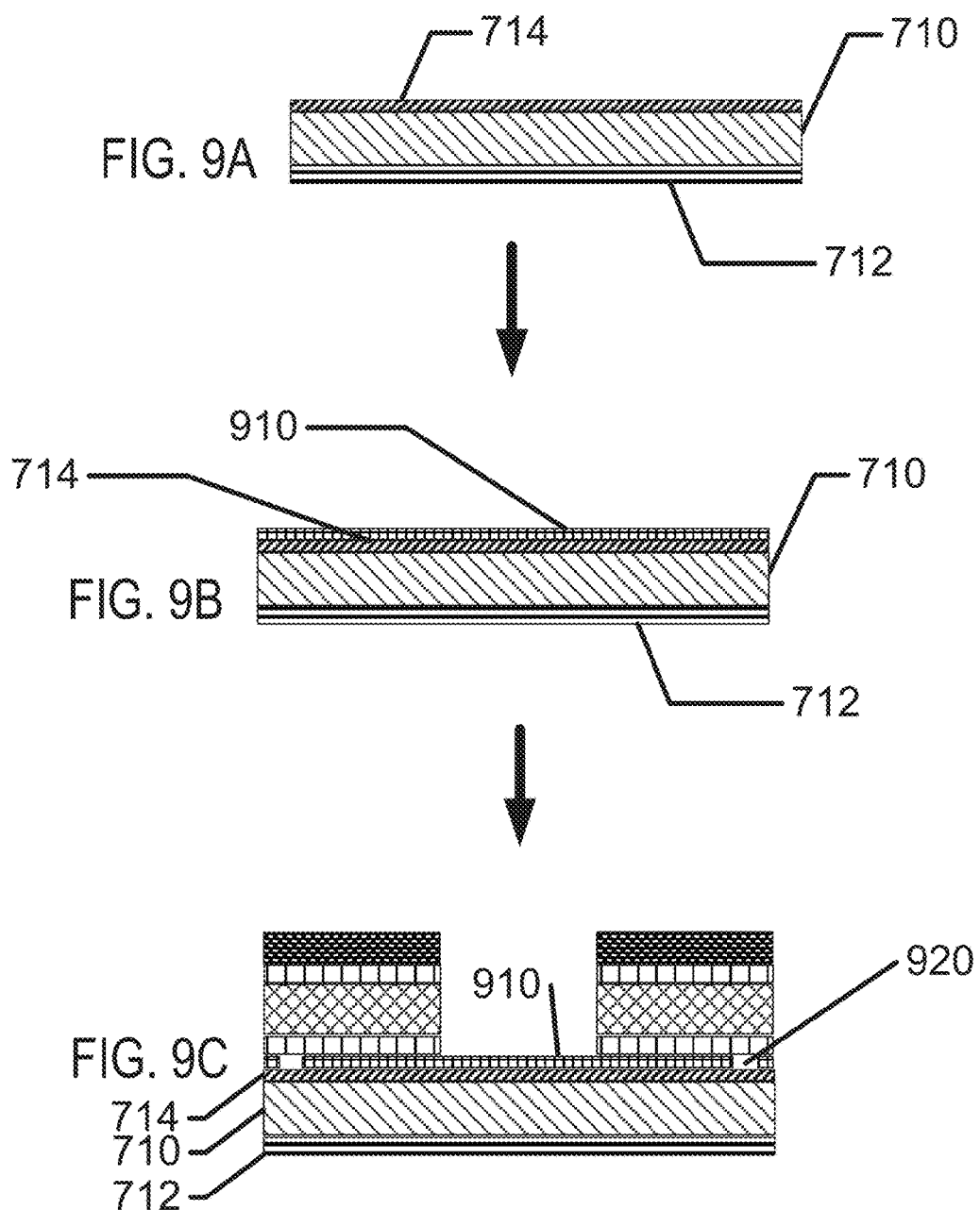

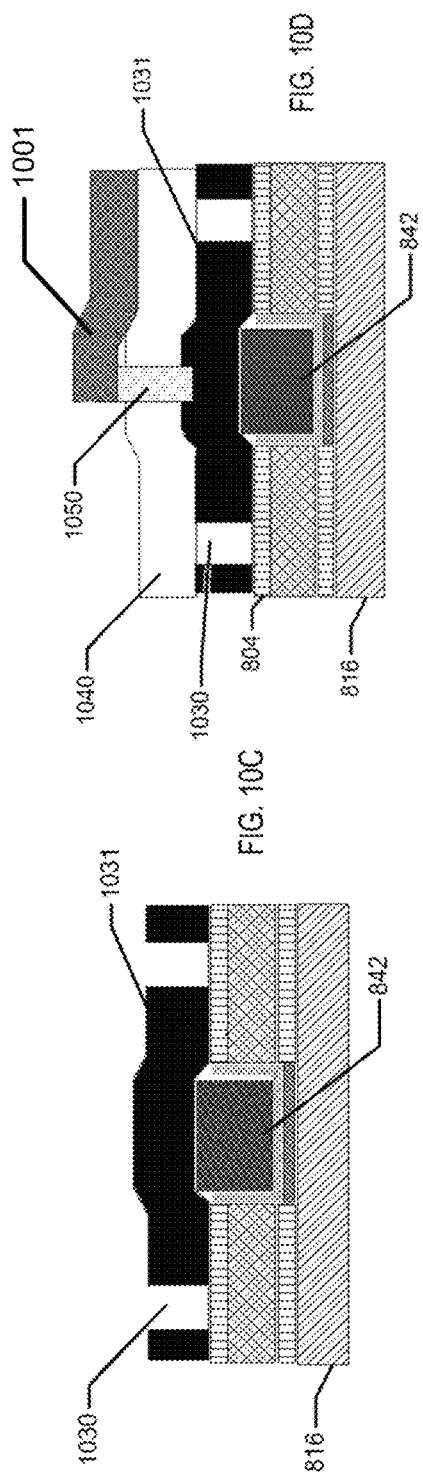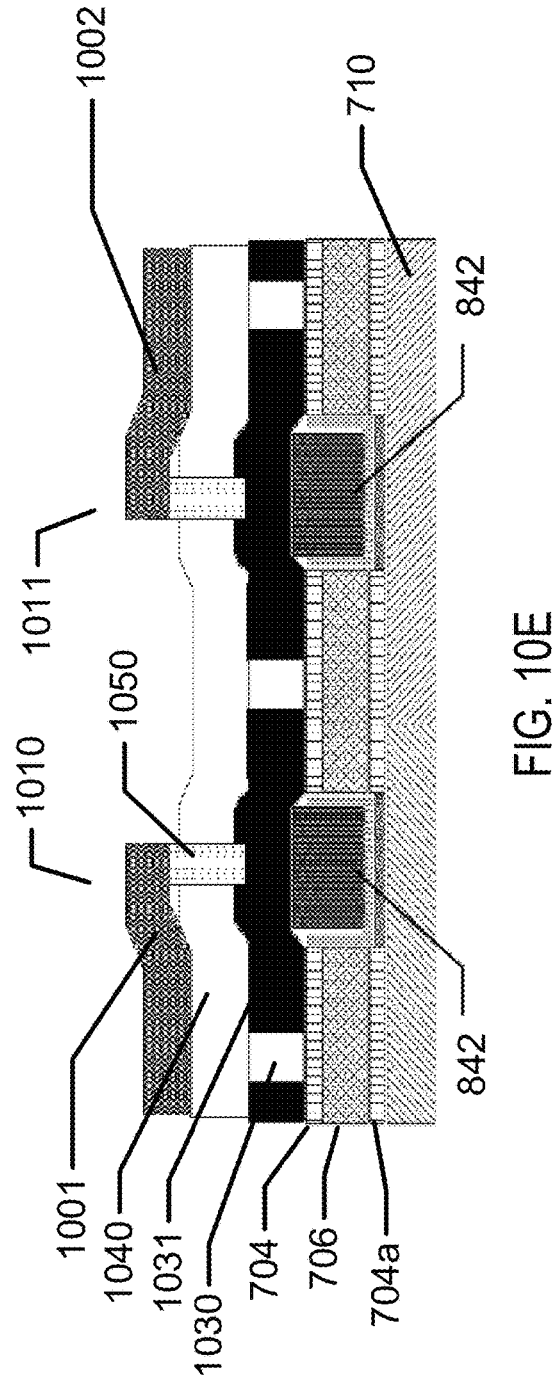

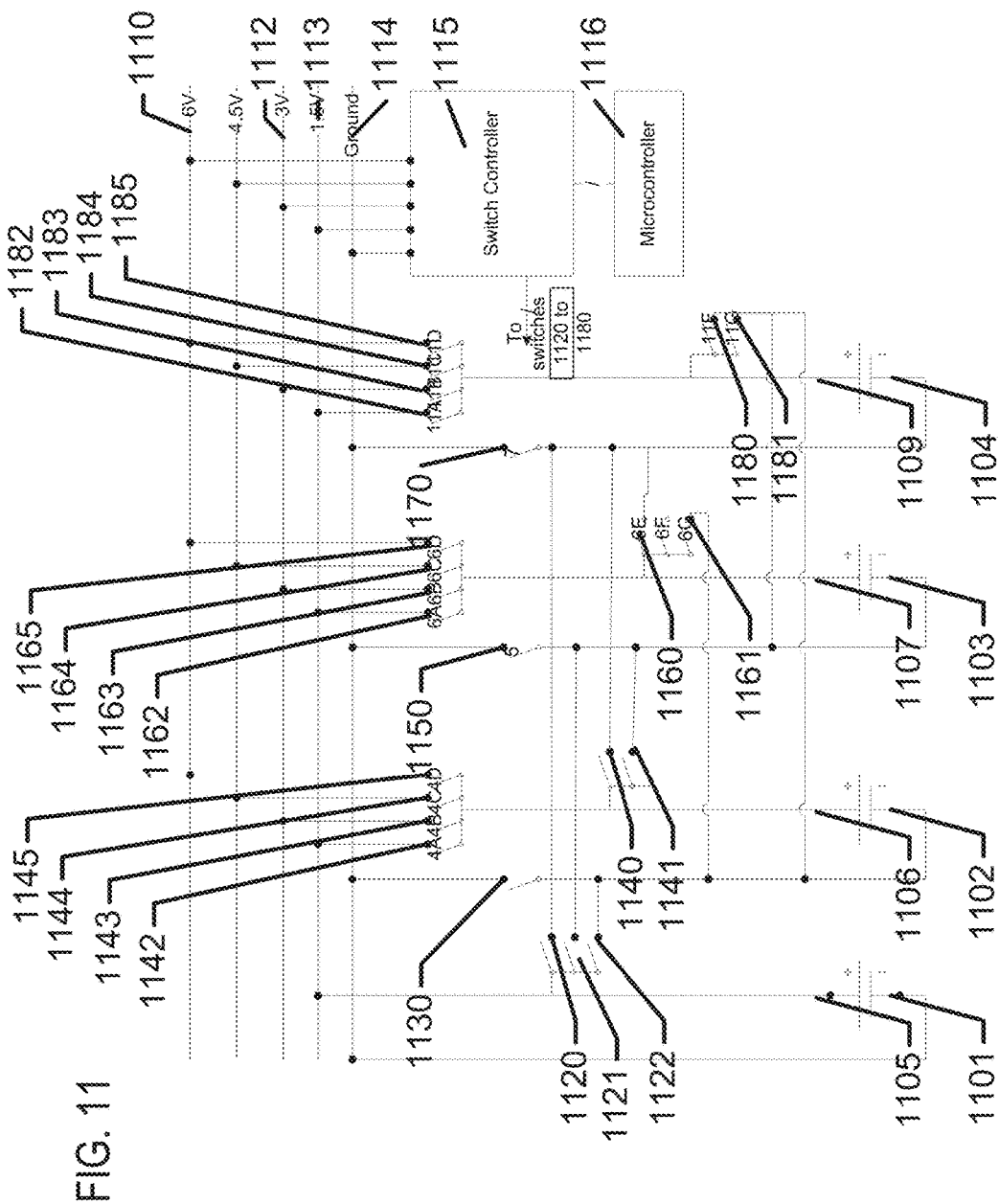

COMPONENTS WITH MULTIPLE ENERGIZATION ELEMENTS FOR BIOMEDICAL DEVICES

CROSS REFERENCE TO RELATED APPLICATIONS

This application claims the benefit of U.S. Provisional Application No. 62/040,178 filed Aug. 21, 2014, and is a continuation-in-part of U.S. application Ser. No. 13/358,916, filed Jan. 26, 2012 (now U.S. Pat. No. 9,110,310), which claims the benefit of U.S. Provisional Application No. 61/454,205, filed Mar. 18, 2011.

BACKGROUND OF THE INVENTION

1. Field of the Invention

Methods and apparatus to form biocompatible energization elements are described. In some embodiments, the methods and apparatus to form the biocompatible energization elements involve forming a separator element of the energization element. The active elements including anodes, cathodes and electrolytes may be electrochemically connected and may interact with the formed separator elements. In some embodiments, a field of use for the methods and apparatus may include any biocompatible device or product that requires energization elements.

2. Discussion of the Related Art

Recently, the number of medical devices and their functionality has begun to rapidly develop. These medical devices can include, for example, implantable pacemakers, electronic pills for monitoring and/or testing a biological function, surgical devices with active components, contact lenses, infusion pumps, and neurostimulators. Added functionality and an increase in performance to the many of the aforementioned medical devices has been theorized and developed. However, to achieve the theorized added functionality, many of these devices now require self-contained energization means that are compatible with the size and shape requirements of these devices, as well as the energy requirements of the new energized components.

Some medical devices may include components such as semiconductor devices that perform a variety of functions and can be incorporated into many biocompatible and/or implantable devices. However, such semiconductor components require energy and, thus, energization elements should preferably also be included in such biocompatible devices. The topology and relatively small size of the biocompatible devices creates novel and challenging environments for the definition of various functionalities. In many embodiments, it is important to provide safe, reliable, compact and cost effective means to energize the semiconductor components within the biocompatible devices. Therefore, a need exists for novel embodiments of forming biocompatible energization elements for implantation within or upon biocompatible devices where the structure of the battery elements provides enhanced containment for chemical components of the energization elements as well as improved control over the quantity of chemical components contained in the energization element.

SUMMARY OF THE INVENTION

Accordingly, methods and apparatus to form biocompatible energization elements are disclosed which afford manufacturing advantages while creating structures which may significantly contain the battery chemistry. As well, the structural design may also provide for inherent control of the quantities of the energization elements found within the battery elements.

One general aspect includes a biocompatible energization element which may also include a gap spacer layer. The biocompatible energization element may also include at least a first hole located in the gap spacer layer. The biocompatible energization element may also include a cathode spacer layer, where the cathode spacer layer is attached to the gap spacer layer. The biocompatible energization element may also include at least a second hole located in the cathode spacer layer, where the second hole is aligned to the first hole, and where the second hole is smaller than the first hole such that when the first hole and the second hole are aligned there is a ridge of cathode spacer layer exposed in the first hole. The biocompatible energization element may also include a separator layer, where the separator layer is placed within the first hole in the gap spacer layer and is adhered to the ridge of cathode spacer layer. The biocompatible energization element may also include a cavity between sides of the second hole and a first surface of the separator layer, where the cavity is filled with cathode chemicals. The biocompatible energization element may also include a first current collector coated with anode chemicals. The biocompatible energization element may also include a second current collector, where the second current collector is in electrical connection with the cathode chemicals. The biocompatible energization element may also include an electrolyte including electrolyte chemicals.

Implementations may include the biocompatible energization element where the cathode chemicals, anode chemicals and electrolyte chemicals are consistent with multiple charging and discharging cycles of the energization The biocompatible energization element may also include examples where the cathode chemicals include a salt of lithium. The biocompatible energization element may include lithium iron phosphate. The biocompatible energization element may also include intercalated metal atoms. The biocompatible energization element may also include intercalated lithium atoms. The biocompatible energization element may also include one or more of lead, nickel, lithium, cobalt, zinc, sodium, vanadium, silver, or silicon. The biocompatible energization element may also include sodium carboxymethyl cellulose. The biocompatible energization element may also include examples where the cathode chemicals include one or more of synthetic graphite and carbon black. The biocompatible energization element may also include examples where the cathode chemicals include one or more of styrene butadiene rubber. The biocompatible energization element may also include lithium hexafluorophosate. The biocompatible energization element may include examples where the biocompatible energization element is electrically connected to an electroactive element within a biomedical device. The biocompatible energization element may also include examples where the biomedical device is an ophthalmic device. In some examples the ophthalmic device may be a contact lens.

The biocompatible energization element may also include examples where the electrolyte includes lithium hexafluorophosphate. The biocompatible energization element may also include examples where the separator precursor mixture includes one or more of poly(vinylidene fluoride), poly(dimethylsiloxane), n-n dimethyl acetamide). Additional examples may also include glycerol. The biocompatible energization element may also include the biocompatible energization element where the separator includes glycerol in a concentration at least 90 percent and the concentration may be reduced from a concentration of glycerol in the separator precursor mixture. The biocompatible energization element may be included within a biomedical device.

One general aspect includes the biocompatible energization element which may be included into an ophthalmic device where the ophthalmic device is a contact lens. The biocompatible energization element may also include a biocompatible energization element including a cathode spacer layer; at least a first hole located in the cathode spacer layer; a first current collector coated with anode chemicals, where the first current collector is attached to a first surface of the cathode spacer layer, and where a first cavity is created between sides of the first hole and a first surface of the first current collector coated with anode chemicals; a separator layer, where the separator layer is formed within the first cavity after a separator precursor mixture is dispensed into the cavity; a second cavity between sides of the first hole and a first surface of the separator layer, where the second cavity is filled with cathode chemicals; a second current collector, where the second current collector is in electrical connection with the cathode chemicals; and an electrolyte. Implementations may include biocompatible energization elements where the cathode chemicals, anode chemicals and electrolyte chemicals are consistent with multiple charging and discharging cycles of the energization element.

One general aspect includes a method of operating a biomedical device, the method including: obtaining a laminate battery device with multiple energization elements for an biomedical device including powered components. The laminate battery device includes a cathode spacer layer, a first hole located in the cathode spacer layer, and a first current collector coated with anode chemicals, where the first current collector is attached to a first surface of the cathode spacer layer. The laminate battery device may include examples where a first cavity is created between sides of the first hole and a first surface of the first current collector coated with anode chemicals. The laminate battery device also includes a separator layer, where the separator layer is formed within the first cavity after a separator precursor mixture is dispensed into the cavity. The method also includes a second cavity between sides of the first hole and a first surface of the separator layer, where the second cavity is filled with cathode chemicals. The method also includes the laminate battery device which includes a second current collector, where the second current collector is in electrical connection with the cathode chemicals. The method also includes an electrolyte including electrolyte chemicals. The method of also includes placing the laminate battery device into electrical contact with powered components, where electrical current from the laminate battery device flows through at least one electrical transistor, where the at least one electrical transistor is located within a controller; where at least a first and a second discrete energization element are located within the laminate battery device, where the first discrete energization element generates a first raw battery power and the second discrete energization element generates a second raw battery power; and where a power management unit is electrically connected to the first and the second discrete energization elements. In some examples, the power management unit receives the first raw battery power from the first discrete energization element and the second raw battery power from the second discrete energization element.

The method may further include utilizing the second measurement to determine a defectiveness of the second discrete energization element. The method may also include an example where the determination is that the second discrete energization element is not defective, and in that case the switch controller controls a change of state of a second switch connecting to the second discrete energization element. The method may also include examples where the change of state of the second switch connects the second discrete energization element to the first power output.

One general aspect includes an apparatus for powering a biomedical device; the apparatus may include a laminate battery device with multiple energization elements for a biomedical device including powered components. The apparatus may include a cathode spacer layer and a first hole located in the cathode spacer layer. The apparatus also includes a first current collector coated with anode chemicals, where the first current collector is attached to a first surface of the cathode spacer layer, and where a first cavity is created between sides of the first hole and a first surface of the first current collector coated with anode chemicals. The apparatus also includes a separator layer, where the separator layer is formed within the first cavity after a separator precursor mixture is dispensed into the cavity. The apparatus also includes a second cavity between sides of the first hole and a first surface of the separator layer, where the second cavity is filled with cathode chemicals. The apparatus also includes a second current collector, where the second current collector is in electrical connection with the cathode chemicals. The apparatus also includes a third current collector, where the third current collector is physically segmented from the second current collector and is in electrical connection with the cathode chemicals within a second hole located in the cathode spacer layer; and an interconnect junction element, where the interconnection junction element makes electrical connection to the first current collector, the second current collector and the third current collector, where an electrical diode within the interconnect junction element makes connection to at least one of the first current collector, the second current collector and the third current collector.

BRIEF DESCRIPTION OF THE DRAWINGS

FIGS. 1A-1D illustrate exemplary aspects of biocompatible energization elements in concert with the exemplary application of contact lenses.

FIG. 3A illustrates a first stand-alone, packaged biocompatible energization element with exemplary anode and cathode connections.

FIG. 3B illustrates a second stand-alone, packaged biocompatible energization element with exemplary anode and cathode connections.

FIGS. 4A-4N illustrate exemplary method steps for the formation of biocompatible energization elements for biomedical devices.

FIG. 5 illustrates an exemplary fully formed biocompatible energization element.

FIGS. 6A-6F illustrate exemplary method steps for structural formation of biocompatible energization elements.

FIGS. 7A-7F illustrate exemplary method steps for structural formation of biocompatible energization elements with alternate electroplating method.

FIGS. 8A-8H illustrate exemplary method steps for the formation of biocompatible energization elements with hydrogel separator for biomedical devices.

FIGS. 9A-C illustrate exemplary methods steps for structural formation of biocompatible energization elements utilizing an alternative separator processing embodiments.

FIGS. 10C through 10E illustrate exemplary cross section depictions of the examples of FIGS. 10A and 10B.

FIG. 11 illustrates an exemplary switching system that may be used to create multiple power outputs with multiple energization element devices.

DETAILED DESCRIPTION OF THE INVENTION

Figure 1C:
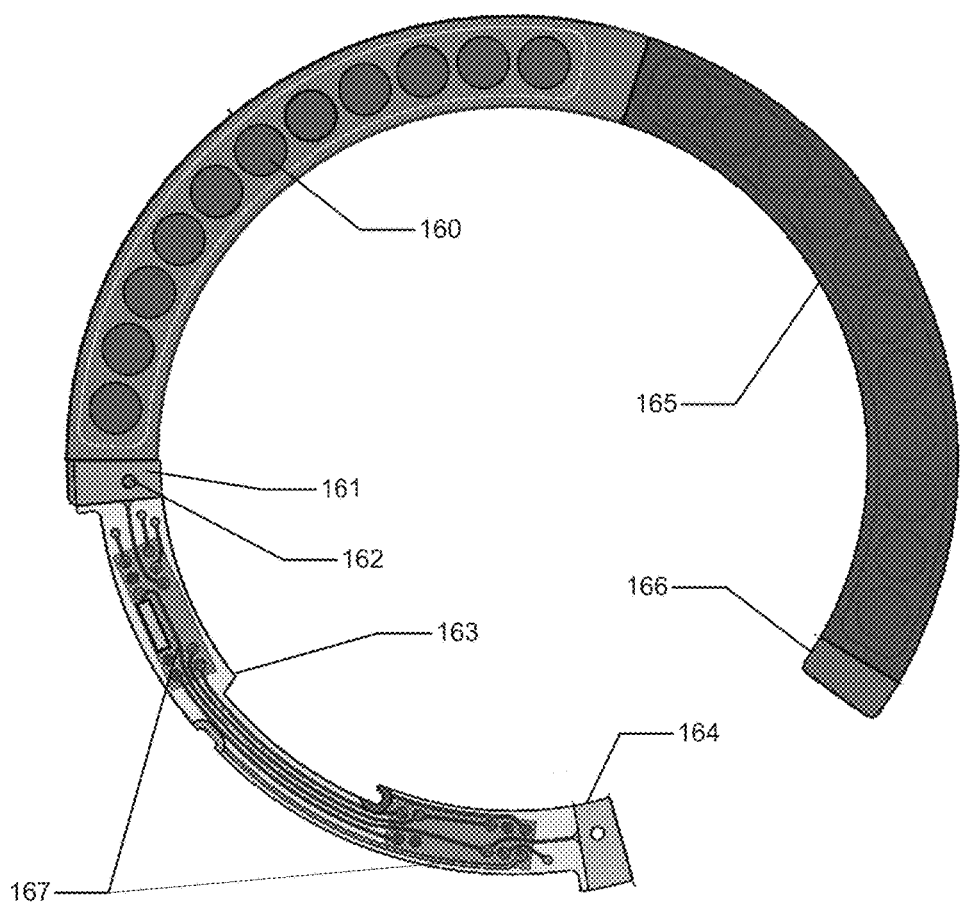

Methods and apparatus to form three-dimensional biocompatible energization elements are disclosed in this application. The separator element within the energization elements may be formed with novel methods and may comprise novel materials. In the following sections, detailed descriptions of various embodiments are described. The description of both preferred and alternative embodiments are exemplary embodiments only, and various modifications and alterations may be apparent to those skilled in the art. Therefore, the exemplary embodiments do not limit the scope of this application. The three-dimensional biocompatible energization elements are designed for use in or proximate to the body of a living organism.

Glossary

In the description and claims below, various terms may be used for which the following definitions will apply:

"Anode" as used herein refers to an electrode through which electric current flows into a polarized electrical device. The direction of electric current is typically opposite to the direction of electron flow. In other words, the electrons flow from the anode into, for example, an electrical circuit.

"Binder" as used herein refers to a polymer that is capable of exhibiting elastic responses to mechanical deformations and that is chemically compatible with other energization element components. For example, binders may include electroactive materials, electrolytes, polymers, etc.

"Biocompatible" as used herein refers to a material or device that performs with an appropriate host response in a specific application. For example, a biocompatible device does not have toxic or injurious effects on biological systems.

"Cathode" as used herein refers to an electrode through which electric current flows out of a polarized electrical device. The direction of electric current is typically opposite to the direction of electron flow. Therefore, the electrons flow into the cathode of the polarized electrical device, and out of, for example, the connected electrical circuit.

"Coating" as used herein refers to a deposit of material in thin forms. In some uses, the term will refer to a thin deposit that substantially covers the surface of a substrate it is formed upon. In other more specialized uses, the term may be used to describe small thin deposits in smaller regions of the surface.

"Electrode" as used herein may refer to an active mass in the energy source. For example, it may include one or both of the anode and cathode.

"Energized" as used herein refers to the state of being able to supply electrical current or to have electrical energy stored within.

"Energy" as used herein refers to the capacity of a physical system to do work. Many uses of the energization elements may relate to the capacity of being able to perform electrical actions.

"Energy Source" or "Energization Element" or "Energization Device" as used herein refers to any device or layer which is capable of supplying energy or placing a logical or electrical device in an energized state. The energization elements may include batteries. The batteries may be formed from alkaline type cell chemistry and may be solid-state batteries or wet cell batteries.

"Fillers" as used herein refer to one or more energization element separators that do not react with either acid or alkaline electrolytes. Generally, fillers may include substantially water insoluble materials such as carbon black; coal dust; graphite; metal oxides and hydroxides such as those of silicon, aluminum, calcium, magnesium, barium, titanium, iron, zinc, and tin; metal carbonates such as those of calcium and magnesium; minerals such as mica, montmorollonite, kaolinite, attapulgite, and talc; synthetic and natural zeolites such as Portland cement; precipitated metal silicates such as calcium silicate; hollow or solid polymer or glass microspheres, flakes and fibers; etc.

"Functionalized" as used herein refers to making a layer or device able to perform a function including, for example, energization, activation, and/or control.

"Mold" as used herein refers to a rigid or semi-rigid object that may be used to form three-dimensional objects from uncured formulations. Some exemplary molds include two mold parts that, when opposed to one another, define the structure of a three-dimensional object.

"Power" as used herein refers to work done or energy transferred per unit of time.

"Rechargeable" or "Re-energizable" as used herein refer to a capability of being restored to a state with higher capacity to do work. Many uses may relate to the capability of being restored with the ability to flow electrical current at a certain rate for certain, reestablished time periods.

"Reenergize" or "Recharge" as used herein refer to restoring to a state with higher capacity to do work. Many uses may relate to restoring a device to the capability to flow electrical current at a certain rate for a certain reestablished time period.

"Released" as used herein and sometimes referred to as "released from a mold" means that a three-dimensional object is either completely separated from the mold, or is only loosely attached to the mold, so that it may be removed with mild agitation.

"Stacked" as used herein means to place at least two component layers in proximity to each other such that at least a portion of one surface of one of the layers contacts a first surface of a second layer. In some examples, a coating, whether for adhesion or other functions, may reside between the two layers that are in contact with each other through said coating.

"Traces" as used herein refer to energization element components capable of connecting together the circuit components. For example, circuit traces may include copper or gold when the substrate is a printed circuit board and may typically be copper, gold or printed film in a flexible circuit. A special type of "Trace" is the current collector. Current collectors are traces with electrochemical compatibility that make the current collectors suitable for use in conducting electrons to and from an anode or cathode in the presence of electrolyte.

The methods and apparatus presented herein relate to forming biocompatible energization elements for inclusion within or on flat or three-dimensional biocompatible devices. A particular class of energization elements may be batteries that are fabricated in layers. The layers may also be classified as laminate layers. A battery formed in this manner may be classified as a laminar battery.

There may be other examples of how to assemble and configure batteries according to the present invention, and some may be described in following sections. However, for many of these examples, there are selected parameters and characteristics of the batteries that may be described in their own right. In the following sections, some characteristics and parameters will be focused upon.

Exemplary Biomedical Device Construction with Biocompatible Energization Elements An example of a biomedical device that may incorporate the Energization Elements, batteries, of the present invention may be an electroactive focal-adjusting contact lens. Referring to FIG. 1A, an example of such a contact lens insert is depicted as contact lens insert 100. In the contact lens insert 100, there may be an electroactive element 120 that may accommodate focal characteristic changes in response to controlling voltages. A circuit 105, to provide those controlling voltage signals as well as to provide other functions such as controlling sensing of the environment for external control signals, may be powered by a biocompatible battery element 110. As depicted in FIG. 1A, the battery element 110 may be found as multiple major pieces, in this case three pieces, and may include the various configurations of battery chemistry elements as has been discussed. The battery elements 110 may have various interconnect features to join together pieces as may be depicted underlying the region of interconnect 114. The battery elements 110 may be connected to a circuit element that may have its own substrate 111 upon which interconnect features 125 may be located. The circuit 105, which may be in the form of an integrated circuit, may be electrically and physically connected to the substrate 111 and its interconnect features 125.

Referring to FIG. 1B, a cross sectional relief of a contact lens 150 may comprise contact lens insert 100 and its discussed constituents. The contact lens insert 100 may be encapsulated into a skirt of contact lens hydrogel 155 which may encapsulate the contact lens insert 100 and provide a comfortable interface of the contact lens 150 to a user's eye.

Figure 1D:
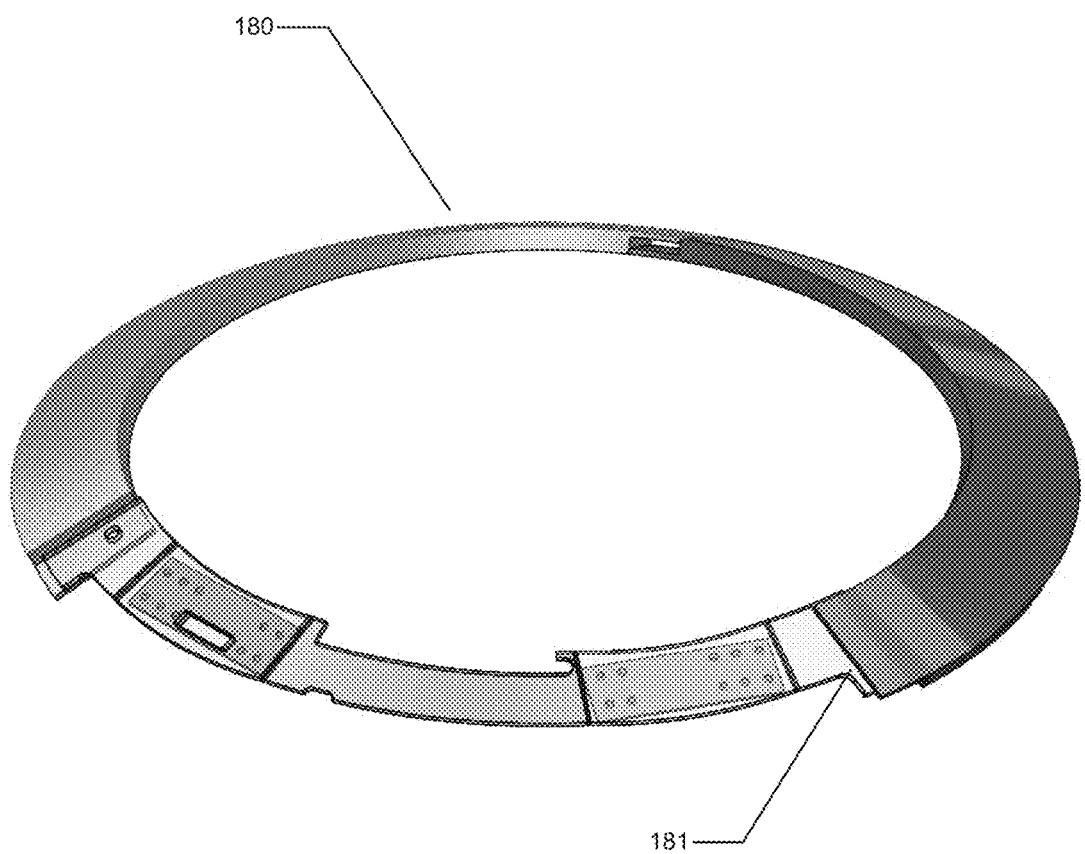

In reference to concepts of the present invention, the battery elements may be formed in a two-dimensional form as depicted in FIG. 1C. In this depiction there may be two main regions of battery cells in the regions of battery component 165 and the second battery component in the region of battery chemistry element 160. The battery elements, which are depicted in flat form in FIG. 1C, may connect to a circuit element 163, which in the example of FIG. 1C may comprise two major circuit areas 167. The circuit element 163 may connect to the battery element at an electrical contact 161 and a physical contact 162. The flat structure may be folded into a three-dimensional conical structure as has been described with respect to the present invention. In that process a second electrical contact 166 and a second physical contact 164 may be used to connect and physically stabilize the three-dimensional structure. Referring to FIG. 1D, a representation of this three-dimensional conical structure 180 is illustrated. The physical and electrical contact points 181 may also be found and the illustration may be viewed as a three-dimensional view of the resulting structure. This structure may include the modular electrical and battery component that will be incorporated with a lens insert into a biocompatible device.

Segmented Battery Schemes

Figure 2:
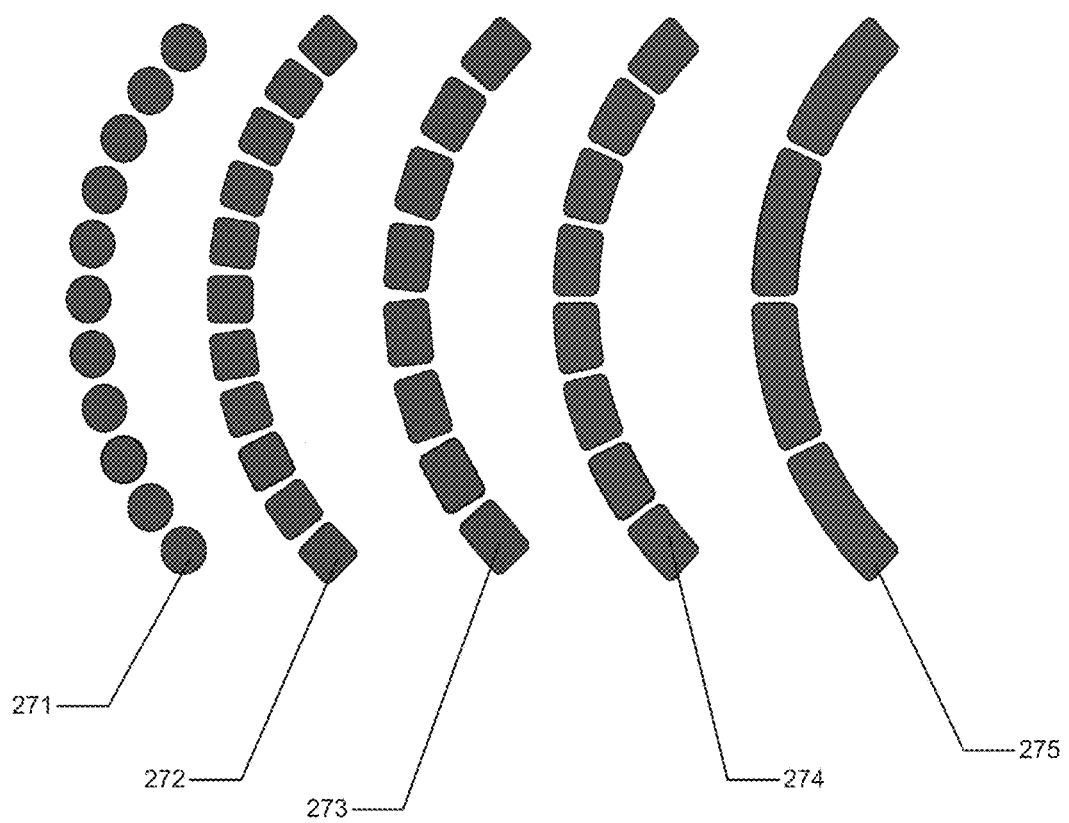
FIG. 2 illustrates the exemplary size and shape of individual cells of an exemplary battery design.

Referring to FIG. 2, an example of different types of segmented battery schemes is depicted for an exemplary battery element for a contact lens type example. The segmented components may be relatively circular-shaped 271, square-shaped 272 or rectangular-shaped. In rectangular-shaped examples, the rectangles may be small rectangular shapes 273, larger rectangular shapes 274, or even larger rectangular shapes 275.

Custom Shapes of Flat Battery Elements

In some examples of biocompatible batteries, the batteries may be formed as flat elements. Referring to FIG. 3A, an example of a rectangular outline 310 of the battery element is depicted with an anode connection 311 and a cathode connection 312. Referring to FIG. 3B, an example of a circular outline 330 of a battery element is depicted with an anode connection 331 and a cathode connection 332.

In some examples of flat-formed batteries, the outlines of the battery form may be dimensionally and geometrically configured to fit in custom products. In addition to examples with rectangular or circular outlines, custom "free-form" or "free shape" outlines may be formed which may allow the battery configuration to be optimized to fit within a given product.

In the exemplary biomedical device case of a variable optic, a "free-form" example of a flat outline may be arcuate in form. The free form may be of such geometry that when formed to a three-dimensional shape, it may take the form of a conical, annular skirt that fits within the constraining confines of a contact lens. It may be clear that similar beneficial geometries may be formed where medical devices have restrictive 2D or 3D shape requirements.

Biocompatibility Aspects of Batteries

As an example, the batteries according to the present invention may have important aspects relating to safety and biocompatibility. In some examples, batteries for biomedical devices may need to meet requirements above and beyond those for typical usage scenarios. In some examples, design aspects may be considered related to stressing events. For example, the safety of an electronic contact lens may need to be considered in the event a user breaks the lens during insertion or removal. In another example, design aspects may consider the potential for a user to be struck in the eye by a foreign object. Still further examples of stressful conditions that may be considered in developing design parameters and constraints may relate to the potential for a user to wear the lens in challenging environments like the environment under water or the environment at high altitude in non-limiting examples.

The safety of such a device may be influenced by the materials that the device is formed with or from, by the quantities of those materials employed in manufacturing the device, and also by the packaging applied to separate the devices from the surrounding on- or in-body environment. In an example, pacemakers may be a typical type of biomedical device which may include a battery and which may be implanted in a user for an extended period of time. Accordingly, in some examples, such pacemakers may typically be packaged with welded, hermetic titanium enclosures, or in other examples, multiple layers of encapsulation. Emerging powered biomedical devices may present new challenges for packaging, especially battery packaging. These new devices may be much smaller than existing biomedical devices, for example, an electronic contact lens or pill camera may be significantly smaller than a pacemaker. In such examples, the volume and area available for packaging may be greatly reduced.

Electrical Requirements of Microbatteries

Another area for design considerations may relate to electrical requirements of the device, which may be provided by the battery. In order to function as a power source for a medical device, an appropriate battery may need to meet the full electrical requirements of the system when operating in a non-connected or non-externally powered mode. An emerging field of non-connected or non-externally powered biomedical devices may include, for example, vision-correcting contact lenses, health monitoring devices, pill cameras, and novelty devices. Recent developments in integrated circuit (IC) technology may permit meaningful electrical operation at very low current levels, for example, picoamps of standby current and microamps of operating current. IC's may also permit very small devices.

Microbatteries for biomedical applications may be required to meet many simultaneous, challenging requirements. For example, the microbattery may be required to have the capability to deliver a suitable operating voltage to an incorporated electrical circuit. This operating voltage may be influenced by several factors including the IC process "node," the output voltage from the circuit to another device, and a particular current consumption target which may also relate to a desired device lifetime.

With respect to the IC process, nodes may typically be differentiated by the minimum feature size of a transistor, such as its "so-called" transistor channel. This physical feature, along with other parameters of the IC fabrication, such as gate oxide thickness, may be associated with a resulting rating standard for "turn-on" or "threshold" voltages of field-effect transistors (FET's) fabricated in the given process node. For example, in a node with a minimum feature size of 0.5 microns, it may be common to find FET's with turn-on voltages of 5.0V. However, at a minimum feature size of 90 nm, the FET's may turn-on at 1.2, 1.8, and 2.5V. The IC foundry may supply standard cells of digital blocks, for example, inverters and flip-flops that have been characterized and are rated for use over certain voltage ranges. Designers chose an IC process node based on several factors including density of digital devices, analog/digital mixed signal devices, leakage current, wiring layers, and availability of specialty devices such as high-voltage FET's. Given these parametric aspects of the electrical components, which may draw power from a microbattery, it may be important for the microbattery power source to be matched to the requirements of the chosen process node and IC design, especially in terms of available voltage and current.

In some examples, an electrical circuit powered by a microbattery, may connect to another device. In non-limiting examples, the microbattery-powered electrical circuit may connect to an actuator or a transducer. Depending on the application, these may include a light-emitting diode (LED), a sensor, a microelectromechanical system (MEMS) pump, or numerous other such devices. In some examples, such connected devices may require higher operating voltage conditions than common IC process nodes. For example, a variable-focus lens may require 35V to activate. The operating voltage provided by the battery may therefore be a critical consideration when designing such a system. In some examples of this type of consideration, the efficiency of a lens driver to produce 35V from a 1V battery may be significantly less than it might be when operating from a 2V battery. Further requirements, such as die size, may be dramatically different considering the operating parameters of the microbattery as well.

Individual battery cells may typically be rated with open-circuit, loaded, and cutoff voltages. The open-circuit voltage is the potential produced by the battery cell with infinite load resistance. The loaded voltage is the potential produced by the cell with an appropriate, and typically also specified, load impedance placed across the cell terminals. The cutoff voltage is typically a voltage at which most of the battery has been discharged. The cutoff voltage may represent a voltage, or degree of discharge, below which the battery should not be discharged to avoid deleterious effects such as excessive gassing. The cutoff voltage may typically be influenced by the circuit to which the battery is connected, not just the battery itself, for example, the minimum operating voltage of the electronic circuit. In one example, an alkaline cell may have an open-circuit voltage of 1.6V, a loaded voltage in the range 1.0 to 1.5V, and a cutoff voltage of 1.0V. The voltage of a given microbattery cell design may depend upon other factors of the cell chemistry employed. And, different cell chemistry may therefore have different cell voltages.

Cells may be connected in series to increase voltage; however, this combination may come with tradeoffs to size, internal resistance, and battery complexity. Cells may also be combined in parallel configurations to decrease resistance and increase capacity; however, such a combination may tradeoff size and shelf life.

Battery capacity may be the ability of a battery to deliver current, or do work, for a period of time. Battery capacity may typically be specified in units such as microamp-hours. A battery that may deliver 1 microamp of current for 1 hour has 1 microamp-hour of capacity. Capacity may typically be increased by increasing the mass (and hence volume) of reactants within a battery device; however, it may be appreciated that biomedical devices may be significantly constrained on available volume. Battery capacity may also be influenced by electrode and electrolyte material.

Depending on the requirements of the circuitry to which the battery is connected, a battery may be required to source current over a range of values. During storage prior to active use, a leakage current on the order of picoamps to nanoamps may flow through circuits, interconnects, and insulators. During active operation, circuitry may consume quiescent current to sample sensors, run timers, and perform such low power consumption functions. Quiescent current consumption may be on the order of nanoamps to milliamps. Circuitry may also have even higher peak current demands, for example, when writing flash memory or communicating over radio frequency (RF). This peak current may extend to tens of milliamps or more. The resistance and impedance of a microbattery device may also be important to design considerations.

Shelf life typically refers to the period of time which a battery may survive in storage and still maintain useful operating parameters. Shelf life may be particularly important for biomedical devices for several reasons. Electronic devices may displace non-powered devices, as for example may be the case for the introduction of an electronic contact lens. Products in these existing market spaces may have established shelf life requirements, for example, three years, due to customer, supply chain, and other requirements. It may typically be desired that such specifications not be altered for new products. Shelf life requirements may also be set by the distribution, inventory, and use methods of a device including a microbattery. Accordingly, microbatteries for biomedical devices may have specific shelf life requirements, which may be, for example, measured in the number of years.

In some examples, three-dimensional biocompatible energization elements may be rechargeable. For example, an inductive coil may also be fabricated on the three-dimensional surface. The inductive coil could then be energized with a radio-frequency ("RF") fob. The inductive coil may be connected to the three-dimensional biocompatible energization element to recharge the energization element when RF is applied to the inductive coil. In another example, photovoltaics may also be fabricated on the three-dimensional surface and connected to the three-dimensional biocompatible energization element. When exposed to light or photons, the photovoltaics will produce electrons to recharge the energization element.

In some examples, a battery may function to provide the electrical energy for an electrical system. In these examples, the battery may be electrically connected to the circuit of the electrical system. The connections between a circuit and a battery may be classified as interconnects. These interconnects may become increasingly challenging for biomedical microbatteries due to several factors. In some examples, powered biomedical devices may be very small thus allowing little area and volume for the interconnects. The restrictions of size and area may impact the electrical resistance and reliability of the interconnections.

In other respects, a battery may contain a liquid electrolyte which could boil at high temperature. This restriction may directly compete with the desire to use a solder interconnect which may, for example, require relatively high temperatures such as 250 degrees Celsius to melt. Although in some examples, the battery chemistry, including the electrolyte, and the heat source used to form solder based interconnects, may be isolated spatially from each other. In the cases of emerging biomedical devices, the small size may preclude the separation of electrolyte and solder joints by sufficient distance to reduce heat conduction.

Interconnects

Interconnects may allow current to flow to and from the battery in connection with an external circuit. Such interconnects may interface with the environments inside and outside the battery, and may cross the boundary or seal between those environments. These interconnects may be considered as traces, making connections to an external circuit, passing through the battery seal, and then connecting to the current collectors inside the battery. As such, these interconnects may have several requirements. Outside the battery, the interconnects may resemble typical printed circuit traces. They may be soldered to, or otherwise connect to, other traces. In an example where the battery is a separate physical element from a circuit board comprising an integrated circuit, the battery interconnect may allow for connection to the external circuit. This connection may be formed with solder, conductive tape, conductive ink or epoxy, or other means. The interconnect traces may need to survive in the environment outside the battery, for example, not corroding in the presence of oxygen.

As the interconnect passes through the battery seal, it may be of critical importance that the interconnect coexist with the seal and permit sealing. Adhesion may be required between the seal and interconnect in addition to the adhesion which may be required between the seal and battery package. Seal integrity may need to be maintained in the presence of electrolyte and other materials inside the battery. Interconnects, which may typically be metallic, may be known as points of failure in battery packaging. The electrical potential and/or flow of current may increase the tendency for electrolyte to "creep" along the interconnect. Accordingly, an interconnect may need to be engineered to maintain seal integrity.

Inside the battery, the interconnects may interface with the current collectors or may actually form the current collectors. In this regard, the interconnect may need to meet the requirements of the current collectors as described herein, or may need to form an electrical connection to such current collectors.

One class of candidate interconnects and current collectors is metal foils. Such foils are available in thickness of 25 microns or less, which make them suitable for very thin batteries. Such foil may also be sourced with low surface roughness and contamination, two factors which may be critical for battery performance. The foils may include zinc, nickel, brass, copper, titanium, other metals, and various alloys.

Electrolyte

An electrolyte is a component of a battery which facilitates a chemical reaction to take place between the chemical materials of the electrodes. Typical electrolytes may be electrochemically active to the electrodes, for example, allowing oxidation and reduction reactions to occur. In some examples, this important electrochemical activity may make for a challenge to creating devices that are biocompatible. For example, potassium hydroxide (KOH) may be a commonly used electrolyte in alkaline cells. At high concentration the material has a high pH and may interact unfavorably with various living tissues. On the other hand, in some examples, electrolytes may be employed which may be less electrochemically active; however, these materials may typically result in reduced electrical performance, such as reduced cell voltage and increased cell resistance. Accordingly, one key aspect of the design and engineering of a biomedical microbattery may be the electrolyte. It may be desirable for the electrolyte to be sufficiently active to meet electrical requirements while also being relatively safe for use in- or on-body.

Various test scenarios may be used to determine the safety of battery components, in particular electrolytes, to living cells. These results, in conjunction with tests of the battery packaging, may allow engineering design of a battery system that may meet requirements. For example, when developing a powered contact lens, battery electrolytes may be tested on a human corneal cell model. These tests may include experiments on electrolyte concentration, exposure time, and additives. The results of such tests may indicate cell metabolism and other physiological aspects. Tests may also include in-vivo testing on animals and humans.

Electrolytes for use in the present invention may include zinc chloride, zinc acetate, ammonium acetate, and ammonium chloride in mass concentrations from approximately 0.1 percent to 50 percent, and in a non-limiting example may be approximately 25 percent. The specific concentrations may depend on electrochemical activity, battery performance, shelf life, seal integrity, and biocompatibility.

In some examples, several classes of additives may be utilized in the composition of a battery system. Additives may be mixed into the electrolyte base to alter its characteristics. For example, gelling agents such as agar may reduce the ability of the electrolyte to leak out of packing, thereby increasing safety. Corrosion inhibitors may be added to the electrolyte, for example, to improve shelf life by reducing the undesired dissolution of the zinc anode into the electrolyte. These inhibitors may positively or adversely affect the safety profile of the battery. Wetting agents or surfactants may be added, for example, to allow the electrolyte to wet the separator or to be filled into the battery package. Again, these wetting agents may be positive or negative for safety. The addition of surfactant to the electrolyte may increase the electrical impedance of the cell. Accordingly, the lowest concentration of surfactant to achieve the desired wetting or other properties should be used. Exemplary surfactants may include Triton™ X-100, Triton™ QS44, and Dowfax™ 3B2 in concentrations from 0.01 percent to 2 percent.

Novel electrolytes are also emerging which may dramatically improve the safety profile of biomedical microbatteries. For example, a class of solid electrolytes may be inherently resistant to leaking while still offering suitable electrical performance.

Batteries using "salt water" electrolyte are commonly used in reserve cells for marine use. Torpedoes, buoys, and emergency lights may use such batteries. Reserve cells are batteries in which the active materials, the electrodes and electrolyte, are separated until the time of use. Because of this separation, the cells' self-discharge is greatly reduced and shelf life is greatly increased. Salt water batteries may be designed from a variety of electrode materials, including zinc, magnesium, aluminum, copper, tin, manganese dioxide, and silver oxide. The electrolyte may be actual sea water, for example, water from the ocean flooding the battery upon contact, or may be a specially engineered saline formulation. This type of battery may be particularly useful in contact lenses. A saline electrolyte may have superior biocompatibility to classical electrolytes such as potassium hydroxide and zinc chloride. Contact lenses are stored in a "packing solution" which is typically a mixture of sodium chloride, perhaps with other salts and buffering agents. This solution has been demonstrated as a battery electrolyte in combination with a zinc anode and manganese dioxide cathode. Other electrolyte and electrode combinations are possible. A contact lens using a "salt water" battery may comprise an electrolyte based on sodium chloride, packing solution, or even a specially engineered electrolyte similar to tear fluid. Such a battery could, for example, be activated with packing solution, maintain an opening to the eye, and continue operating with exposure to human tears.

In addition to, or instead of, possible benefits for biocompatibility by using an electrolyte more similar to tears, or actually using tears, a reserve cell may be used to meet the shelf life requirements of a contact lens product. Typical contact lenses are specified for storage of 3 years or more. This is a challenging requirement for a battery with a small and thin package. A reserve cell for use in a contact lens may have a design similar to those shown in FIGS. 1 and 3, but the electrolyte might not be added at the time of manufacture. The electrolyte may be stored in an ampule within the contact lens and connected to the battery, or saline surrounding the battery may be used as the electrolyte. Within the contact lens and battery package, a valve or port may be designed to separate the electrolyte from the electrodes until the user activates the lens. Upon activation, perhaps by simply pinching the edge of the contact lens (similar to activating a glow stick), the electrolyte may be allowed to flow into the battery and form an ionic pathway between the electrodes. This may involve a one-time transfer of electrolyte or may expose the battery for continued diffusion.

Some battery systems may use or consume electrolyte during the chemical reaction. Accordingly, it may be necessary to engineer a certain volume of electrolyte into the packaged system. This electrolyte may be stored in various locations including the separator or a reservoir.

In some examples, a design of a battery system may include a component or components that may function to limit discharge capacity of the battery system. For example, it may be desirable to design the materials and amounts of materials of the anode, cathode, or electrolyte such that one of them may be depleted first during the course of reactions in the battery system. In such an example, the depletion of one of the anode, cathode, or electrolyte may reduce the potential for problematic discharge and side reactions to not take place at lower discharge voltages. These problematic reactions may produce, for example, excessive gas or byproducts which could be detrimental to safety and other factors.

Modular Battery Components

In some examples, a modular battery component may be formed according to some aspects and examples of the present invention. In these examples, the modular battery assembly may be a separate component from other parts of the biomedical device. In the example of an ophthalmic contact lens device, such a design may include a modular battery that is separate from the rest of a media insert. There may be numerous advantages of forming a modular battery component. For example, in the example of the contact lens, a modular battery component may be formed in a separate, non-integrated process which may alleviate the need to handle rigid, three-dimensionally formed optical plastic components. In addition, the sources of manufacturing may be more flexible and may operate in a more parallel mode to the manufacturing of the other components in the biomedical device. Furthermore, the fabrication of the modular battery components may be decoupled from the characteristics of three-dimensional (3D) shaped devices. For example, in applications requiring three-dimensional final forms, a modular battery system may be fabricated in a flat or roughly two-dimensional (2D) perspective and then shaped to the appropriate three-dimensional shape. A modular battery component may be tested independently of the rest of the biomedical device and yield loss due to battery components may be sorted before assembly. The resulting modular battery component may be utilized in various media insert constructs that do not have an appropriate rigid region upon which the battery components may be formed; and, in a still further example, the use of modular battery components may facilitate the use of different options for fabrication technologies than might otherwise be utilized, such as, web-based technology (roll to roll), sheet-based technology (sheet-to-sheet), printing, lithography, and "squeegee" processing. In some examples of a modular battery, the discrete containment aspect of such a device may result in additional material being added to the overall biomedical device construct. Such effects may set a constraint for the use of modular battery solutions when the available space parameters require minimized thickness or volume of solutions.

Battery shape requirements may be driven at least in part by the application for which the battery is to be used. Traditional battery form factors may be cylindrical forms or rectangular prisms, made of metal, and may be geared toward products which require large amounts of power for long durations. These applications may be large enough that they may comprise large form factor batteries. In another example, planar (2D) solid-state batteries are thin rectangular prisms, typically formed upon inflexible silicon or glass. These planar solid-state batteries may be formed in some examples using silicon wafer-processing technologies. In another type of battery form factor, low power, flexible batteries may be formed in a pouch construct, using thin foils or plastic to contain the battery chemistry. These batteries may be made flat (2D), and may be designed to function when bowed to a modest out-of-plane (3D) curvature.

In some of the examples of the battery applications in the present invention where the battery may be employed in a variable optic lens, the form factor may require a three-dimensional curvature of the battery component where a radius of that curvature may be on the order of approximately 8.4 mm. The nature of such a curvature may be considered to be relatively steep and for reference may approximate the type of curvature found on a human fingertip. The nature of a relative steep curvature creates challenging aspects for manufacture. In some examples of the present invention, a modular battery component may be designed such that it may be fabricated in a flat, two-dimensional manner and then formed into a three-dimensional form of relative high curvature.

Battery Module Thickness

In designing battery components for biomedical applications, tradeoffs amongst the various parameters may be made balancing technical, safety and functional requirements. The thickness of the battery component may be an important and limiting parameter. For example, in an optical lens application the ability of a device to be comfortably worn by a user may have a critical dependence on the thickness across the biomedical device. Therefore, there may be critical enabling aspects in designing the battery for thinner results. In some examples, battery thickness may be determined by the combined thicknesses of top and bottom sheets, spacer sheets, and adhesive layer thicknesses. Practical manufacturing aspects may drive certain parameters of film thickness to standard values in available sheet stock. In addition, the films may have minimum thickness values to which they may be specified base upon technical considerations relating to chemical compatibility, moisture/gas impermeability, surface finish, and compatibility with coatings that may be deposited upon the film layers.

In some examples, a desired or goal thickness of a finished battery component may be a component thickness that is less than 220 µm. In these examples, this desired thickness may be driven by the three-dimensional geometry of an exemplary ophthalmic lens device where the battery component may need to be fit inside the available volume defined by a hydrogel lens shape given end user comfort, biocompatibility, and acceptance constraints. This volume and its effect on the needs of battery component thickness may be a function of total device thickness specification as well as device specification relating to its width, cone angle, and inner diameter. Another important design consideration for the resulting battery component design may relate to the volume available for active battery chemicals and materials in a given battery component design with respect to the resulting chemical energy that may result from that design. This resulting chemical energy may then be balanced for the electrical requirements of a functional biomedical device for its targeted life and operating conditions Battery Module Flexibility Another dimension of relevance to battery design and to the design of related devices that utilize battery based energy sources is the flexibility of the battery component. There may be numerous advantages conferred by flexible battery forms. For example, a flexible battery module may facilitate the previously mentioned ability to fabricate the battery form in a two-dimensional (2D) flat form. The flexibility of the form may allow the two-dimensional battery to then be formed into an appropriate 3D shape to fit into a biomedical device such as a contact lens.

In another example of the benefits that may be conferred by flexibility in the battery module, if the battery and the subsequent device is flexible then there may be advantages relating to the use of the device. In an example, a contact lens form of a biomedical device may have advantages for insertion/removal of the media insert based contact lens that may be closer to the insertion/removal of a standard, non-filled hydrogel contact lens.

The number of flexures may be important to the engineering of the battery. For example, a battery which may only flex one time from a planar form into a shape suitable for a contact lens may have significantly different design from a battery capable of multiple flexures. The flexure of the battery may also extend beyond the ability to mechanically survive the flexure event. For example, an electrode may be physically capable of flexing without breaking, but the mechanical and electrochemical properties of the electrode may be altered by flexure. Flex-induced changes may appear instantly, for example, as changes to impedance, or flexure may introduce changes which are only apparent in long-term shelf life testing.

Battery Module Width

There may be numerous applications into which the biocompatible energization elements or batteries of the present invention may be utilized. In general, the battery width requirement may be largely a function of the application in which it is applied. In an exemplary case, a contact lens battery system may have constrained needs for the specification on the width of a modular battery component. In some examples of an ophthalmic device where the device has a variable optic function powered by a battery component, the variable optic portion of the device may occupy a central spherical region of about 7.0 mm in diameter. The exemplary battery elements may be considered as a three-dimensional object, which fits as an annular, conical skirt around the central optic and formed into a truncated conical ring. If the required maximum diameter of the rigid insert is a diameter of 8.50 mm, and tangency to a certain diameter sphere may be targeted (as for example in a roughly 8.40 mm diameter), then geometry may dictate what the allowable battery width may be. There may be geometric models that may be useful for calculating desirable specifications for the resulting geometry which in some examples may be termed a conical frustum flattened into a sector of an annulus.

Flattened battery width may be driven by two features of the battery element, the active battery components and seal width. In some examples relating to ophthalmic devices a target thickness may be between 0.100 mm and 0.500 mm per side, and the active battery components may be targeted at roughly 0.800 mm wide. Other biomedical devices may have differing design constraints but the principles for flexible flat battery elements may apply in similar fashion.

Cavities as Design Elements in Battery Component Design

In some examples, battery elements may be designed in manners that segment the regions of active battery chemistry. There may be numerous advantages from the division of the active battery components into discrete segments. In a non-limiting example, the fabrication of discrete and smaller elements may facilitate production of the elements. The function of battery elements including numerous smaller elements may be improved. Defects of various kinds may be segmented and non-functional elements may be isolated in some cases to result in decreased loss of function. This may be relevant in examples where the loss of battery electrolyte may occur. The isolation of individualized components may allow for a defect that results in leakage of electrolyte out of the critical regions of the battery to limit the loss of function to that small segment of the total battery element whereas the electrolyte loss through the defect could empty a significantly larger region for batteries configured as a single cell. Smaller cells may result in lowered volume of active battery chemicals on an overall perspective, but the mesh of material surrounding each of the smaller cells may result in a strengthening of the overall structure.

Battery Element Internal Seals

In some examples of battery elements for use in biomedical devices, the chemical action of the battery involves aqueous chemistry, where water or moisture is an important constituent to control. Therefore it may be important to incorporate sealing mechanisms that retard or prevent the movement of moisture either out of or into the battery body. Moisture barriers may be designed to keep the internal moisture level at a designed level, within some tolerance. In some examples, a moisture barrier may be divided into two sections or components; namely, the package and the seal.

The package may refer to the main material of the enclosure. In some examples, the package may comprise a bulk material. The Water Vapor Transmission Rate (WVTR) may be an indicator of performance, with ISO, ASTM standards controlling the test procedure, including the environmental conditions operant during the testing. Ideally, the WVTR for a good battery package may be "zero." Exemplary materials with a near-zero WVTR may be glass and metal foils. Plastics, on the other hand, may be inherently porous to moisture, and may vary significantly for different types of plastic. Engineered materials, laminates, or co-extrudes may usually be hybrids of the common package materials.

The seal may be the interface between two of the package surfaces. The connecting of seal surfaces finishes the enclosure along with the package. In many examples, the nature of seal designs may make them difficult to characterize for the seal's WVTR due to difficulty in performing measurements using an ISO or ASTM standard, as the sample size or surface area may not be compatible with those procedures. In some examples, a practical manner to testing seal integrity may be a functional test of the actual seal design, for some defined conditions. Seal performance may be a function of the seal material, the seal thickness, the seal length, the seal width, and the seal adhesion or intimacy to package substrates.

In some examples, seals may be formed by a welding process that may involve thermal, laser, solvent, friction, ultrasonic, or arc processing. In other examples, seals may be formed through the use of adhesive sealants such as glues, epoxies, acrylics, natural rubber, and synthetic rubber. Other examples may derive from the utilization of gasket type material that may be formed from cork, natural and synthetic rubber, polytetrafluoroethylene (PTFE), polypropylene, and silicones to mention a few non-limiting examples.

In some examples, the batteries according to the present invention may be designed to have a specified operating life. The operating life may be estimated by determining a practical amount of moisture permeability that may be obtained using a particular battery system and then estimating when such a moisture leakage may result in an end of life condition for the battery. For example, if a battery is stored in a wet environment, then the partial pressure difference between inside and outside the battery will be minimal, resulting in a reduced moisture loss rate, and therefore the battery life may be extended. The same exemplary battery stored in a particularly dry and hot environment may have a significantly reduced expectable lifetime due to the strong driving function for moisture loss.

Battery Element Separators

Batteries of the type described in the present invention may utilize a separator material that physically and electrically separates the anode and anode current collector portions from the cathode and cathode current collector portions. The separator may be a membrane that is permeable to water and dissolved electrolyte components; however, it may typically be electrically non-conductive. While a myriad of commercially-available separator materials may be known to those of skill in the art, the novel form factor of the present invention may present unique constraints on the task of separator selection, processing, and handling.

Since the designs of the present invention may have ultra-thin profiles, the choice may be limited to the thinnest separator materials typically available. For example, separators of approximately 25 microns in thickness may be desirable. Some examples which may be advantageous may be about 12 microns in thickness. There may be numerous acceptable commercial separators include microfibrillated, microporous polyethylene monolayer and/or polypropylene-polyethylene-polypropylene (PP/PE/PP) trilayer separator membranes such as those produced by Celgard (Charlotte, N.C.). A desirable example of separator material may be Celgard M824 PP/PE/PP trilayer membrane having a thickness of 12 microns. Alternative examples of separator materials useful for examples of the present invention may include separator membranes including regenerated cellulose (e.g. cellophane).

While PP/PE/PP trilayer separator membranes may have advantageous thickness and mechanical properties, owing to their polyolefinic character, they may also suffer from a number of disadvantages that may need to be overcome in order to make them useful in examples of the present invention. Roll or sheet stock of PP/PE/PP trilayer separator materials may have numerous wrinkles or other form errors that may be deleterious to the micron-level tolerances applicable to the batteries described herein. Furthermore, polyolefin separators may need to be cut to ultra-precise tolerances for inclusion in the present designs, which may therefore implicate laser cutting as an exemplary method of forming discrete current collectors in desirable shapes with tight tolerances. Owing to the polyolefinic character of these separators, certain cutting lasers useful for micro fabrication may employ laser wavelengths, e.g. 355 nm, that will not cut polyolefins. The polyolefins do not appreciably absorb the laser energy and are thereby non-ablatable. Finally, polyolefin separators may not be inherently wettable to aqueous electrolytes used in the batteries described herein.

Nevertheless, there may be methods for overcoming these inherent limitations for polyolefinic type membranes. In order to present a microporous separator membrane to a high-precision cutting laser for cutting pieces into arc segments or other advantageous separator designs, the membrane may need to be flat and wrinkle-free. If these two conditions are not met, the separator membrane may not be fully cut because the cutting beam may be inhibited as a result of defocusing of or otherwise scattering the incident laser energy. Additionally, if the separator membrane is not flat and wrinkle-free, the form accuracy and geometric tolerances of the separator membrane may not be sufficiently achieved. Allowable tolerances for separators of current examples may be, for example, +0 microns and −20 microns with respect to characteristic lengths and/or radii. There may be advantages for tighter tolerances of +0 microns and −10 micron and further for tolerances of +0 microns and −5 microns. Separator stock material may be made flat and wrinkle-free by temporarily laminating the material to a float glass carrier with an appropriate low-volatility liquid. Low-volatility liquids may have advantages over temporary adhesives due to the fragility of the separator membrane and due to the amount of processing time that may be required to release separator membrane from an adhesive layer. Furthermore, in some examples achieving a flat and wrinkle-free separator membrane on float glass using a liquid has been observed to be much more facile than using an adhesive. Prior to lamination, the separator membrane may be made free of particulates. This may be achieved by ultrasonic cleaning of separator membrane to dislodge any surface-adherent particulates. In some examples, handling of a separator membrane may be done in a suitable, low-particle environment such as a laminar flow hood or a cleanroom of at least class 10,000. Furthermore, the float glass substrate may be made to be particulate free by rinsing with an appropriate solvent, ultrasonic cleaning, and/or wiping with clean room wipes.

While a wide variety of low-volatility liquids may be used for the mechanical purpose of laminating microporous polyolefin separator membranes to a float glass carrier, specific requirements may be imposed on the liquid to facilitate subsequent laser cutting of discrete separator shapes. One requirement may be that the liquid has a surface tension low enough to soak into the pores of the separator material which may easily be verified by visual inspection. In some examples, the separator material turns from a white color to a translucent appearance when liquid fills the micropores of the material. It may be desirable to choose a liquid that may be benign and "safe" for workers that will be exposed to the preparation and cutting operations of the separator. It may be desirable to choose a liquid whose vapor pressure may be low enough so that appreciable evaporation does not occur during the time scale of processing (on the order of 1 day). Finally, in some examples the liquid may have sufficient solvating power to dissolve advantageous UV absorbers that may facilitate the laser cutting operation. In an example, it has been observed that a 12 percent (w/w) solution of avobenzone UV absorber in benzyl benzoate solvent may meet the aforementioned requirements and may lend itself to facilitating the laser cutting of polyolefin separators with high precision and tolerance in short order without an excessive number of passes of the cutting laser beam. In some examples, separators may be cut with an 8 W 355 nm nanosecond diode-pumped solid state laser using this approach where the laser may have settings for low power attenuation (e.g. 3 percent power), a moderate speed of 1 to 10 mm/s, and only 1 to 3 passes of the laser beam. While this UV-absorbing oily composition has been proven to be an effective laminating and cutting process aid, other oily formulations may be envisaged by those of skill in the art and used without limitation.

In some examples, a separator may be cut while fixed to a float glass. One advantage of laser cutting separators while fixed to a float glass carrier may be that a very high number density of separators may be cut from one separator stock sheet much like semiconductor die may be densely arrayed on a silicon wafer. Such an approach may provide economy of scale and parallel processing advantages inherent in semiconductor processes. Furthermore, the generation of scrap separator membrane may be minimized. Once separators have been cut, the oily process aid fluid may be removed by a series of extraction steps with miscible solvents, the last extraction may be performed with a high-volatility solvent such as isopropyl alcohol in some examples. Discrete separators, once extracted, may be stored indefinitely in any suitable low-particle environment.

As previously mentioned polyolefin separator membranes may be inherently hydrophobic and may need to be made wettable to aqueous surfactants used in the batteries of the present invention. One approach to make the separator membranes wettable may be oxygen plasma treatment. For example, separators may be treated for 1 to 5 minutes in a 100 percent oxygen plasma at a wide variety of power settings and oxygen flow rates. While this approach may improve wettability for a time, it may be well-known that plasma surface modifications provide a transient effect that may not last long enough for robust wetting of electrolyte solutions. Another approach to improve wettability of separator membranes may be to treat the surface by incorporating a suitable surfactant on the membrane. In some cases, the surfactant may be used in conjunction with a hydrophilic polymeric coating that remains within the pores of the separator membrane.

Another approach to provide more permanence to the hydrophilicity imparted by an oxidative plasma treatment may be by subsequent treatment with a suitable hydrophilic organosilane. In this manner, the oxygen plasma may be used to activate and impart functional groups across the entire surface area of the microporous separator. The organosilane may then covalently bond to and/or non-covalently adhere to the plasma treated surface. In examples using an organosilane, the inherent porosity of the microporous separator may not be appreciably changed, monolayer surface coverage may also be possible and desired. Prior art methods incorporating surfactants in conjunction with polymeric coatings may require stringent controls over the actual amount of coating applied to the membrane, and may then be subject to process variability. In extreme cases, pores of the separator may become blocked, thereby adversely affecting utility of the separator during the operation of the electrochemical cell. An exemplary organosilane useful in the present invention may be (3-aminopropyl)triethoxysilane. Other hydrophilic organosilanes may be known to those of skill in the art and may be used without limitation.

Still another method for making separator membranes wettable by aqueous electrolyte may be the incorporation of a suitable surfactant in the electrolyte formulation. One consideration in the choice of surfactant for making separator membranes wettable may be the effect that the surfactant may have on the activity of one or more electrodes within the electrochemical cell, for example, by increasing the electrical impedance of the cell. In some cases, surfactants may have advantageous anti-corrosion properties, specifically in the case of zinc anodes in aqueous electrolytes. Zinc may be an example known to undergo a slow reaction with water to liberate hydrogen gas, which may be undesirable. Numerous surfactants may be known by those of skill in the art to limit rates of said reaction to advantageous levels. In other cases, the surfactant may so strongly interact with the zinc electrode surface that battery performance may be impeded. Consequently, much care may need to be made in the selection of appropriate surfactant types and loading levels to ensure that separator wettability may be obtained without deleteriously affecting electrochemical performance of the cell. In some cases, a plurality of surfactants may be used, one being present to impart wettability to the separator membrane and the other being present to facilitate anti-corrosion properties to the zinc anode. In one example, no hydrophilic treatment is done to the separator membrane and a surfactant or plurality of surfactants is added to the electrolyte formulation in an amount sufficient to effect wettability of the separator membrane.

Discrete separators may be integrated into the laminar microbattery by direct placement into a means for storage including a designed cavity, pocket, or structure within the assembly. Desirably, this storage means may be formed by a laminar structure having a cutout, which may be a geometric offset of the separator shape, resulting in a cavity, pocket, or structure within the assembly. Furthermore, the storage means may have a ledge or step on which the separator rests during assembly. The ledge or step may optionally include a pressure-sensitive adhesive which retains the discrete separator. Advantageously, the pressure-sensitive adhesive may be the same one used in the construction and stack up of other elements of an exemplary laminar microbattery.

Pressure Sensitive Adhesive

In some examples, the plurality of components composing the laminar microbatteries of the present invention may be held together with a pressure-sensitive adhesive (PSA) that also serves as a sealant. While a myriad of commercially available pressure-sensitive adhesive formulations may exist, such formulations almost always include components that may make them unsuitable for use within a biocompatible laminar microbattery. Examples of undesirable components in pressure-sensitive adhesives may include low molecular mass leachable components, antioxidants e.g. BHT and/or MEHQ, plasticizing oils, impurities, oxidatively unstable moieties containing, for example, unsaturated chemical bonds, residual solvents and/or monomers, polymerization initiator fragments, polar tackifiers, and the like.

Suitable PSAs may on the other hand exhibit the following properties. They may be able to be applied to laminar components to achieve thin layers on the order of 2 to 20 microns. As well, they may comprise a minimum of, for example, zero undesirable or non-biocompatible components. Additionally, they may have sufficient adhesive and cohesive properties so as to bind the components of the laminar battery together. And, they may be able to flow into the micron-scale features inherent in devices of the present construction while providing for a robust sealing of electrolyte within the battery. In some examples of suitable PSAs, the PSAs may have a low permeability to water vapor in order to maintain a desirable aqueous electrolyte composition within the battery even when the battery may be subjected to extremes in humidity for extended periods of time. The PSAs may have good chemical resistance to components of electrolytes such as acids, surfactants, and salts. They may be inert to the effects of water immersion. Suitable PSAs may have a low permeability to oxygen to minimize the rate of direct oxidation, which may be a form of self-discharge, of zinc anodes. And, they may facilitate a finite permeability to hydrogen gas, which may be slowly evolved from zinc anodes in aqueous electrolytes. This property of finite permeability to hydrogen gas may avoid a build-up of internal pressure.

In consideration of these requirements, polyisobutylene (PIB) may be a commercially-available material that may be formulated into PSA compositions meeting many if not all desirable requirements. Furthermore, PIB may be an excellent barrier sealant with very low water absorbance and low oxygen permeability. An example of PIB useful in the examples of the present invention may be Oppanol® B15 by BASF Corporation. Oppanol® B15 may be dissolved in hydrocarbon solvents such as toluene, heptane, dodecane, mineral spirits, and the like. One exemplary PSA composition may include 30 percent Oppanol® B15 (w/w) in a solvent mixture including 70 percent (w/w) toluene and 30 percent dodecane. The adhesive and rheological properties of PIB based PSA's may be determined in some examples by the blending of different molecular mass grades of PIB. A common approach may be to use a majority of low molar mass PIB, e.g. Oppanol® B10 to affect wetting, tack, and adhesion, and to use a minority of high molar mass PIB to effect toughness and resistance to flow. Consequently, blends of any number of PIB molar mass grades may be envisioned and may be practiced within the scope of the present invention. Furthermore, tackifiers may be added to the PSA formulation so long as the aforementioned requirements may be met. By their very nature, tackifiers impart polar properties to PSA formulations, so they may need to be used with caution so as to not adversely affect the barrier properties of the PSA. Furthermore, tackifiers may in some cases be oxidatively unstable and may include an antioxidant, which could leach out of the PSA. For these reasons, exemplary tackifiers for use in PSA's for biocompatible laminar microbatteries may include fully- or mostly hydrogenated hydrocarbon resin tackifiers such as the Regalrez series of tackifiers from Eastman Chemical Corporation.

Additional Package and Substrate Considerations in Biocompatible Battery Modules There may be numerous packaging and substrate considerations that may dictate desirable characteristics for package designs used in biocompatible laminar microbatteries. For example, the packaging may desirably be predominantly foil and/or film based where these packaging layers may be as thin as possible, for example, 10 to 50 microns. Additionally, the packaging may provide a sufficient diffusion barrier to moisture gain or loss during the shelf life. In many desirable examples, the packaging may provide a sufficient diffusion barrier to oxygen ingress to limit degradation of zinc anodes by direct oxidation.

In some examples, the packaging may provide a finite permeation pathway to hydrogen gas that may evolve due to direct reduction of water by zinc. And, the packaging may desirably sufficiently contain and may isolate the contents of the battery such that potential exposure to a user may be minimized.

In the present invention, packaging constructs may include the following types of functional components: top and bottom packaging layers, PSA layers, spacer layers, interconnect zones, filling ports, and secondary packaging.

In some examples, top and bottom packaging layers may comprise metallic foils or polymer films. Top and bottom packaging layers may comprise multi-layer film constructs containing a plurality of polymer and/or barrier layers. Such film constructs may be referred to as coextruded barrier laminate films. An example of a commercial coextruded barrier laminate film of particular utility in the present invention may be 3M® Scotchpak 1109 backing which consists of a polyethylene terephthalate (PET) carrier web, a vapor-deposited aluminum barrier layer, and a polyethylene layer including a total average film thickness of 33 microns. Numerous other similar multilayer barrier films may be available and may be used in alternate examples of the present invention.

In design constructions including a PSA, packaging layer surface roughness may be of particular importance because the PSA may also need to seal opposing packaging layer faces. Surface roughness may result from manufacturing processes used in foil and film production, for example, processes employing rolling, extruding, embossing and/or calendaring, among others. If the surface is too rough, PSA may be not able to be applied in a uniform thickness when the desired PSA thickness may be on the order of the surface roughness Ra (the arithmetic average of the roughness profile). Furthermore, PSA's may not adequately seal against an opposing face if the opposing face has roughness that may be on the order of the PSA layer thickness. In the present invention, packaging materials having a surface roughness, Ra, less than 10 microns may be acceptable examples. In some examples, surface roughness values may be 5 microns or less. And, in still further examples, the surface roughness may be 1 micron or less. Surface roughness values may be measured by a variety of methods including but not limited to measurement techniques such as white light interferometry, stylus profilometry, and the like. There may be many examples in the art of surface metrology that surface roughness may be described by a number of alternative parameters and that the average surface roughness, Ra, values discussed herein may be meant to be representative of the types of features inherent in the aforementioned manufacturing processes.

Figures 4M, 4N:
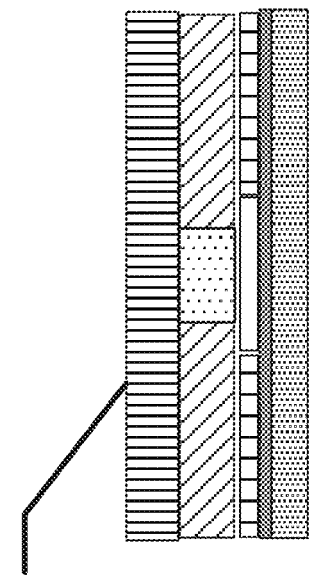

Exemplary Illustrated Processing of Biocompatible Energization Elements—Placed Separator An example of the steps that may be involved in processing biocompatible energization elements may be found referring to FIGS. 4A-4N. The processing at some of the exemplary steps may be found in the individual figures. In FIG. 4A, an exemplary combination of a PET Cathode Spacer 401 and a PET Gap Spacer 404 is illustrated. The PET Cathode Spacer 401 may be formed by applying films of PET 403 which, for example, may be roughly 3 mils thick. On either side of the PET layer may be found PSA layers or these may be capped with a PVDF release layer 402 which may be roughly 1 mil in thickness. The PET Gap spacer 404 may be formed of a PVDF layer 409 which may be roughly 3 mils in thickness. There may be a capping PET layer 405 which may be roughly 0.5 mils in thickness. Between the PVDF layer 409 and the capping PET layer 405, in some examples, may be a layer of PSA.

Proceeding to FIG. 4B, a hole 406 in the PET Gap spacer layer 404 may be cut by laser cutting treatment. Next at FIG. 4C, the cut PET Gap spacer layer 404 may be laminated 408 to the PET Cathode Spacer layer 401. Proceeding to FIG. 4D, a cathode spacer hole 410 may be cut by laser cutting treatment. The alignment of this cutting step may be registered to the previously cut features in the PET Gap spacer layer 404. At FIG. 4E, a layer of Celgard 412, for an ultimate separator layer, may be bonded to a carrier 411. Proceeding to FIG. 4F, the Celgard material may be cut to figures that are between the size of the previous two laser cut holes, and approximately the size of the hole 406 in the PET gap spacer, forming a precut separator 420. Proceeding to FIG. 4G, a pick and place tool 421 may be used to pick and place discrete pieces of Celgard into their desired locations on the growing device. At FIG. 4H, the placed Celgard pieces 422 are fastened into place and then the PVDF release layer 423 may be removed. Proceeding to FIG. 4I, the growing device structure may be bonded to a film of the anode 425. The anode 425 may comprise an anode collector film upon which a zinc anode film has been electrodeposited.

Proceeding to FIG. 4J, a cathode slurry 430 may be placed into the formed gap. A squeegee 431 may be used in some examples to spread the cathode mix across a work piece and in the process fill the gaps of the battery devices being formed. After filling, the remaining PVDF release layer 432 may be removed which may result in the structure illustrated in FIG. 4K. At FIG. 4L the entire structure may be subjected to a drying process which may shrink the cathode slurry 440 to also be at the height of the PET layer top. Proceeding to FIG. 4M, a cathode film layer 450, which may already have the cathode collector film upon it, may be bonded to the growing structure. In a final illustration at FIG. 4N a laser cutting process may be performed to remove side regions 460 and yield a battery element 470. There may be numerous alterations, deletions, changes to materials and thickness targets that may be useful within the intent of the present invention.

The result of the exemplary processing may be depicted in some detail at FIG. 5. In an example, the following reference features may be defined. The Cathode chemistry 510 may be located in contact with the cathode and cathode collector 520. A pressure-sensitive adhesive layer 530 may hold and seal the cathode collector 520 to a PET Spacer layer 540. On the other side of the PET Spacer layer 540, may be another PSA layer 550, which seals and adheres the PET Spacer layer 540 to the PET Gap layer 560. Another PSA layer 565 may seal and adhere the PET Gap layer 560 to the Anode and Anode Current Collector layers. A Zinc Plated layer 570 may be plated onto the Anode Current Collector 580. The separator layer 590 may be located within the structure to perform the associated functions as have been defined in the present invention. In some examples, an electrolyte may be added during the processing of the device, in other examples, the separator may already include electrolyte.

Exemplary Processing Illustration of Biocompatible Energization Elements—Deposited Separator An example of the steps that may be involved in processing biocompatible energization elements may be found in FIGS. 6A-6F. The processing at some of the exemplary steps may be found in the individual figures. There may be numerous alterations, deletions, changes to materials and thickness targets that may be useful within the intent of the present invention.

In FIG. 6A, an exemplary laminar construct 600 is illustrated. The laminar structure may comprise two laminar construct release layers, 602 and 602a; two laminar construct adhesive layers 604 and 604a, located between the laminar construct release layers 602 and 602a; and a laminar construct core 606, located between the two laminar construct adhesive layers 604 and 604a. The laminar construct release layers, 602 and 602a, and adhesive layers, 604 and 604a, may be produced or purchased, such as a commercially available pressure-sensitive adhesive transfer tape with primary liner layer. The laminar construct adhesive layers may be a PVDF layer which may be approximately 1-3 millimeters in thickness and cap the laminar construct core 606. The laminar construct core 606 may comprise a thermoplastic polymer resin such as polyethylene terephthalate, which, for example, may be roughly 3 millimeters thick. Proceeding to FIG. 6B, a means for storing the cathode mixture, such as a cavity for the cathode pocket 608, may be cut in the laminar construct by laser cutting treatment.

Next, at FIG. 6C, the bottom laminar construct release layer 602a may be removed from the laminar construct, exposing the laminar construct adhesive layer 604a. The laminar construct adhesive layer 604a may then be used to adhere an anode connection foil 610 to cover the bottom opening of the cathode pocket 608. Proceeding to FIG. 6D, the anode connection foil 610 may be protected on the exposed bottom layer by adhering a masking layer 612. The masking layer 612 may be a commercially available PSA transfer tape with a primary liner. Next, at FIG. 6E, the anode connection foil 610 may be electroplated with a coherent metal 614, zinc, for example, which coats the exposed section of the anode connection foil 610 inside of the cathode pocket. Proceeding to 6F, the anode electrical collection masking layer 612 is removed from the bottom of the anode connection foil 610 after electroplating.

FIGS. 7A-7F illustrate an alternate mode of processing the steps illustrated in FIGS. 6A-6F. FIGS. 7A-7B illustrate similar processes as depicted in FIGS. 6A-6B. The laminar structure may comprise two laminar construct release layers, 702 and 702a, one layer on either end; two laminar construct adhesive layers, 704 and 704a, located between the laminar construct release layers 702 and 702a; and a laminar construct core 706, located between the two laminar construct adhesive layers 704 and 704a. The laminar construct release layers and adhesive layers may be produced or purchased, such as a commercially available pressure-sensitive adhesive transfer tape with primary liner layer. The laminar construct adhesive layers may be a polyvinylidene fluoride (PVDF) layer which may be approximately 1-3 millimeters in thickness and cap the laminar construct core 706. The laminar construct core 706 may comprise a thermoplastic polymer resin such as polyethylene terephthalate, which, for example, may be roughly 3 millimeters thick. Proceeding to FIG. 7B, a storage means, such as a cavity, for the cathode pocket 708, may be cut in the laminar construct by laser cutting treatment. In FIG. 7C, an anode connection foil 710 may be obtained and a protective masking layer 712 applied to one side. Next, at FIG. 7D, the anode connection foil 710 may be electroplated with a layer 714 of a coherent metal, for example, zinc. Proceeding to FIG. 7E, the laminar constructs of FIGS. 7B and 7D may be combined to form a new laminar construct as depicted in FIG. 7E by adhering the construct of FIG. 7B to the electroplated layer 714 of FIG. 7D. The release layer 702a of FIG. 7B may be removed in order to expose adhesive layer 704a of FIG. 7B for adherence onto electroplated layer 714 of FIG. 7D. Proceeding next to FIG. 7F, the anode protective masking layer 712 may be removed from the bottom of the anode connection foil 710.

FIGS. 8A-8H may illustrate implementation of energization elements to a biocompatible laminar structure, which at times is referred to as a laminar assembly or a laminate assembly herein, similar to, for example, those illustrated in FIGS. 6A-6F and 7A-7F. Proceeding to FIG. 8A, a hydrogel separator precursor mixture 820 may be deposited on the surface of the laminate assembly. In some examples, as depicted, the hydrogel precursor mixture 820 may be applied up a release layer 802. Next, at FIG. 8B, the hydrogel separator precursor mixture 820 may be squeegeed 850 into the cathode pocket while being cleaned off of the release layer 802. The term "squeegeed" may generally refer to the use of a planarizing or scraping tool to rub across the surface and move fluid material over the surface and into cavities as they exist. The process of squeegeeing may be performed by equipment similar to the vernacular "Squeegee" type device or alternatively and planarizing device such as knife edges, razor edges and the like which may be made of numerous materials as may be chemically consistent with the material to be moved.

The processing depicted at FIG. 8B may be performed several times to ensure coating of the cathode pocket, and increment the thickness of resulting features. Next, at FIG. 8C, the hydrogel separator precursor mixture may be allowed to dry in order to evaporate materials, which may typically be solvents or diluents of various types, from the hydrogel separator precursor mixture, and then the dispensed and applied materials may be cured. It may be possible to repeat both of the processes depicted at FIG. 8B and FIG. 8C in combination in some examples. In some examples, the hydrogel separator precursor mixture may be cured by exposure to heat while in other examples the curing may be performed by exposure to photon energy. In still further examples the curing may involve both exposure to photon energy and to heat. There may be numerous manners to cure the hydrogel separator precursor mixture.

The result of curing may be to form the hydrogel separator precursor material to the wall of the cavity as well as the surface region in proximity to an anode or cathode feature which in the present example may be an anode feature. Adherence of the material to the sidewalls of the cavity may be useful in the separation function of a separator. The result of curing may be to form an anhydrous polymerized precursor mixture concentrate 822 which may be simply considered the separator of the cell. Proceeding to FIG. 8D, cathode slurry 830 may be deposited onto the surface of the laminar construct release layer 802. Next, at FIG. 8E the cathode slurry 830 may be squeegeed into the cathode pocket and onto the anhydrous polymerized precursor mixture concentrate 822. The cathode slurry may be moved to its desired location in the cavity while simultaneously being cleaned off to a large degree from the laminar construct release layer 802. The process of FIG. 8E may be performed several times to ensure coating of the cathode slurry 830 on top of the anhydrous polymerized precursor mixture concentrate 822. Next, at FIG. 8F, the cathode slurry may be allowed to dry down to form an isolated cathode fill 832 on top of the anhydrous polymerized precursor mixture concentrate 822, filling in the remainder of the cathode pocket.

Proceeding to FIG. 8G, an electrolyte formulation 840 may be added on to the isolated cathode fill 832 and allowed to hydrate the isolated cathode fill 832 and the anhydrous polymerized precursor mixture concentrate 822. Next, at FIG. 8H, a cathode connection foil 816 may be adhered to the remaining laminar construct adhesive layer 804 by removing the remaining laminar construct release layer 802 and pressing the connection foil 816 in place. The resulting placement may result in covering the hydrated cathode fill 842 as well as establishing electrical contact to the cathode fill 842 as a cathode current collector and connection means.

FIGS. 9A through 9C may illustrate an alternative example of the resulting laminate assembly from FIG. 7D. In FIG. 9A, the anode connection foil 710 may be obtained and a protective masking layer 712 applied to one side. The anode connection foil 710 may be plated with a layer 714 of coherent metal with, for example, zinc. In similar fashion as described in the previous figures. Proceeding to FIG. 9B, a hydrogel separator 910 may be applied without the use of the squeegee method illustrated in FIG. 8E. The hydrogel separator precursor mixture may be applied in various manners, for example, a preformed film of the mixture may be adhered by physical adherence; alternatively, a diluted mixture of the hydrogel separator precursor mixture may be dispensed and then adjusted to a desired thickness by the processing of spin coating. Alternatively the material may be applied by spray coating, or any other processing equivalent. Next, at FIG. 9C, processing is depicted to create a segment of the hydrogel separator that may function as a containment around a separator region. The processing may create a region that limits the flow, or diffusion, of materials such as electrolyte outside the internal structure of the formed battery elements. Such a blocking feature 920 of various types may therefore be formed. The blocking feature, in some examples, may correspond to a highly crosslinked region of the separator layer as may be formed in some examples by increased exposure to photon energy in the desired region of the blocking feature 920. In other examples, materials may be added to the hydrogel separator material before it is cured to create regionally differentiated portions that upon curing become the blocking feature 920.

In still further examples, regions of the hydrogel separator material may be removed either before or after curing by various techniques including, for example, chemical etch of the layer with masking to define the regional extent. The region of removed material may create a blocking feature in its own right or alternatively materially may be added back into the void to create a blocking feature. The processing of the impermeable segment may occur through several methods including image out processing, increased cross-linking, heavy photodosing, back-filling, or omission of hydrogel adherence to create a void. In some examples, a laminate construct or assembly of the type depicted as the result of the processing in FIG. 9C may be formed without the blocking feature 920.

Polymerized Battery Element Separators

In some battery designs, the use of a discrete separator (as described in a previous section) may be precluded due to a variety of reasons such as the cost, the availability of materials, the quality of materials, or the complexity of processing for some material options as non-limiting examples. In such cases, a cast or form-in-place separator which is illustrated in the processes of FIGS. 8A-8H, for example, may provide desirable benefits. While starch or pasted separators have been used commercially with success in AA and other format Leclanché or zinc-carbon batteries, such separators may be unsuitable in some ways for use in certain examples of laminar microbatteries. Particular attention may need to be paid to the uniformity and consistency of geometry for any separator used in the batteries of the present invention. Precise control over separator volume may be needed to facilitate precise subsequent incorporation of known cathode volumes and subsequent realization of consistent discharge capacities and cell performance.

A method to achieve a uniform, mechanically robust form-in-place separator may be to use UV-curable hydrogel formulations. Numerous water-permeable hydrogel formulations may be known in various industries, for example, the contact lens industry. An example of a common hydrogel in the contact lens industry may be poly(hydroxyethylmethacrylate) crosslinked gel, or simply pHEMA. For numerous applications of the present invention, pHEMA may possess many attractive properties for use in Leclanché and zinc-carbon batteries. pHEMA typically may maintain a water content of approximately 30-40 percent in the hydrated state while maintaining an elastic modulus of about 100 psi or greater. Furthermore, the modulus and water content properties of crosslinked hydrogels may be adjusted by one of skill in the art by incorporating additional hydrophilic monomeric (e.g. methacrylic acid) or polymeric (e.g. polyvinylpyrrolidone) components. In this manner, the water content, or more specifically, the ionic permeability of the hydrogel may be adjusted by formulation.

Of particular advantage in some examples, a castable and polymerizable hydrogel formulation may contain one or more diluents to facilitate processing. The diluent may be chosen to be volatile such that the castable mixture may be squeegeed into a cavity, and then allowed a sufficient drying time to remove the volatile solvent component. After drying, a bulk photopolymerization may be initiated by exposure to actinic radiation of appropriate wavelength, such as blue UV light at 420 nm, for the chosen photoinitiator, such as CGI 819. The volatile diluent may help to provide a desirable application viscosity so as to facilitate casting a uniform layer of polymerizable material in the cavity. The volatile diluent may also provide beneficial surface tension lowering effects, particularly in the case where strongly polar monomers are incorporated in the formulation. Another aspect that may be important to achieve the casting of a uniform layer of polymerizable material in the cavity may be the application viscosity. Common small molar mass reactive monomers typically do not have very high viscosities, which may be typically only a few centipoise. In an effort to provide beneficial viscosity control of the castable and polymerizable separator material, a high molar mass polymeric component known to be compatible with the polymerizable material may be selected for incorporation into the formulation. Examples of high molar mass polymers which may be suitable for incorporation into exemplary formulations may include polyvinylpyrrolidone and polyethylene oxide.

In some examples the castable, polymerizable separator may be advantageously applied into a designed cavity, as previously described. In alternative examples, there may be no cavity at the time of polymerization. Instead, the castable, polymerizable separator formulation may be coated onto an electrode-containing substrate, for example, patterned zinc plated brass, and then subsequently exposed to actinic radiation using a photomask to selectively polymerize the separator material in targeted areas. Unreacted separator material may then be removed by exposure to appropriate rinsing solvents. In these examples, the separator material may be designated as a photo-patternable separator.

Primary Battery Example

In some examples of the processing of biocompatible energization elements with deposited separators, a primary battery may be formed. A typical primary battery may be characterized by its single-use property. In an example consistent with the laminar processing a battery may be formed with the following characteristics and elements.

| Element | Material |
| --- | --- |
| Cathode Current collector | Brass |
| Cathode (Slurry) | Electrolytic Manganese Dioxide Base |
| Separator | Hydrogel |
| Anode | Electrodeposited Zinc |
| Anode Current collector | Brass |
| Laminate | Polyethylene Terphalate Base |
| Electrolyte | ZnCl2/NH4CL Base |

There may be numerous formulations of cathode chemistry that may be consistent with this disclosure. As a non-limiting example, a formulation may comprise Electrolytic Manganese Dioxide in a Graphite mixture. In an example a powder mixture may be formed by mixing Jet Milled Electrolytic Manganese Dioxide (JMEMD) and KS6 graphite as available from Timcal (TIMCAL TIMREX® KS6 Primary Synthetic Graphite) in a 80 percent JMEMD to 20 percent KS6 ratio by weight. The mixing may be performed by numerous means, as an example the JMEMD and KS6 may be mixed by grind milling the two powders for an extended period. In some examples, the resulting powder mixture may be mixed with a 10 percent Polyisobutylene (PIB) in Toluene solution. The 10 percent PIB solution may be formed from Polyisobutylene grade B50 mixed with toluene in a roughly 10 parts PIB B50 to 90 parts toluene formulation by weight. The 10 percent PIB may be mixed with an additional amount of toluene and with the JMEMD/K6 powder to formulate a slurry for cathode processing. This mixture may include these materials in a ratio of roughly 1.5 parts PIB B50/Toluene solution to 2.3 parts Toluene to 4.9 parts JMEMD/KS6 powder. The mixing may proceed until a uniform slurry with a pastelike consistency is formed. The amount of solvent (toluene in an example) in the system may be varied to affect the characteristics of the slurry formed, and in other examples the relative amount of PIB B50 in the slurry may be varied from the example.

Continuing with the primary battery example, a hydrogel separator may be formed in the manners discussed in this disclosure from a precursor mixture. An example of a precursor mixture may be formed by mixing hydroxyethylmethacrylate (HEMA); with ethylene glycol dimethylacrylate (EGDMA); and with polyvinylpyrrolidone (PVP). There may be other constituents added to the mixture such as photoinitiators. An exemplary photoinitiator may be phenylbis(2,4,6-trimethylbenzoyl)-phosphine oxide which may be available in commercial formulations including Irgacure® 819 which may also be called CGI 819 herein. There may also be numerous solvents that may be used in varying amounts to reach a desired rheology of the mixture. In a non-limiting example, 2-proponol may be used as an appropriate solvent.

Many of the general discussions on elements of biocompatible energization devices such as the cathode and cathode slurry have examples related to primary battery elements and the variations and examples for these various elements may be expected to comprise other examples of primary battery elements for the present specification.

In some examples, the zinc anode may be formed by electrodepositing the zinc upon the contact material. In other examples, as have been discussed, the electrodeposition may occur through the laminate structure to only exposed portions of the contact material. There may be numerous manners of depositing anode materials and other battery systems may employ other chemical species other than zinc such as silver as a non-limiting example.

The battery may include various types of electrolyte formulations. Basic solution on hydroxide may be included in the electrolyte. However, in some examples of biocompatible batteries less basic electrolyte formulations may be utilized. Electrolytes for use in the present invention may include zinc chloride, zinc acetate, ammonium acetate, and ammonium chloride in mass concentrations from approximately 0.1 percent to 25 percent. As a non-limiting example a 5 wt. percent solution of zinc chloride and ammonium chloride may be dissolved in water as a base. In addition, surfactants may be added to the electrolyte formulation. Exemplary surfactants may include Triton™ X-100, Triton™ QS44, and Dowfax™ 3B2 in concentrations from 0.01 percent to 2 percent. As an example Triton™ X-100 may be added to the zinc chloride, ammonium chloride solution.

Secondary Battery Examples

The structure and manufacturing processes that have been described in the present disclosure may be useful in general for the production of secondary batteries. There may be a number of considerations related to secondary battery elements that may differ from considerations made for primary elements. The recharging process for a battery element may result in swelling and shrinking of battery components, and therefore the dimensions of features and containment layers as well as the composition of the battery may be adjusted in some embodiments. The use of gelled polymer layers for the electrolytes may allow for a layer which may take up some of the swelling and shrinking aspects as electrode ions are moved around the device during charging cycles, and subsequently, during discharging cycles.

In secondary batteries, the anode and cathode layers may switch designation depending on whether the device is charging or discharging, and may be considered first and second electrodes. Therefore, it may be useful to refer to the anode and cathode in reference to whether the battery cell is being charged such that it may be considered an electrolytic cell or whether it is being discharged such that it may be considered a galvanic cell. Therefore, when referred to as the cathode of the galvanic cell, the first electrode structure would function to spontaneously accept electrons from an externally connected circuit. As well, the cathode of the electrolytic cell is physically the second electrode in the secondary battery which accepts electrons from an external charging element.

Although in some examples the zinc manganese dioxide class of batteries can function as a secondary battery, there are many more common examples of secondary batteries. In a common class of secondary batteries, lithium ions may comprise the energy storing chemical species. There may be numerous manners to form electrodes in lithium ion batteries. In the type of devices according to the present disclosure, there may be numerous intercalated lithium compounds that might be present in the anode of the galvanic cell. For example, the cathode slurry may include Lithium Nickel Manganese Cobalt Oxide, Lithium Manganese Oxide, and Lithium Iron Phosphate amongst others.

The second electrode may be the anode of the galvanic cell and, in some examples, may be formed of or coated with graphite or other forms of carbon. In other examples, various forms of deposited silicon may be used. In similar manners to the electroplating of zinc discussed with respect to primary batteries, silicon may be electroplated either in regions or in a flat layer across the substrate. Electroplated silicon may be formed onto the current collector layer which may have surface coatings of platinum, titanium or a thin layer of silicon in some examples. The platting of the electrode material may occur in non-aqueous media comprising $SiCl4$, $SiHCL3$, $SiBr4$, $Si(Ch2Ch3)4$, or $Si(OOCCH3)4$ as non-limiting examples. In other examples, graphite or silicon layers may be sputter deposited to the current collector surface to form the second electrode region in a manner similar to that depicted at FIG. 7D.

The electrodes may be formed upon metal sheets in manners consistent with the prior discussions relating to laminate processing. These electrodes and metal sheets may form the base layer: i.e. underneath the laminate layers that form the cavity. Also, the current collector connected to the other electrode may be used to cap the laminate structure after the cathode has been formed and the cell has been filled with electrolyte.

To form electrolyte solutions, lithium salts may typically be dissolved in non-aqueous solvent systems. Therefore, these non-aqueous solvent systems may interact with the various adhesive layers in different manners, and since the integrity of seals in the battery devices may be important, there may be alterations in the choice of adhesive systems that may be required depending on the use of non-aqueous solvents. Gelled forms of polymer electrolytes are known in lithium polymer devices incorporating polymer electrolytes. The methods of formation of separators starting with liquid precursor filling of a cavity may be performed for these types of secondary batteries where a polymerized separator may be formed from polymers such as PVDF or poly (acrylonitrile). In some examples, it may be possible to utilize hydrogel forming precursors where the polymer is gelled with conventional salts consistent with Lithium cells. For example, in a non-limiting example a separator precursor may be mixed with lithium hexafluorophosphate in non-aqueous solvents such as ethylene carbonate, dimethyl carbonate, and diethyl carbonate as non-limiting examples. The resulting gelled layer may be formed with excess solvent to allow for shrinkage as has been described in relationship to the hydrogel precursor processing.

In a specific non-limiting example, a cavity-based laminate structure may be formed, as has been described in the prior discussion of laminate processing, where the bottom layer may be the current collector upon which a graphite or silicon layer has been attached. The laminate layers that attach to the current collector may have the cavities formed into them as has been described. In a non-limiting example, a casting solution may be formed by mixing a roughly two to one ratio of poly(vinylidene fluoride) (PVDF) and poly (dimethylsiloxane) (PDMS) into a solvent mixture comprising N—N Dimethyl Acetamide (DMAc) and glycerol. The ratio of the DMAc to glycerol may be varied and may affect characteristics such as the porosity of the resulting separator layer. An excess of the solvent mixture may be used to allow for the shrinkage of the resulting layer in the cavity to form a thin separator layer. In some examples, especially for high levels of solvent, the adhesive system for the laminate structure may be altered to optimize consistency with the DMAc-glycerol solvent system. After squeegee processing of the casting solution into the defined cavities, the resulting structure may be dried at room temperature or elevated temperature for some time period. Other manners of dispensing the casting solution may be consistent with the processes described herein. Thereafter, the structure may be immersed into a room temperature water bath for 20-40 hours to allow for the glycerol to dissolve out of the separator layer and result in a layer with a desired porosity. The resulting structure may then be dried in a vacuum environment over a period of 20-40 hours.

In some examples, the resulting separator layer may be treated with exposure to an electrolyte solution. In a non-limiting example a 1 Molar Lithium Hexafluorophosphate solution in a roughly 1/1/1 mixture of Ethylene Carbonate (EC)/Dimethyl Carbonate (DMC) and Ethyl Methyl Carbonate (EMC) may be formed and dispensed into the cavity. In some other examples exposure to the electrolyte may occur after the cathode is formed into the cavity.

In a different type of example the laminate structure may be built in the manner outlined in reference to FIGS. 4A-4N. A separator, such as a film of Celgard may be cut to a size of a feature in a gap spacer layer and then placed into the laminate structure as opposed to being filed into the cavity. The placed separator may also be treated with an exposure to electrolyte before further processing with a "cathode slurry".

The resulting structure may now be ready to receive a treatment with the cathode slurry. A number of cathode slurries comprising different types of lithium compounds may be used; although, other chemical types than lithium may be possible. In a non-limiting example, a lithium iron phosphate (LiFePO4) based slurry may be used. In some examples the lithium iron phosphate slurry may be formed by first mixing sodium carboxymethyl cellulose in deionized water. To the resulting mixture, a powder comprising Lithium Iron Phosphate and conductive agents such as synthetic graphite and carbon black may then be added and extensively mixed. Next a further refined slurry may be formed by adding styrene butadiene rubber and extensively mixing. The slurry may then be processed into the cavity structure in means as have been described in the present disclosure such as through use of a squeegee process. The rheology of the slurry may be adjusted for optimizing the integrity of the squeegee based filing process for example, by adding or removing solvent or by adjusting the relative amount of the styrene butadiene rubber added. The resulting filled structure may then be dried in a vacuum environment over 20-40 hours.

In some examples, the resulting cathode and separator layers may be treated with exposure to an electrolyte solution. In a non-limiting example a 1 Molar Lithium Hexafluorophosphate solution in a roughly 1/1/1 mixture of Ethylene Carbonate (EC)/Dimethyl Carbonate (DMC) and Ethyl Methyl Carbonate (EMC) may be formed and dispensed into the cavity. In some examples, the electrolyte may be added to the cathode with the assistance of either pressure treatment or vacuum treatment to enhance the diffusion of the electrolyte mixture into the layers.

The second current collector layer may be attached to the laminate structure after the removal of a release layer from laminate structure. The adhered current collector may contact the deposited slurry and provide electrical contact between the metal current collector and the electrolyte infused cathode resulting in a battery structure.

Multi-Battery Interconnection Aspects

The laminar structure based on cavities creates a natural battery device that has multiple individual battery elements. There may be numerous advantages to battery devices that comprise individual elements such as has been described in U.S. patent application Ser. No. 13/358,916, filed on Jan. 26, 2012, (now U.S. Pat. No. 9,110,310), entitled MULTIPLE ENERGIZATION ELEMENTS IN STACKED INTEGRATED COMPONENT DEVICES, the contents of which are incorporated herein by reference. Referring to FIG. 10A, exemplary electrical interconnects for multi-battery elements are be depicted. Eleven individual battery cavities may be depicted as battery elements 1010-1020. Each battery element may have a corresponding trace that leads away from a battery to a interconnect junction element 1025. For example, battery element 1010 may have interconnect 1001, and independent battery element 1011 may have an independent interconnect 1002. The traces may be routed independently with electrical isolation until they reach the interconnect junction element 1025. In some examples, all eleven batteries may have a common ground connection on the back of the multi-battery element. In other examples, each of the individual battery elements may have a similar independent second contact as is depicted for the first contact in FIG. 10A.

Figure 10B:
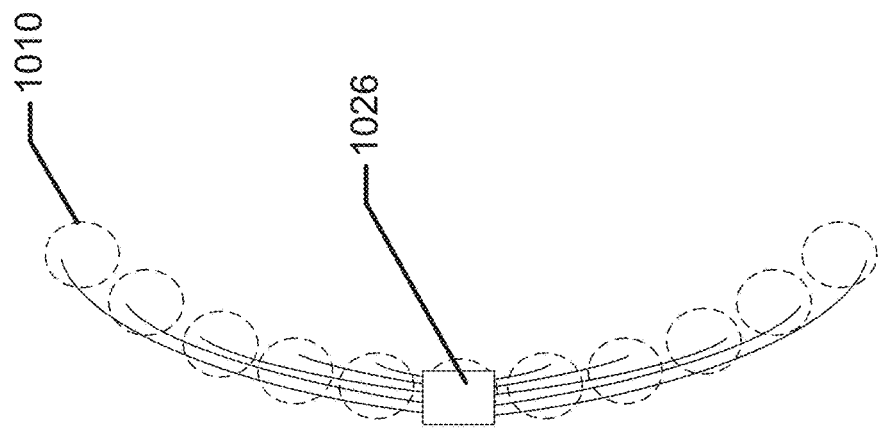
FIGS. 10A and 10B illustrate exemplary routings of interconnects and junction elements for multiple energization element devices.
Figure 10A:
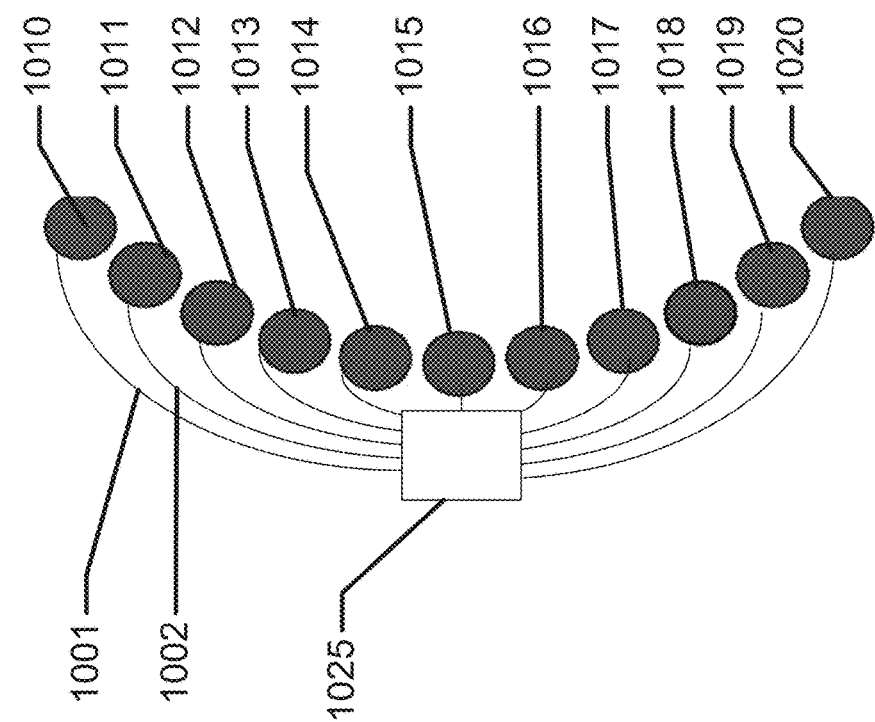

Proceeding to FIG. 10B an alternative example is depicted for eleven similar battery elements. As an example, the first battery element 1010 may be again depicted in FIG. 10B as with dotted lines to indicate that a different scheme of interconnect routing may be employed. In FIG. 10B the routing lines may be spatially contained to be above or below the battery elements, where the interconnect junction 1026 may therefore add to the height of the device, rather than to the width as may be the case with FIG. 10A.

The interconnect junction devices 1025 or 1026 may comprise various devices. In some of the simpler examples, the interconnect junction device may merely provide routing connections amongst the interconnects which may be useful, amongst other things, for defining multiple battery voltages. In a next set of interconnect junction element examples, the element may contain interconnects and diode structures. The diodes may be standard PN junction diodes or, in other more preferred examples, may be low forward drop diodes such as Schottky diodes. The diodes may provide a passive means to isolate a defective or lower-capacity element from other devices. For example, each battery may have different open-circuit and loaded voltages, impedance, and discharge capacity. These differences may arise from slights differences in processing, assembly, storage, and aging or may arise from significant defects in the cells. For example, each battery's positive/cathode output may connect to a common node and a similar connection scheme may be performed for the anodes. In such an example, in which all batteries are directly connected in parallel, "strong" batteries, which may have high voltage and low internal resistance, may discharge through "weak" batteries, which may have low voltage and internal shorts. In such a parallel connection example, the performance of all batteries may be pulled to a "lowest common demonimator." In an extreme example all may discharge through a single cell having an internal short. Alternatively, examples in which the cathode/positive terminal of each battery is connected to a common node through a diode may limit reduction in performance. In such examples, in the event of a weak cell, the diode may limit the reverse current so that one cell cannot degrade the whole array. In some more intricate examples, integrated circuits may be added that may provide more sophisticated control over defective elements and may provide programmable means to create controlled output voltages of various kinds which may exceed the maximum voltage output of any simple additive combination of elements.

Proceeding to FIGS. 10C and 10D, examples in cross section corresponding to the examples in FIG. 10A and FIG. 10B are illustrated. At FIG. 10C, a cross section corresponding to some examples of FIG. 10 A may be found. A battery cathode 842 located in a cavity in a laminate structure may have a cathode contact 1031 and an anode contact 816. The individual battery elements may have singulated cathode contacts 1031 where metal may be removed in patterns between the battery elements forming isolation features 1030. An aerial view of the cathode contact may reveal that the battery cathode contact 1031 may be cut out in such a fashion that it has a routing interconnect feature for each individual cathode contact. Proceeding to FIG. 10D, a more complicated interconnect structure may be employed wherein an insulator layer 1040 may have contact vias cut into its structure to allow for the contact via 1050. In some examples, the cathode contacts 1031, the isolation features 1030, and the isolation layer 1040 may all comprise a laminate layer that may be added to the battery device in manners as have been described in earlier sections. In some examples, a conductive paste or adhesive may be added to the contact via structure to create a contact via 1050. Thereafter, interconnect routing lines such as interconnect 1001 may be created to electrically connect the battery elements to features such as the interconnect junction element. In some examples, there may be multiple interconnect junction elements for a collection of battery elements.

Referring to FIG. 10E, an illustration of a cross section of the battery elements, 1010 and 1011 of FIG. 1013 is illustrated. A cathode spacer layer may be formed from the laminar construct core 706, located between the two laminar construct adhesive layers 704 and 704a. A first hole in the cathode spacer layer contains a battery cathode fill 842 and a second hole in the cathode spacer layer contains the battery cathode fill 842. The independent interconnect 1002 at battery element 1011 represents a third current collector, wherein the third current collector is physically segmented from the second current collector of battery element 1010. The third current collector which is independent interconnect 1002 is in electrical connection with the cathode chemicals within the second hole located in the cathode spacer layer.

Voltage Supply Aspects of Multi-Battery Units

In some examples of devices with multiple energization units, the combination of the batteries into different series and parallel connections may define different embodiments. When two energization units are connected in a series manner, the voltage output of the energization elements add to give a higher voltage output. When two energization units are connected in a parallel manner, the voltage remains the same but the current capacities add together, ideally doubling the capacity of a single cell while also reducing the internal resistance by half. It may be apparent that in some embodiments, the interconnection of energization elements may be hardwired into the design of the element. However, in other embodiments, the elements may be combined through use of switching elements to define different power supply conditions that may be dynamically defined.

Proceeding to FIG. 11, an example of how switches (including the exemplary switches 1120-1122, 1130, 1140-1145, 1150, 1160-1165, 1170, and 1180-1185) may be used to define up to 4 different voltage supplies from the switched combination of four different energization elements are shown. It may be apparent that the number of elements provided is an exemplary sense and that many different combinations would define similar art within the spirit of the inventive art herein. As well, items 1101, 1102, 1103 and 1104 may define the ground connections of four different energization elements, or in some embodiments these may represent the ground connections of four different banks of energization elements as was demonstrated in the description of FIG. 8. In an exemplary sense, items 1105, 1106, 1107 and 1109 may define bias connections to each of the four depicted energization elements where the bias connection may assume a nominal voltage condition which may be 1.5 volts higher than the individual element ground connections, 1101, 1102, 1103 and 1104.

As shown in FIG. 11, there may be a microcontroller, item 1116, that is included in the energized device which, among its various control conditions, may control the number of power supplies that the multiple energization units are connected to define. In some embodiments, the microcontroller may connect to a switch controller, item 1115, which may index control signal level changes from the microcontroller into state changes to the individual switches. For ease of presentation, the output of item 1115 is shown as a single item 1110. In this set of embodiments, this signal is meant to represent the individual control lines that go out to the variety of switches depicted as items 1120 through 1185. There may be numerous types of switches that are consistent with the spirit of the inventive art herein, however in a non-limiting sense, the switches may be MOSFET switches in an exemplary sense. It may be apparent that any of the numerous mechanical and electrical type switches or other switch types that may be controlled by an electrical signal may comprise art within the spirit of the inventive art herein.

According to the circuit embodiment of FIG. 11, the control of the switches may be used to generate a number of different voltage conditions. As a starting example, the switches may be configured so that there are two different voltage conditions defined: both the 1.5 volt condition shown as item 1113 and the 3 volt condition shown as item 1112. There are numerous ways for this to happen; but for example, the following manner will be described where two different elements are used for each of the voltage conditions. One may consider combining the elements represented by their ground connections of item 1101 and 1102 as the 1.5 volt supply elements. For this to occur, item 1105, the bias connection for the first energization element may be observed to already connect to the 1.5 volt supply line item 1113. For the second energization element bias connection 1106 to connect to supply line 1113, switch 1142 may be turned to a connected state while switches 1143, 1144 and 1145 may be configured in a non-connected state. The ground connection of the second energization element may now be connected to the ground line, 1114 by activating switch 1130. To define the second supply line 1112, the 3 volt supply line, the common/ground connections of the third 1103 and forth 1104 elements may be connected to the 1.5 volt supply line 1113. For this to be enacted for the third element, switch 1121 may be activated, whereas switches 1120 and 1122 may be deactivated. This may cause connection 1103 to be at the 1.5 volt condition of element 1113. Switch 1150 may be deactivated in this case. For the fourth element, switch 1140 may be activated. Switch 1141 may also be activated; however, if it is inactive, the same condition may exist. Switch 1170 may be deactivated so that the connection to the ground line is not made.

The bias connections of the third 1107 and forth 1109 elements may now be connected to the 3 volt power line 1113. For the third element connection, switch 1163 should be active while switches 1162, 1164 and 1165 may be inactivated. For the fourth element 1109, switch 1183 may be active while switches 1182, 1184, and 1185 may be inactive. This set of connections may define one of the embodiments that may result in such a two-level (1.5 and 3 Volt) rough power supply condition through the exemplary use of 4 energization units.

The embodiments that may derive from the connections illustrated in FIG. 11 may result in a number of different power supply conditions that may result from the use of four energization elements or four banks of energization elements. It may be apparent that many more connections of energization elements may be consistent with the inventive art herein. In a non-limiting sense, there may be as few as two energization elements or any number more than that, which may be consistent with an energized device. In any of these embodiments, there may be similar concepts for switching the connections of the ground and bias side of the energization elements into parallel and series connection, which may result in multiples of the energization voltage of the individual energization element voltage. The description of a type of embodiment utilizing the switching infrastructure of FIG. 11 may, in some embodiments, describe a set of connections that may be programmed into an energized device and then utilized for the lifetime of the resulting device embodiment. For example, an energized device may have operational modes programmed where the number or nature of its power supplies may dynamically change. In a non-limiting exemplary sense, referring to FIG. 11, item 1110 may represent a power supply line of the device where, in some modes, the device is not connected to any energization element connections as may be the case if switches 1145, 1165 and 1185 are in a non-activated connection. Other embodiments of this type may result in the connection of one or more of switches 1145, 1165, and 1185 resulting in a defined energization voltage for the power-supply of item 1110. This dynamic activation of a particular voltage may also include deactivation at a later time, or alternatively, a dynamic change to another operating energization voltage. There may be a significant diversity of operational embodiments that may derive from the inventive art herein when energized devices are included with multiple energization elements, which may be connected in static and dynamic manners to other elements of the energized device.

Multiple Energization Elements in Energized Devices

Figure 12:
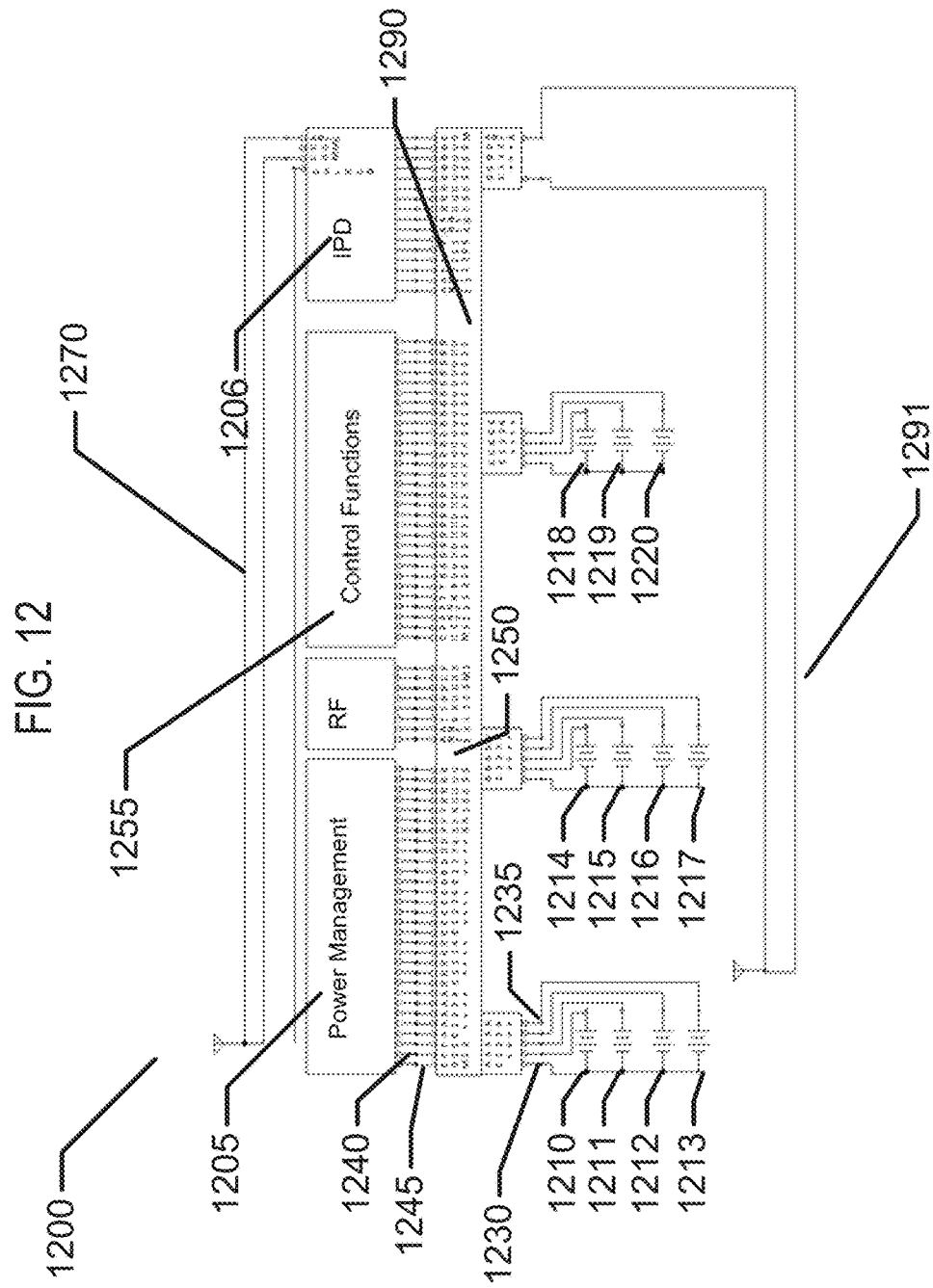
FIG. 12 illustrates an exemplary device with multiple energization elements where the elements may be formed as rechargeable elements.

Proceeding to FIG. 12, item 1200, a schematic representation of an embodiment with a battery element of the type shown in FIG. 10A, is illustrated. The multiple energization elements that were identified as items 1010-1020 in FIG. 10A may now be represented by individual identifiers associated with batteries. It may be apparent that the number and organization of the multiple elements are but one of many different arrangements and are depicted for illustrative purposes. Nevertheless, in some embodiments as shown, the elements may be arranged in banks. In FIG. 12, a first bank of elements may therefore include 1210, 1211, 1212 and 1213. A second bank of elements may include items 1214, 1215, 1216 and 1217. A third bank of elements may be represented by elements 1218, 1219, and 1220. An antenna element may also be demonstrated.

In some embodiments, each of these banks may share a common ground line for the three or four elements that are connected in the bank. For illustrative purposes, bank one, including items 1210, 1211, 1212 and 1213, may share a common ground line: shown as item 1230. Additionally, each of the elements may then have a separate line connecting them to an interconnect element, which may be represented by the circuit element 1290. It may be clear that numerous differences in the connection, count, and the make-up of each battery element may comprise art within the scope of this inventive art. Also, it may be possible that each battery element has both a common and a biased electrode separately connected to the interconnect layer.

As mentioned, in some embodiments where banks of battery elements share a common ground, that battery element 1213 may share a common connection 1230 and also have its own bias connection 1235. These connections may interface with the interconnection element 1290 and then continue on to a power management element identified in this figure as item 1205. The two connections may have corresponding input connections into the power management unit where 1240 may be a continuation of the bank. A common ground connection 1230 and item 1245 may be a continuation of the battery element 1213 bias connection 1235. Thus, the individual battery element may be connected to the power management entity, and switches may control how it is electrically connect to further elements. In some embodiments, the three banks of eleven multiple energization units may all in fact be connected in a parallel fashion. The parallel fashion may generate a raw battery power supply that has the same voltage condition of the battery elements and a combined battery capacity of the eleven units. The power management unit 1205 may connect each of the eleven elements 1210-1220 in such a parallel fashion. In alternative embodiments, the power management element may refine and alter the input power to result in a refined power output that will be supplied to the rest of the energized device. It may be apparent that numerous electrical refinements may be performed by the power management element, including in a non-limiting sense, regulating all the elements to match a standard reference voltage output; multiplying the voltage of the individual elements; regulating the current outputted by the combined battery elements; and many other such refinements.

In some embodiments, the raw output of the power management unit may be connected to the interconnection layer as shown by element 1250. This power supply may be passed through the interconnection device and electrically fed to an integrated passive device element (IPD) 1206 which may be connected to the multiple-battery element. Within the integrated passive device element 1206, there may be capacitors. The raw power supply connection that comes from the interconnect 1255 may be used to charge the capacitors to the voltage condition of the raw power supply. In some embodiments, the charging may be controlled by an active element; in other embodiments, it may just be passed onto the capacitor element. The resulting connection of the capacitor may then be identified as a first power supply condition.

Capacitors may be placed into the integrated passive device element to store energy for use by the various electroactive elements. In other examples, the capacitors may be included as part of the power management device itself or on the other components that are drawing power from the power management device. In still further examples, capacitors may be included into the overall device both as passive elements as well as integrated elements in other devices such as the power management device.

There may be numerous motivations for conditioning the power provided by multiple energization units. An exemplary motivation, in some embodiments, may derive from the power requirements of the components that are connected. If these elements have different operating states that require different current conditions, then the current draw of the highest operating state current draw may be buffered by the presence of the capacitors. Thus, the capacitors may store significantly more current capacity then the eleven battery elements may be able to provide at a given point in time. Depending on the conditions of the current drawing element, and of the nature of the capacitors in the IPD item 1206, there may still be a limitation of the amount of time during which a transient high current drawing state may occur and not overwhelm the battery. Since the capacitors would need to be recharged after a high draw on their current capacity, it may be obvious that there may need to be a sufficient time between reoccurrences of the high current draw condition. Therefore, it may be clear that there could be a large number of different design aspects relating to (1) the number of energization units, (2) their energy capacities, (3) the types of devices they connect to, and (4) the design power requirements of the elements that are provided energy by (a) these energization elements, (b) the power management system, and (c) the integrated passive devices.

Self-Testing and Reliability Aspects of Multiple Energization Units

The nature of energization elements may include aspects where when the elements are assembled into energized devices they may have failure modes that may have the nature of an initial or "time zero" failure; or alternatively, be an aged failure where an initially functioning element may fail during the course of its use. The characteristics of energized component devices with multiple energization elements allow for embodiments of circuitry and design which allow for remediating such failure modes and maintaining a functional operational state.

Returning to FIG. 12, some embodiments of self-testing and repair may be illustrated in an exemplary sense. Consider an embodiment type where the eleven multiple energization elements, 1210 to 1220 are all connected in a parallel manner to define one power supply condition based on the standard operating voltage of each element. As mentioned, the nature of combining these multiple number of energization elements may allow the Energized Device to perform self-testing and repair if an energization unit is defective or becomes defective. A sensing element may be used to detect the current flowing through the energization devices.

There may be numerous ways to set a condition in the energized device where its current may be at a standard value. In an exemplary sense, the device could have a "Sleep mode" that it activates where the quiescent current draw is at a very low value. The sensing protocol may be as straightforward as inserting a resistive element into the power-supply ground return line; although, more sophisticated means of measuring current flow, including magnetic or thermal transducers or any other means of performing electrical current metrology, may be consistent with the spirit of the art herein. If the diagnostic measurement of the current flow (in some embodiments represented as a voltage drop through the resistive element compared to a reference voltage) is found to exceed a standard tolerance, then the exemplary self-test circuitry may proceed to determine if one of the energization elements is causing the excessive current draw condition. In proceeding, one exemplary manner of isolating the cause may be to first cycle through isolating one of the four banks at a time by disconnecting its ground return line. Referring back to FIG. 12, the bank of elements 1210, 1211, 1212 and 1213 may be the first bank to be isolated. Ground line 1230 may be disconnected. The same electrical current draw metrology may next be performed after the isolation. If the current sensed has now returned to a normal current draw, then the problem may be indicated to occur in that bank. If, alternatively, the current still remains out of a specified condition then the logical looping process may proceed to the next bank. It may be possible that after looping through all the banks, which in this exemplary sense may be three banks, the current draw is still outside of the normal tolerance. In such a case, and in some embodiments, the self-testing protocol may then exit its test of the energization elements and then either stop self-testing or initiate self-testing for some other potential current draw issue. In describing this self-testing protocol, it may be apparent that an exemplary protocol has been described to illustrate the concepts of the inventive art herein, and that numerous other protocols may result in a similar isolation of individual energization units which may be malfunctioning.

Proceeding with the exemplary protocol, when a defect has been found and isolated and then the current flow during the testing returns to a normal specification, a next isolation loop may be performed. Now that a problem has been isolated to an individual bank, the next checks may isolate a defective element within that bank. Therefore, the individual bank may again be activated; however, each of the four elements, for example 1210, 1211, 1212 and 1213, may have their bias connection disconnected. In FIG. 12, 1235 may represent the bias connection of element 1213 and if it were a defective part, when the bank is activated it will draw significant current until its bias connection is disconnected. So, after an element is isolated, the current draw may again be sensed. If the isolation of an element returns the current draw to a normal state, then that element may be indicated as defective and subsequently disconnected from the power supply system.

If the second looping process continues through all energization elements in a bank without the current returning to an acceptable value, the loop may end. In such an event, the self-test circuitry may then proceed to disable the entire bank from the power supply system; or in other embodiments, it may proceed with a different manner of isolating elements in the bank. There may be numerous manners to define self-diagnostic protocols for multiple energization units and the actions that are programed to occur based on these protocols.

Rechargeable Elements in Multiple Energization Units

Remaining still with FIG. 12, another set of embodiments that may result from integrating multiple energization elements into energized devices may be seen where the energization elements may be recharged. In some embodiments, where there are multiple energization elements (such as items 1210 to 1220) and there are elements within the energized device that may be useful for recharging an energization element, there may be the ability to charge some of the elements.

In an exemplary set of embodiments, an energized device containing multiple energization elements may be capable of receiving and processing RF signals from an antenna 1270 comprised within its device. In some embodiments, there may exist a second antenna 1291, which may be useful for receiving wireless energy (e.g. inductive energy transfer, RF, light, and the like) from the environment of the device and passing this energy to a power management device, 1205. In an exemplary sense, there may be included a microcontroller element 1255, which may both draw power from the energized device's energization units and also control the operations within the device. This microcontroller 1255 may process information that has been inputted to it using programmed algorithms to determine that the energization system of the eleven elements, 1210 to 1220, may have enough energy to support the power requirements of the current device function. This processing may occur where only a subset of the elements are being used to power the supply controlling circuitry of the power management device, In such examples, the remaining elements may then be connected to the charging circuitry 1245 of the power management component which may be receiving the power, as mentioned previously, that is being received by antenna 1291. For example, in the embodiment depicted in FIG. 12, the energized device may be placed into a state where three of the multiple energization elements, items 1218, 1219 and 1220, may be connected to the charging electronics. Simultaneously, the remaining 8 elements, items 1210 to 1217 may be connected to the supply circuitry, 1240. In this manner, an energized device with energization may be enabled, through the use of multiple energization elements, to operate in modes where the elements are both being charged and discharged simultaneously.

Single Use Energization Elements with Electroactive Elements.

Figure 13:
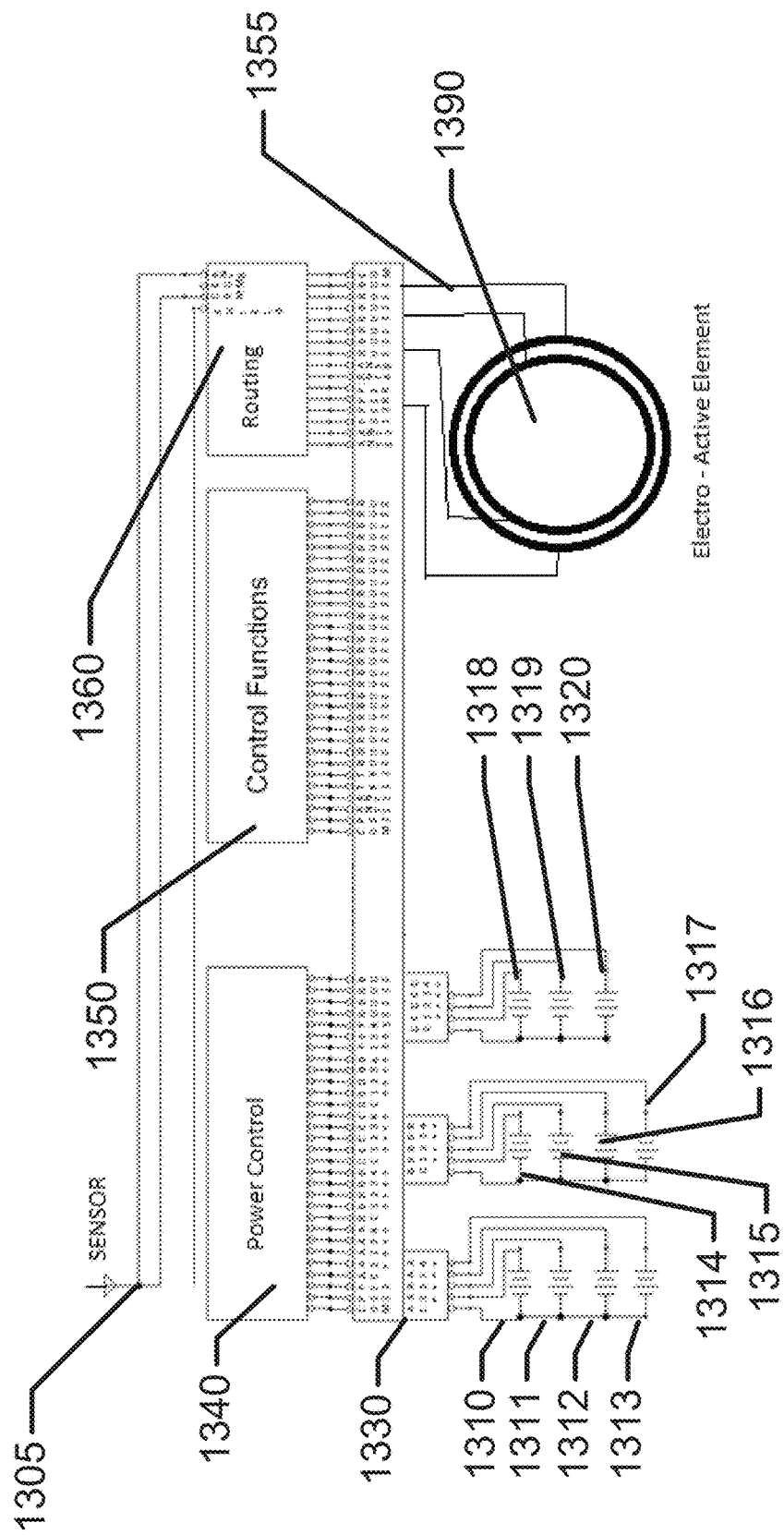
FIG. 13 illustrates an exemplary device with multiple energization elements where the elements may be formed as single-use elements.

Proceeding to FIG. 13, an example of a biocompatible device with multiple energization elements, where the energization elements are intended for single use, is depicted. In some examples, the energization elements may be batteries formed in laminate film processing with cavities. In some examples, there may be eleven battery elements shown as 1310 to 1320. The elements may be arranged into banks wherein each bank may have a common ground line and separate biased connections. The ground and bias connections may be routed through an interconnect junction element 1330. The interconnect junction element may connect to power control systems 1340, controller systems 1350, and various routing devices 1360. The device may receive external signals from a sensing element 1305. The device may provide controlling signals to an electroactive device element 1390 through interconnects 1355. In some examples, the electroactive device may be an electroactive focusing lens in a biocompatible ophthalmic device such as a contact lens. The single use battery elements may be sensed for working status and combined and acted up in power management circuits to ensure an operating life, even if some of the single use energization elements are not functional. The sensing element may be used to receive an activation signal and/or a level change signal which may change the status of the electroactive element.

The biocompatible devices can be, for example, implantable electronic devices, such as pacemakers and micro-energy harvesters, electronic pills for monitoring and/or testing a biological function, surgical devices with active components, ophthalmic devices, microsized pumps, defibrillators, stents, and the like.

Specific examples have been described to illustrate embodiments for the formation, methods of formation, and apparatus of formation of biocompatible energization elements comprising separators. These examples are for said illustration and are not intended to limit the scope of the claims in any manner. Accordingly, the description is intended to embrace all embodiments that may be apparent to those skilled in the art.

What is claimed is:

1. An apparatus for powering a biomedical device, the apparatus comprising:
   a laminate battery device with multiple energization elements for a biomedical device including powered components, comprising:
   a cathode spacer layer, wherein the cathode spacer layer comprises a laminar construct core located adjacent to at least a first laminar construct adhesive layer;
   a first hole located in the cathode spacer layer;
   a first current collector coated with anode chemicals, wherein the first current collector is attached to the first laminar construct adhesive layer of the cathode spacer layer, and wherein a first cavity is created between sides of the first hole and a first surface of the first current collector coated with anode chemicals;
   a separator layer, wherein the separator layer is formed within the first cavity after a separator precursor mixture is dispensed into the first cavity;
   a second cavity between sides of the first hole and a first surface of the separator layer, wherein the second cavity is filled with cathode chemicals within the second cavity;
   a first independent interconnect, wherein the first independent interconnect is in electrical connection with the cathode chemicals within the second cavity;
   a second independent interconnect, wherein the second independent interconnect is physically segmented from the first independent interconnect and is in electrical connection with cathode chemicals within a third cavity; wherein the third cavity is within a second hole located in the cathode spacer layer; and
   an interconnect junction element, wherein the interconnection junction element makes electrical connection to the first current collector, the first independent interconnect, and the second independent interconnect, wherein an electrical diode within the interconnect junction element makes connection to at least one of the first current collector, the the first independent interconnect, and the second independent interconnect.

* * * * *